(12) United States Patent
Hall et al.

(10) Patent No.: US 8,399,490 B2
(45) Date of Patent: Mar. 19, 2013

(54) INSECTICIDES

(75) Inventors: Roger Graham Hall, Stein (CH);
Olivier Loiseleur, Stein (CH); Jagadish Pabba, Goa (IN); Sitaram Pal, Ilhas Goa (IN); André Jeanguenat, Stein (CH); Andrew Edmunds, Stein (CH); André Denis Stoller, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 139 days.

(21) Appl. No.: 12/668,939

(22) PCT Filed: Jul. 14, 2008

(86) PCT No.: PCT/EP2008/005732
§ 371 (c)(1),
(2), (4) Date: Jun. 18, 2010

(87) PCT Pub. No.: WO2009/010260
PCT Pub. Date: Jan. 22, 2009

(65) Prior Publication Data
US 2010/0273830 A1 Oct. 28, 2010

(30) Foreign Application Priority Data

Jul. 16, 2007 (IN) .............. 1485/DEL/2007

(51) Int. Cl.
A61K 31/44 (2006.01)
C07D 473/00 (2006.01)
(52) U.S. Cl. ............ 514/338; 514/339; 546/275.4; 546/276.1
(58) Field of Classification Search ........... 514/338, 514/339; 546/275.4, 276.1
See application file for complete search history.

(56) References Cited

U.S. PATENT DOCUMENTS

2003/0229050 A1* 12/2003 Lahm et al. ............... 514/63
2009/0298816 A1* 12/2009 Loiseleur et al. .......... 514/229.8
2011/0271406 A1* 11/2011 Loiseleur et al. ............ 800/298

FOREIGN PATENT DOCUMENTS

| WO | 2005085234 | 9/2005 |
|---|---|---|
| WO | 2006111341 | 10/2006 |
| WO | 2007020050 | 2/2007 |
| WO | 2007093402 | 8/2007 |

* cited by examiner

Primary Examiner — Rei-tsang Shiao
(74) Attorney, Agent, or Firm — Dana Rewoldt

(57) ABSTRACT

An insecticidal compound of formula (I) in which $G_1$, $G_2$, and $G_3$ together with the two carbon atoms to which $G_1$ and $G_3$ are attached, form a non-aromatic 4- or 5-membered ring system; wherein $G_1$ is sulfur, SO, $SO_2$, oxygen, a direct bond, $NR_a$ or $CR_{5a}R_{5b}$; $G_2$ is sulfur, SO, $SO_2$, oxygen, a direct bond, $NR_b$ or $CR_{5c}R_{5d}$; $G_3$ is sulfur, SO, $SO_2$, oxygen, a direct bond, $NR_c$ or $CR_{5e}R_{5f}$; with the provisos that a) not more than 1 group G can be a direct bond, b) not more than 2 G groups can be oxygen, sulfur, SO or $SO_2$ and c) when 2 G groups are oxygen, SO, $SO_2$ and/or sulfur the two groups are separated by a carbon atom; each of $Z_1$ and $Z_2$, which may be the same or different, represents oxygen or sulfur; D is phenyl or a 5- or 6-membered heteroaromatic ring and $R_{1a}$, $R_{1b}$, $R_{5a}$, $R_{5b}$, $R_{5c}$, $R_{5d}$, $R_{5e}$, $R_{5f}$, $R_a$, $R_b$, $R_c$, $R_2$, $R_3$ and $R_{20}$ are specified organic groups and agronomically acceptable salts/isomers/enantiomers/tautomers/N-oxides of those compounds.

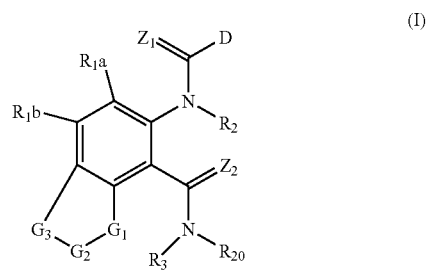

(I)

16 Claims, No Drawings

INSECTICIDES

This application is a 371 of International Application No. PCT/EP2008/005732 filed Jul. 14, 2008, which claims priority to IN 1485/DEL/2007 filed Jul. 16, 2007, the contents of which are incorporated herein by reference.

The present invention relates to bicyclic bisamide derivatives, to processes for their preparation, to compositions comprising those compounds, and to their use for controlling insects or representatives of the order Acarina.

Bisamide derivatives with insecticidal action are known and described, for example, in WO 2005/085234.

There have now been found novel bicyclic bisamide derivatives with pesticidal properties. The present invention accordingly relates to compounds of formula I

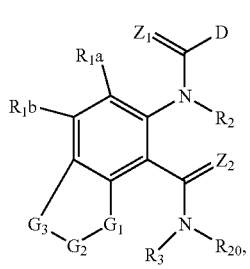

(I)

In which
$G_1$, $G_2$, and $G_3$ together with the two carbon atoms to which $G_1$ and $G_3$ are attached, form a non-aromatic 4- or 5-membered ring system; wherein
$G_1$ is sulfur, SO, $SO_2$, oxygen, a direct bond, $NR_a$ or $CR_{5a}R_{5b}$,
$G_2$ is sulfur, SO, $SO_2$, oxygen, a direct bond, $NR_b$ or $CR_{5c}R_{5d}$;
$G_3$ is sulfur, SO, $SO_2$, oxygen, a direct bond, $NR_c$ or $CR_{5e}R_{5f}$;
with the provisos that
a) not more than 1 group G can be a direct bond,
b) not more than 2 G groups can be oxygen, sulfur, SO or $SO_2$ and
c) when 2 G groups are oxygen, SO, $SO_2$ and/or sulfur the two groups are separated by a carbon atom;
each of $R_{1a}$, $R_{1b}$, $R_{5a}$, $R_{5b}$, $R_{5c}$, $R_{5d}$ $R_{5e}$, and $R_{5f}$, which may be the same or different, represents hydrogen, halogen, nitro, cyano, hydroxy, CHO, $NH_2$, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$trialkylsilyl, phenyl, benzyl or phenoxy; or phenyl, benzyl or phenoxy mono-, di- or trisubstituted by halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy or $C_3$-$C_6$trialkylsilyl;

each of $R_a$, $R_b$ and $R_c$, which may be the same or different, represents H, OH, $C_1$-$C_6$alkyl, $C_3$-$C_6$cycloalkyl, $C_1$-$C_6$haloalkyl, halogen, cyano, nitro, $NH_2$, $NR_{23}R_{24}$ $C_1$-$C_6$alkoxy, $C_1$-$C_6$haloalkoxy, $C_2$-$C_6$alkoxycarbonyl, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$haloalkylsulfinyl or $C_1$-$C_6$haloalkylsulfonyl, $C_2$-$C_6$ alkoxycarbonyl, $C_2$-$C_6$ alkylcarbonyl, $C_2$-$C_6$trialkylsilyl, benzyl, phenoxy and a three- to ten-membered, monocyclic or fused bicyclic ring system which may be aromatic, partially saturated or fully saturated, wherein the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_6$ dialkylaminocarbonyl and $C_2$-$C_6$ trialkylsilyl;

it being possible for said three- to ten-membered, monocyclic or fused bicyclic ring system to be spiro-bonded to the $C_3$-$C_6$cycloalkyl group;

each of $R_2$, $R_3$, $R_{23}$, $R_{24}$, $R_{25}$ and $R_{29}$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_6$cycloalkyl substituted by one or more substituents selected from halogen nitro, cyano, hydroxy, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$alkylamino, $C_2$-$C_4$dialkylamino, $C_3$-$C_6$cycloalkylamino and $C_1$-$C_6$alkyl-$C_3$-$C_6$cycloalkylamino;

or $R_{5a}$ and $R_{5b}$ or $R_{5c}$, and $R_{5d}$ or $R_{5e}$ and $R_{5f}$ can together form =Y, where Y can be O, S or $NR_{21}$;

D is 2-pyridyl, 3-pyridyl or 4-pyridyl; or 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfonyl, $C_1$-$C_4$haloalkylsulfinyl or $C_1$-$C_4$haloalkylsulfonyl;

or D is a group

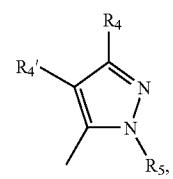

(D₁)

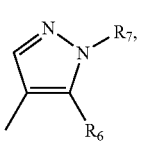
(D2)

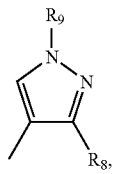
(D3)

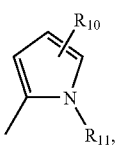
(D4)

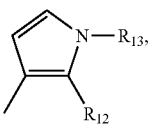
(D5)

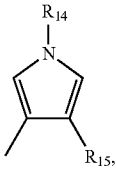
(D6)

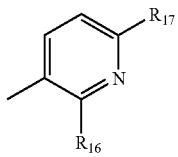
(D7)

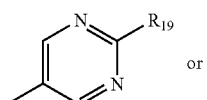
(D8)

or

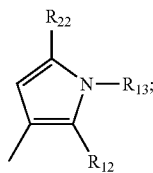
(D9)

or D is additionally phenyl if $Z_1$ is sulfur;

$R_4$, $R_4'$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_2$-$C_4$alkoxycarbonyl, $C_1$-$C_4$alkylthio, $C_1$-$C_4$alkylsulfonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$trialkylsilyl, benzyl, phenoxy and a three- to ten-membered, monocyclic or fused bicyclic ring system which may be aromatic, partially saturated or fully saturated, wherein the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$dialkylaminocarbonyl and $C_2$-$C_6$ trialkylsilyl;

it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

or $R_{20}$ is 3-oxetanyl, 3-thietanyl, 1-oxo-3-thietanyl, 1,1-dioxo-3-thietanyl, 1-imino-1-oxo-3-thietanyl, 3-azetidinyl, each optionally substituted with one to five substituents independently selected from $C_1$-$C_4$ alkyl, $C_1$-$C_4$ haloalkyl, halogen, cyano; each of $Z_1$ and $Z_2$, which may be the same or different, represents oxygen or sulfur;

$R_{21}$ is H, OH, $C_1$-$C_6$alkyl, $C_3$-$C_6$cycloalkyl, $C_1$-$C_6$haloalkyl, halogen, cyano, nitro, $NH_2$, $NR_{25}R_{29}$, $C_1$-$C_6$alkoxy, $C_1$-$C_6$haloalkoxy, $C_2$-$C_6$alkoxycarbonyl, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$haloalkylsulfinyl, $C_1$-$C_6$haloalkylsulfonyl, $C_2$-$C_6$ alkoxycarbonyl, $C_2$-$C_6$ alkylcarbonyl, $C_2$-$C_6$trialkylsilyl, benzyl, phenoxy or a three- to ten-membered, monocyclic or fused bicyclic ring system which may be aromatic, partially saturated or fully saturated, wherein the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl;

it being possible for said three- to ten-membered, monocyclic or fused bicyclic ring system to be spiro-bonded to the $C_3$-$C_6$cycloalkyl group;

$R_{22}$ is $C_1$-$C_6$alkyl, $C_3$-$C_6$cycloalkyl, $C_1$-$C_6$haloalkyl, halogen, cyano, nitro, $C_1$-$C_6$alkoxy, $C_1$-$C_6$haloalkoxy, $C_2$-$C_6$alkoxycarbonyl, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$haloalkylsulfinyl or $C_1$-$C_6$haloalkylsulfonyl;

and agronomically acceptable salts/isomers/enantiomers/tautomers/N-oxides of those compounds.

Compounds I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine. Where appropriate, the corresponding internal salts can furthermore be formed.

The alkyl groups occurring in the definitions of the substituents can be straight-chain or branched and are, for example, methyl, ethyl, n-propyl, isopropyl, n-butyl, sec-butyl, isobutyl, tert-butyl, pentyl and hexyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

According to the present invention, a three- to ten-membered monocyclic or fused bicyclic ring system which may be aromatic, partially saturated or fully saturated is, depending of the number of ring members, for example, selected from the group consisting of

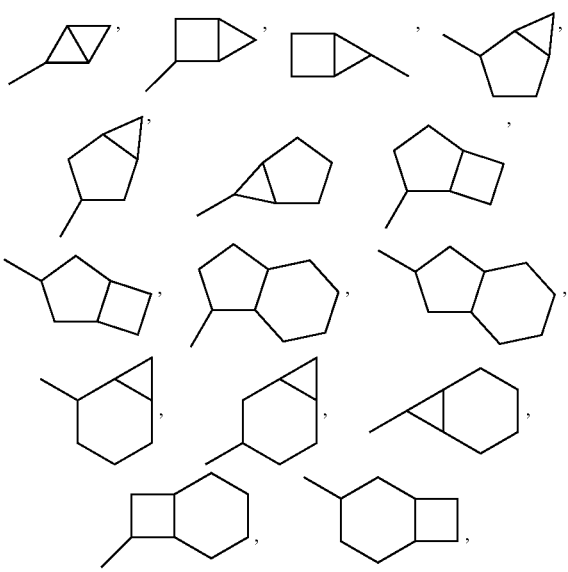

cyclopropyl, cyclobutyl, cyclopentyl, cyclohexyl, where said cycloalkyl groups for their part may be preferably unsubstituted or substituted by $C_1$-$C_6$alkyl or halogen, or is naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; to naphthyridinyl; (1-methyl-1H-pyrazol-3-yl)-; (1-ethyl-1'-1-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazoyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

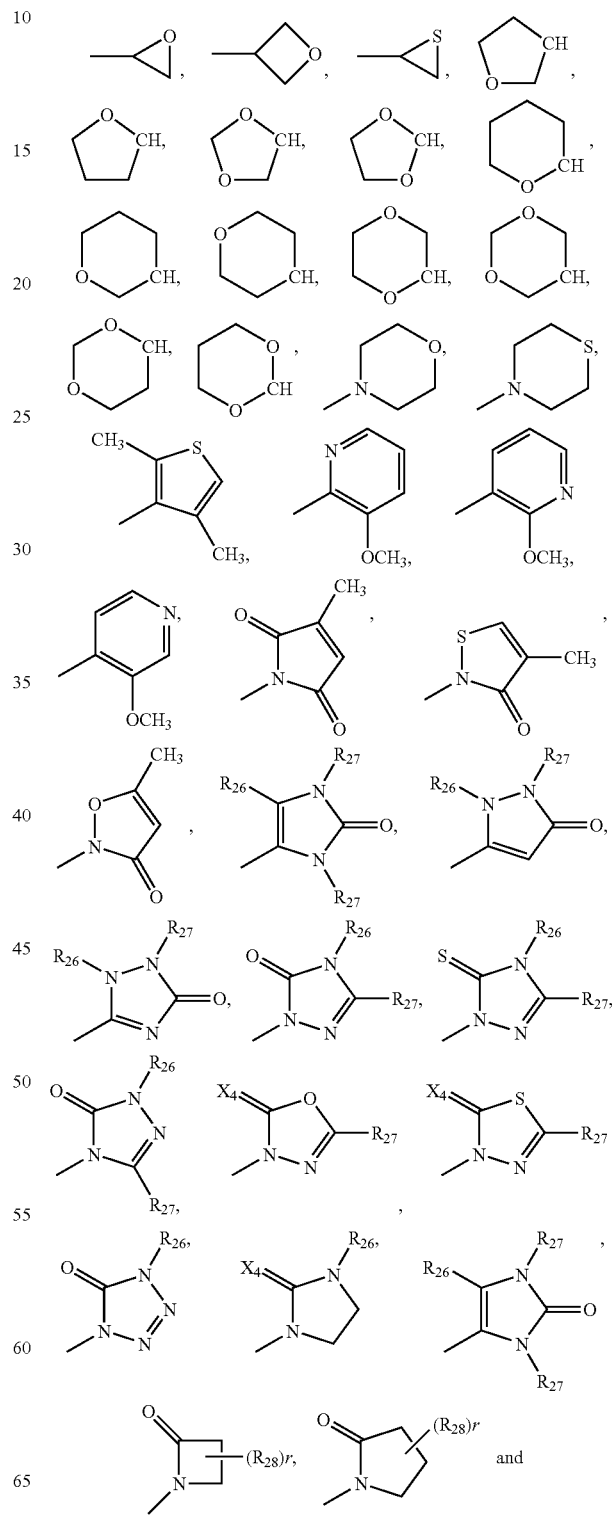

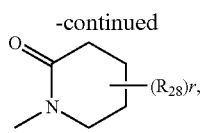

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulfur and r is 1, 2, 3 or 4.

Examples for a three- to ten-membered, monocyclic or fused bicyclic ring system which is spiro-bonded to the $C_3$-$C_6$cycloalkyl group of the substituent $R_{20}$ are

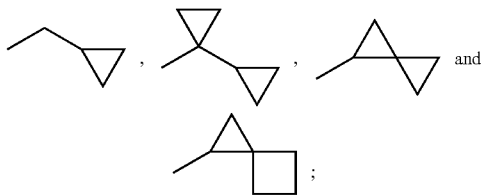

Where no free valency is indicated in those definitions, for example as in

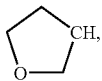

the linkage site is located at the carbon atom labelled "CH" or in a case such as, for example,

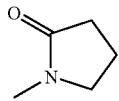

at the bonding site indicated at the bottom left.

Preferred groups for $Z_1$, $Z_2$, D, $G_1$, $G_2$, $G_3$, $R_{1a}$, $R_{1b}$, $R_2$, $R_3$ and $R_{20}$, in any combination thereof are set out below.

Preferably $Z_1$ and/or $Z_2$ are oxygen.

It is preferred that $R_2$ and/or $R_3$ is hydrogen.

$R_{20}$ is preferably hydrogen, methyl, ethyl, i-propyl, tert.-butyl, $CH_2$—$C_3H_5$, $C(CH_2CH_2)$—$C_3H_5$, $C(CH_3)_2$ $CH_2SCH_3$, $C(CH_3)_2CH_2S(O)CH_3$, $C(CH_3)_2CH_2S(O)_2CH_3$, $CH_2CN$, $CH(CH_3)CH_3SCH_3$, $CH(CH_3)CH_3S(O)CH_3$ or $CH(CH_3)CH_3S(O)_2CH_3$, 3-methyl-thietan-3-yl, 1-oxo-3-methyl-thietan-3-yl or 1,1-dioxo-3-methyl-thietan-3-yl, in particular hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)(NH)CH_3$, $C(CH_3)_2CH_2S(O)_2CH_3$, $CH_2CN$, $CH(CH_3)CH_2SCH_3$, $CH(CH_3)CH_2S(O)CH_3$, $CH(CH_3)CH_2S(O)(NH)CH_3$ or $CH(CH_3)CH_2S(O)_2CH_3$.

D is preferably a group $D_1$, wherein $R_4'$ is hydrogen, $R_5$ is 2-pyridyl which can be substituted by halogen, preferably which is monosubstituted by chloro at the 3-position of the pyridine ring and $R_4$ is halogen preferably chloro or bromo, $C_1$-$C_6$haloalkyl, $C_1$-$C_4$alkoxy, $C_1$-$C_4$haloalkoxy most preferably $OCH_3$, $OCF_2H$ or 2,2,2-trifluoroethoxy, preferably $C_1$-$C_6$haloalkyl, most preferably trifluoromethyl.

Preferably each of $R_{1a}$ and $R_{1b}$ which may be the same or different, represents hydrogen, halogen, cyano, hydroxy, CHO, $C_1$-$C_6$alkyl, $C_3$-$C_6$cycloalkyl, $C_1$-$C_6$haloalkyl, $C_1$-$C_4$alkoxy, $C_1$-$C_4$alkoxy-$C_1$-$C_4$alkoxy-$C_1$-$C_4$alkyl, $C_1$-$C_4$alkylthio, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_2$-$C_4$dialkylamino or $C_1$-$C_4$alkoxyimino-$C_1$-$C_4$alkyl.

Preferably each of $G_1$, $G_2$ and $G_3$ which may be the same or different, represents NH, O, S, SO, $SO_2$, $CR_{5a}R_{5b}$, $CR_{5c}R_{5d}$ or $CR_{5e}R_{5f}$ wherein each of $R_{5a}$, $R_{5b}$, $R_{6c}$, $R_{5d}$, $R_{5e}$ and $R_{5f}$ which may be the same or different represents hydrogen, halogen, cyano, hydroxy, CHO, $C_1$-$C_6$alkyl, $C_3$-$C_6$cycloalkyl, $C_1$-$C_6$haloalkyl, $C_1$-$C_4$alkoxy, $C_1$-$C_4$alkoxy-$C_1$-$C_4$alkoxy-$C_1$-$C_4$alkyl, $C_1$-$C_4$alkylthio, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_2$-$C_4$dialkylamino or $C_1$-$C_4$alkoxyimino-$C_1$-$C_4$alkyl.

A particularly preferred group of compounds of formula I is represented by the formula IA

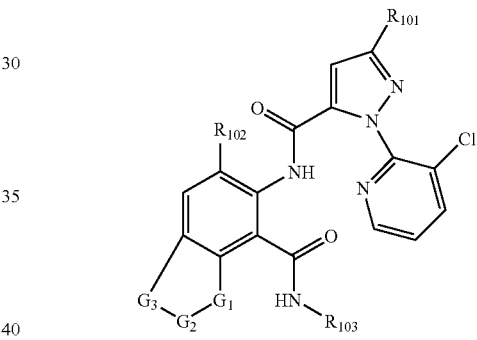

(IA)

wherein $G_1$, $G_2$ and $G_3$ have the meaning as given for formula I above;

$R_{101}$ is halogen, $C_1$-$C_4$haloalkyl, $C_1$-$C_4$haloalkoxy, $C_1$-$C_4$alkoxy, especially difluoromethyl, trifluoromethyl, chlorine, bromine, $OCF_2H$, O—$CH_2$—$CF_3$ or $OCH_3$, in particular halogen, haloalkyl, haloalkoxy, especially trifluoromethyl, chlorine, bromine, $OCF_2H$, $OCH_3$, or O—$CH_2$—$CF_3$;

$R_{102}$ is hydrogen, halogen, $C_1$-$C_6$-alkyl, $C_2$-$C_6$-alkynyl, cyano, especially methyl, ethynyl, chlorine or bromine; in particular halogen, $C_1$-$C_6$-alkyl, especially methyl, chlorine or bromine; and $R_{103}$ is hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)(NH)CH_3$, $C(CH_3)_2CH_2S(O)_2CH_3$, $CH_2CN$, $CH(CH_3)CH_2SCH_3$, $CH(CH_3)CH_2S(O)CH_3$, $CH(CH_3)CH_2S(O)_2CH_3$, 3-methyl-thietan-3-yl, 1-oxo-3-methyl-thietan-3-yl or 1,1-dioxo-3-methyl-thietan-3-yl; in particular methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)$ $CH_3$, $C(CH_3)_2CH_2S(O)(NH)CH_3$ or $C(CH_3)_2CH_2S(O)_2$ $CH_3$, $CH_2CN$, $CH(CH_3)CH_2SCH_3$, $CH(CH_3)CH_2S(O)CH_3$, $CH(CH_3)CH_2S(O)(NH)CH_3$ or $CH(CH_3)CH_2S(O)_2CH_3$.

Especially preferred compounds of formula I are represented by the following formulae:

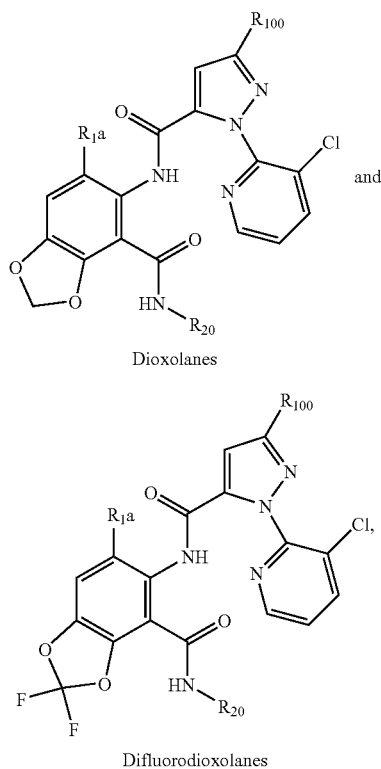

Dioxolanes (IB)

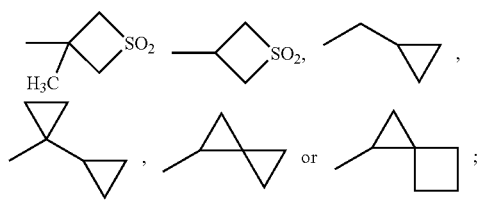

Difluorodioxolanes (IC)

in particular formula (IC);
wherein
$R_{1a}$ is hydrogen, $C_1$-$C_4$alkyl, $C_2$-$C_4$alkynyl, halogen or cyano;
$R_{20}$ is hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

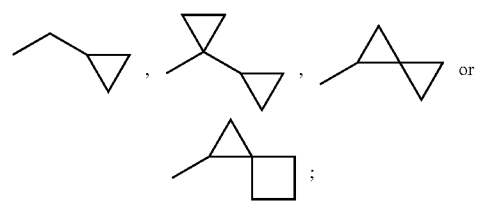

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, $R_{100}$ is halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$alkoxy.

Further preferred embodiments of the present invention are the embodiments E1 to E57, which are defined as compounds of formula I which are represented by one formula selected from the group consisting of the formulae T1 to T57 as described below, wherein in formulae T1 to T57
$R_{1a}$ is hydrogen, $C_1$-$C_4$alkyl, $C_2$-$C_4$alkynyl, halogen or cyano; in particular chloro or methyl;
$R_{20}$ is hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

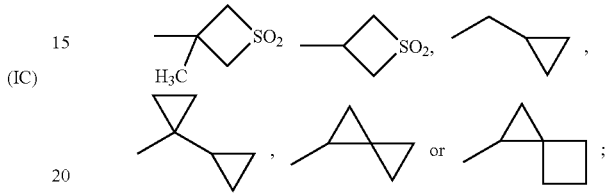

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

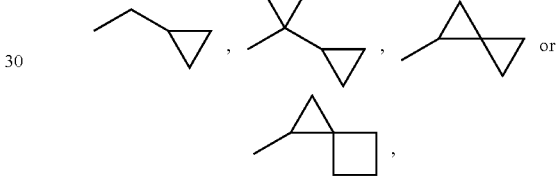

especially methyl and isopropyl; and
$R_{100}$ is halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$haloalkoxy; in particular trifluoromethyl, difluoromethyl, methoxy, bromo, chloro or 1,1,1-trifluoroethoxy.

For example, embodiment E1 is represented by the compounds of formula T1

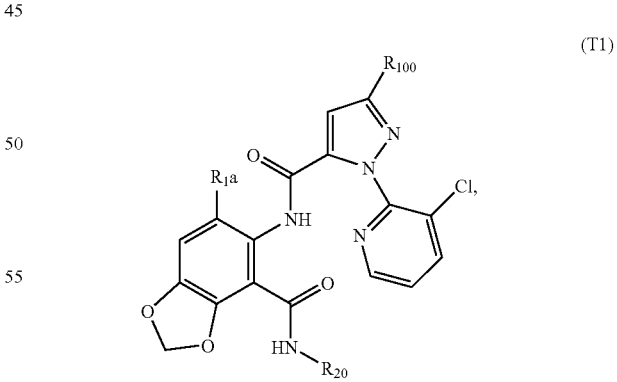

(T1)

wherein
$R_{1a}$ is hydrogen, $C_1$-$C_4$alkyl, $C_2$-$C_4$alkynyl, halogen or cyano; in particular chloro or methyl; $R_{20}$ is hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl, thiethan-3-yl, thiethan-3-yl substituted by $C_1$-$C_4$alkyl, preferably 3-methyl-thietan-3-yl,

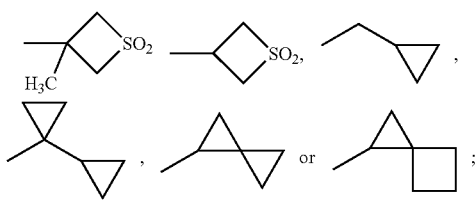

in particular hydrogen, $C_1$-$C_6$alkyl, $C_1$-$C_6$alkylthio-$C_1$-$C_6$alkyl, $C_1$-$C_6$alkylsulfonyl-$C_1$-$C_6$alkyl, $C_1$-$C_6$alkylsulfinyl-$C_1$-$C_6$alkyl,

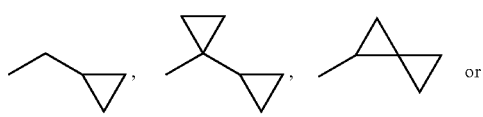

-continued especially methyl and isopropyl; and $R_{100}$ is halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkyl, $C_1$-$C_6$haloalkyl or $C_1$-$C_6$haloalkoxy; in particular trifluoromethyl, difluoromethyl, methoxy, bromo, chloro or 1,1,1-trifluoroethoxy.

Embodiments E2 to E55 are defined accordingly.

The process according to the invention for preparing compounds of the formula I is carried out analogously to known processes, for example as described in described, for example, in US 2003/0229050 and WO 2005/085234.

The general preparation of the compounds of formula I is illustrated in the following reaction schemes:

Reaction Scheme 1: Preparation of Compounds of Formula I:

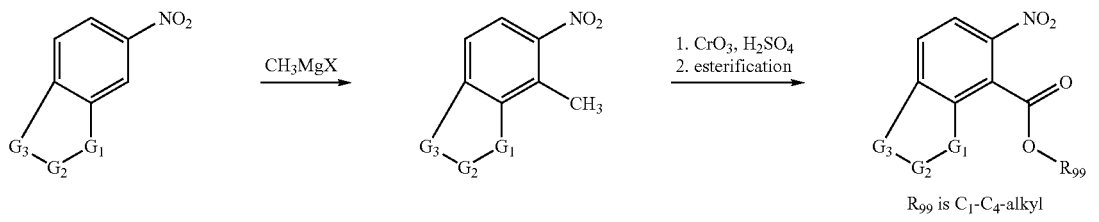

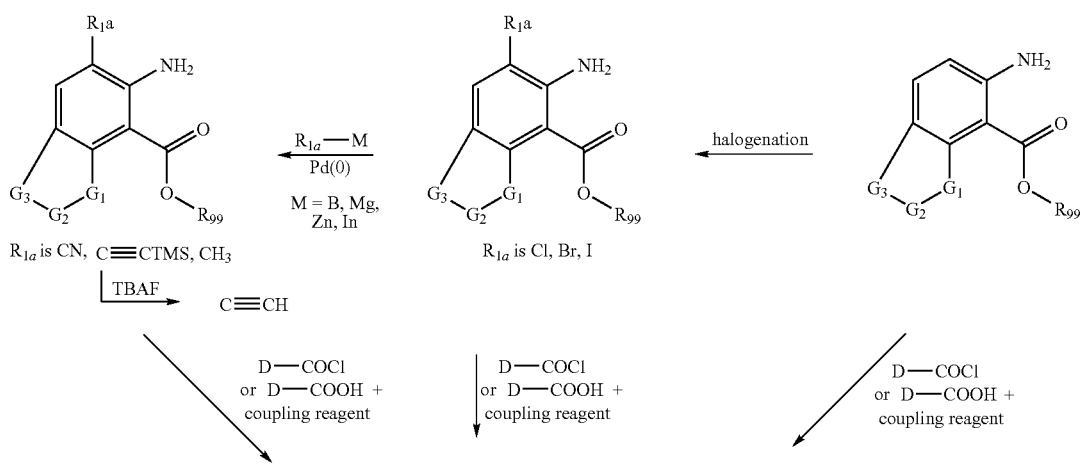

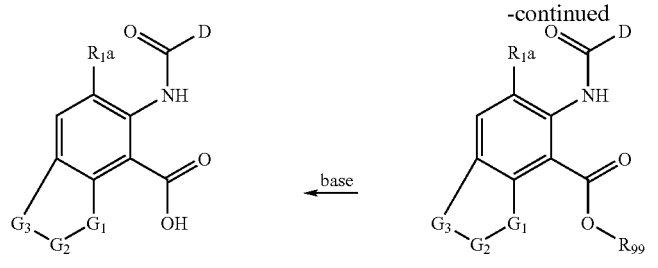
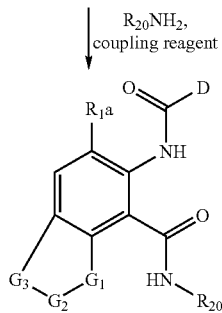
Reaction Scheme 2: Preparation of Compounds of Formula I:
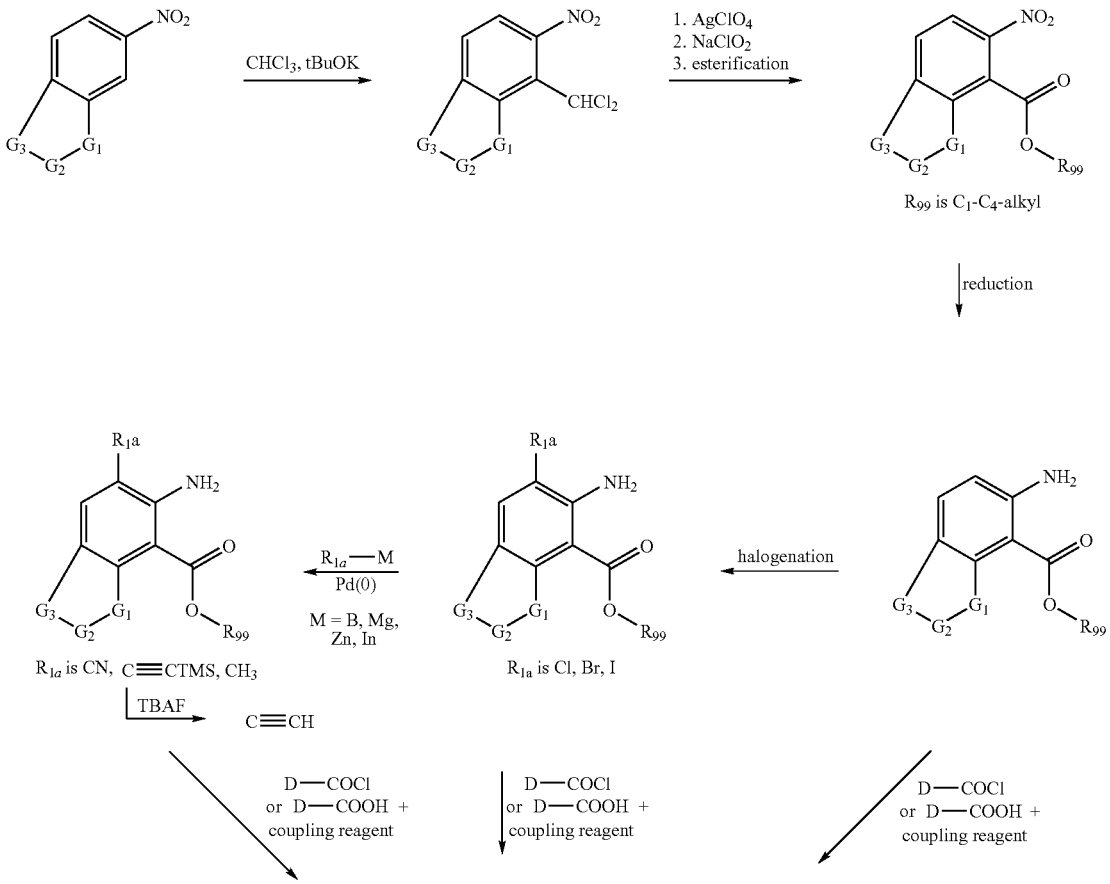

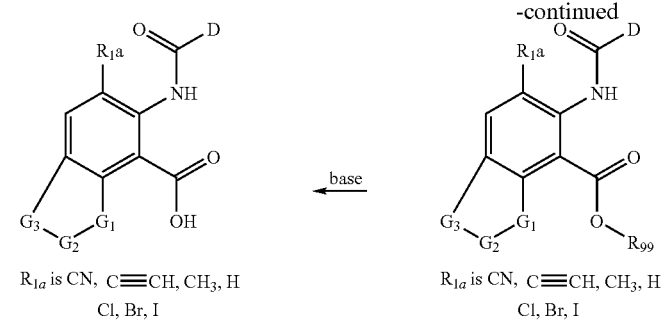
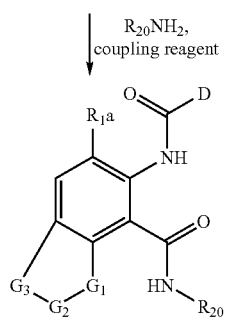
Reaction Scheme 3: Preparation of Compounds of Formula I:
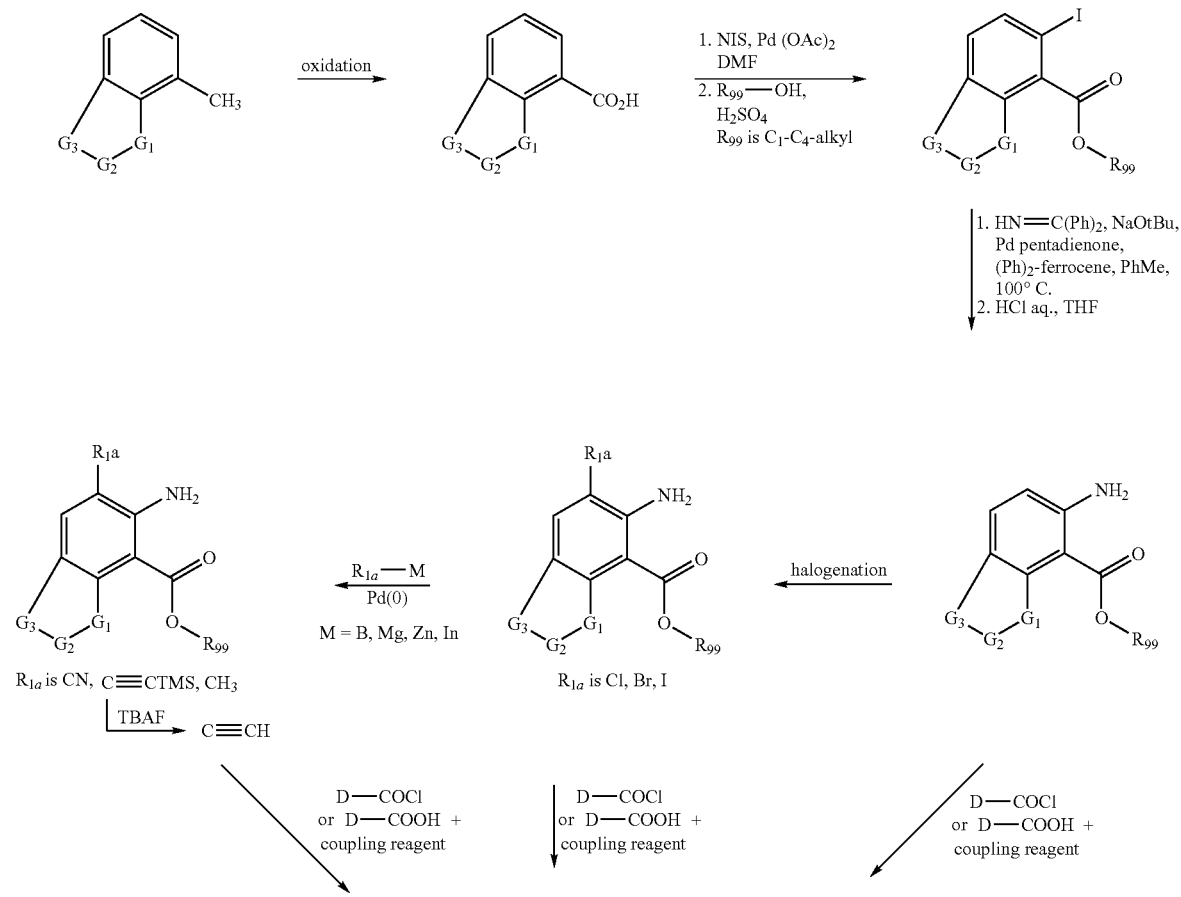

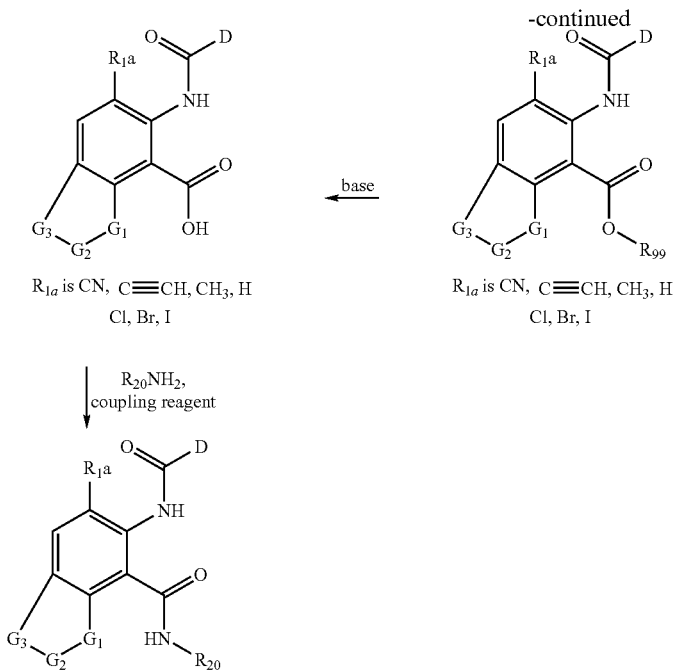
Reaction Scheme 4: Preparation of Compounds of Formula I:
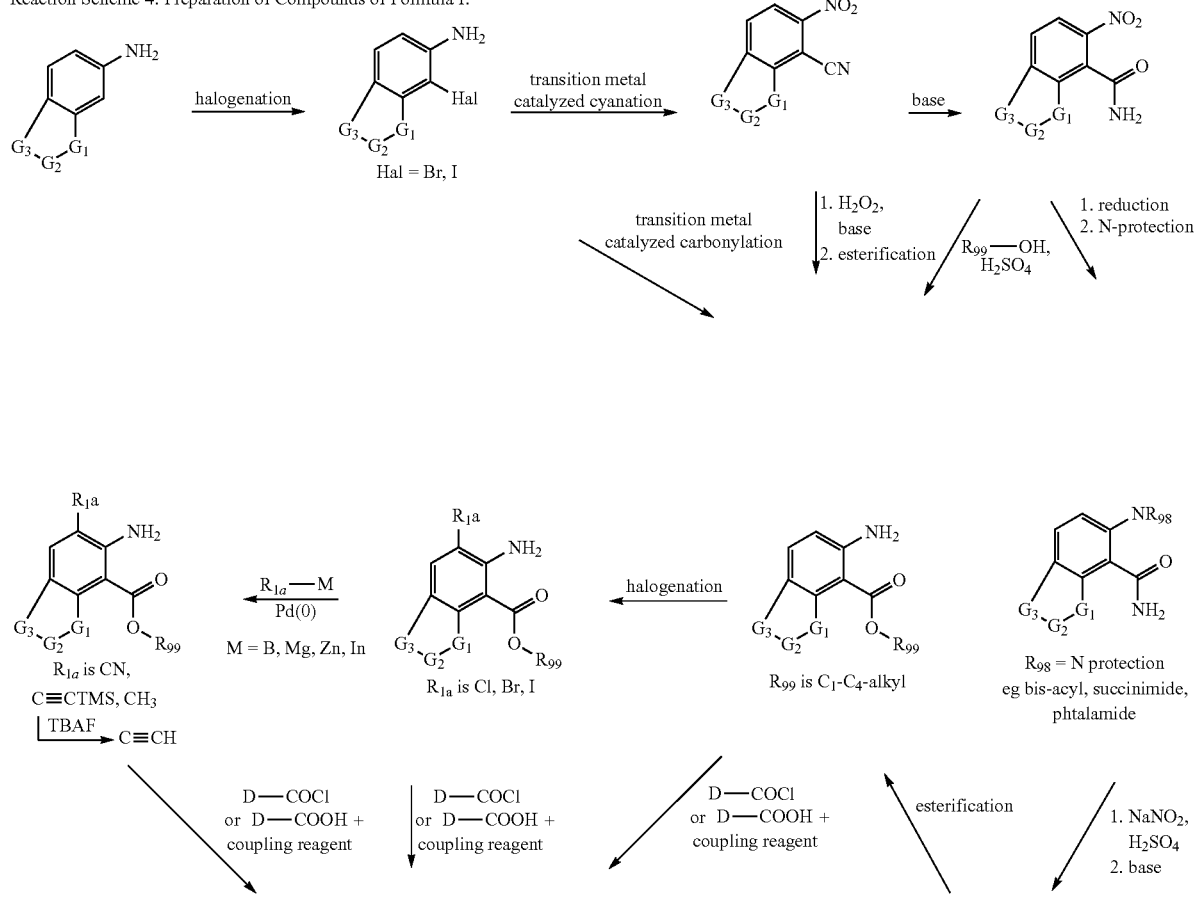

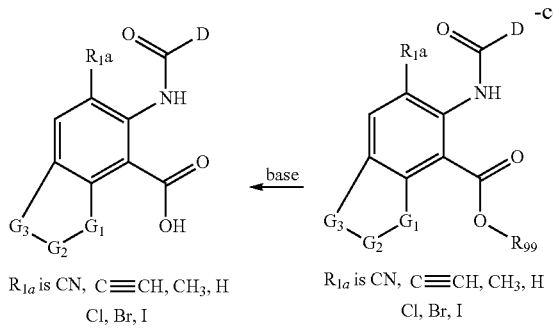
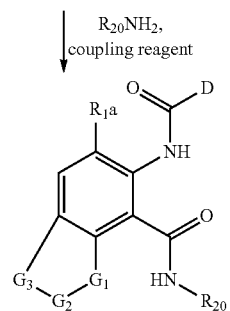
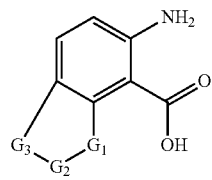
Reaction Scheme 5: Preparation of Compound of Formula I:
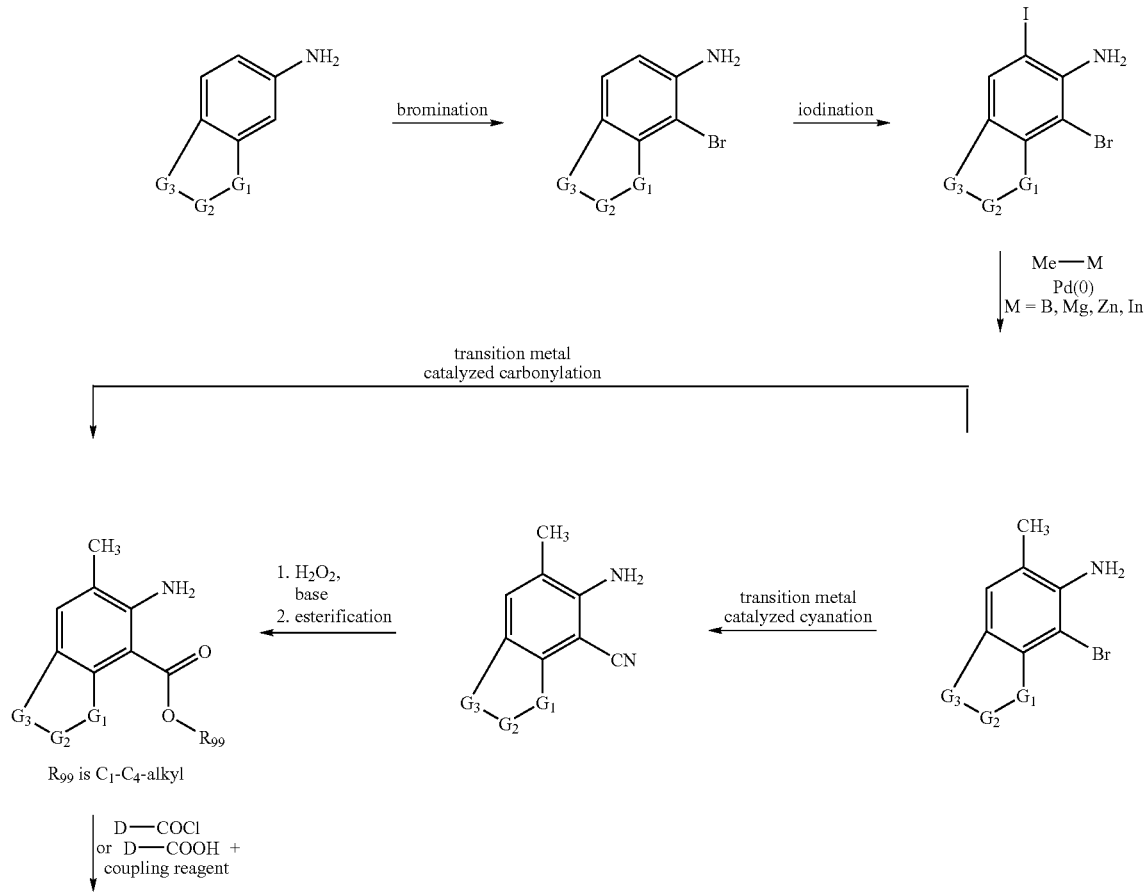

23 24
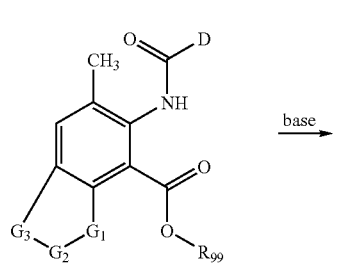 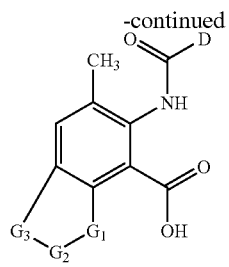 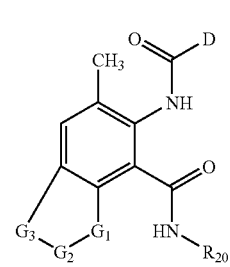
Reaction Scheme 6: Preparation of Compounds of Formula I
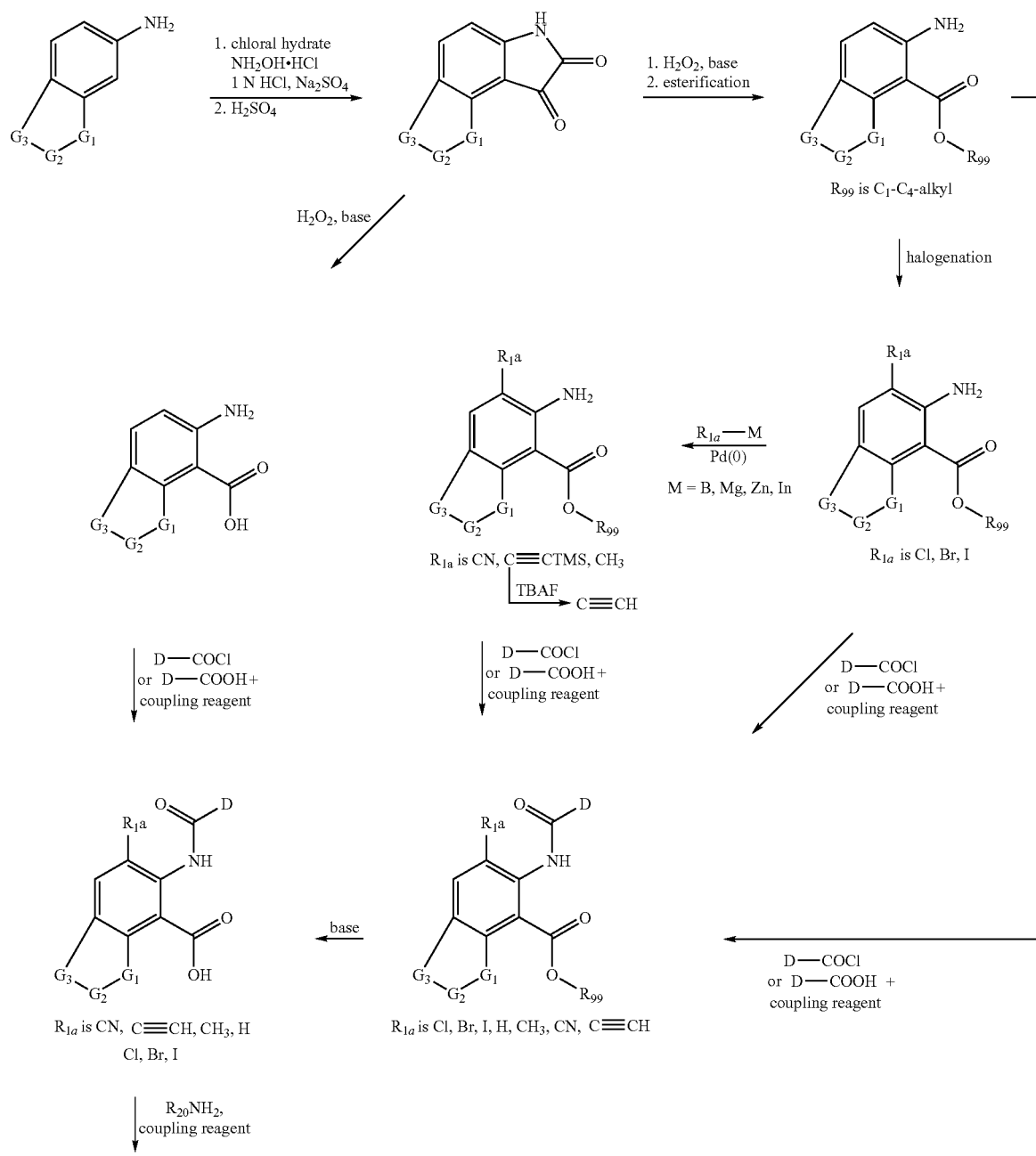

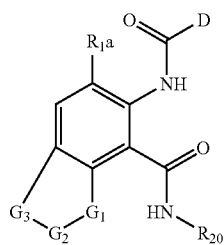
-continued
Reaction Scheme 7
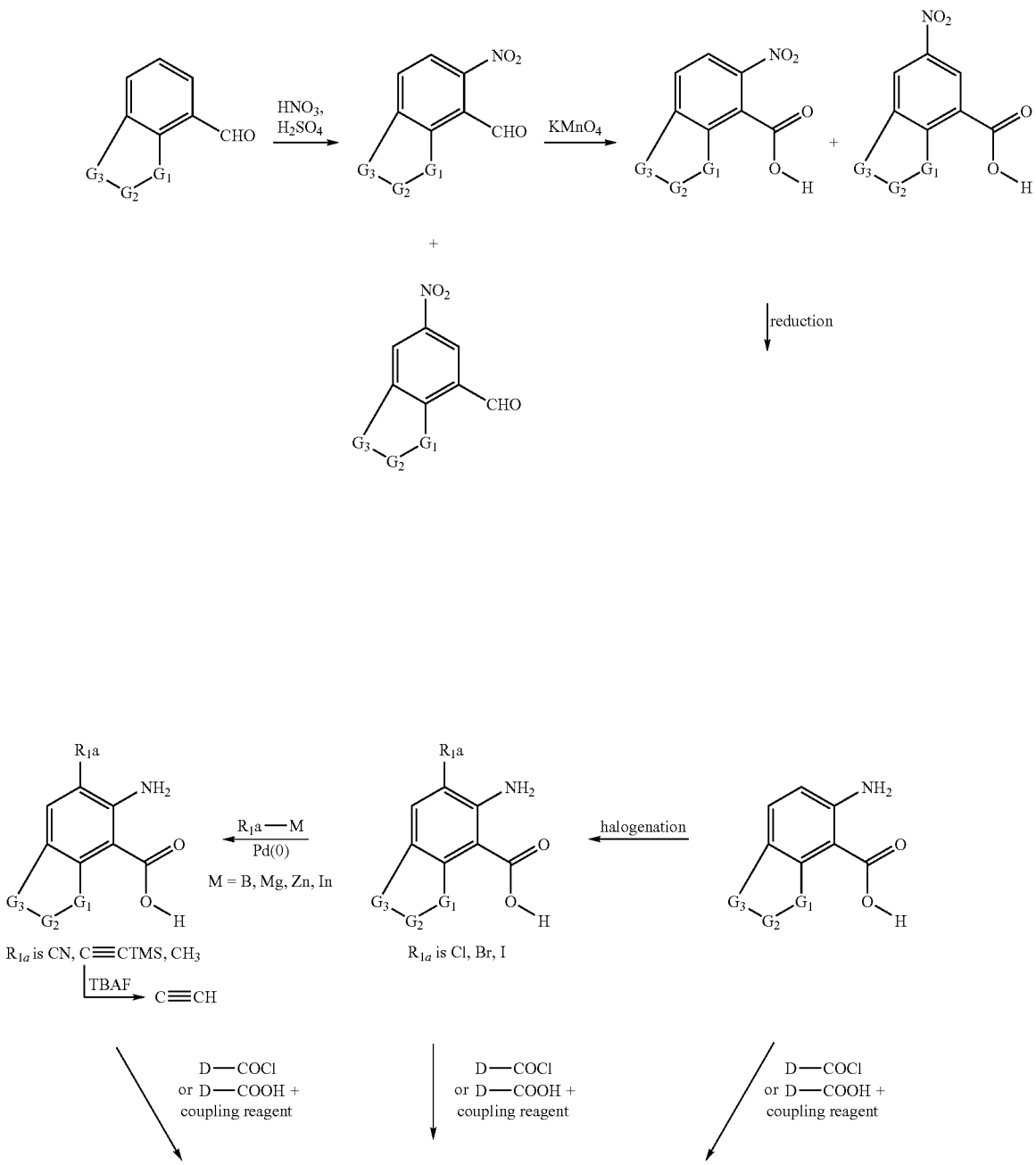

-continued
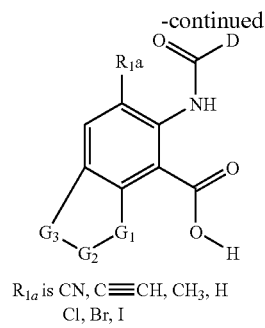
$R_{1a}$ is CN, C≡CH, CH$_3$, H
Cl, Br, I
↓ $R_{20}NH_2$, coupling reagent
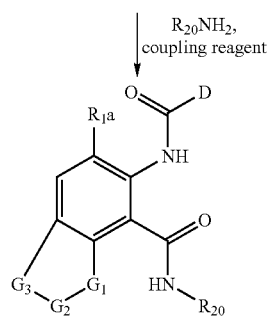
Reaction Scheme 8
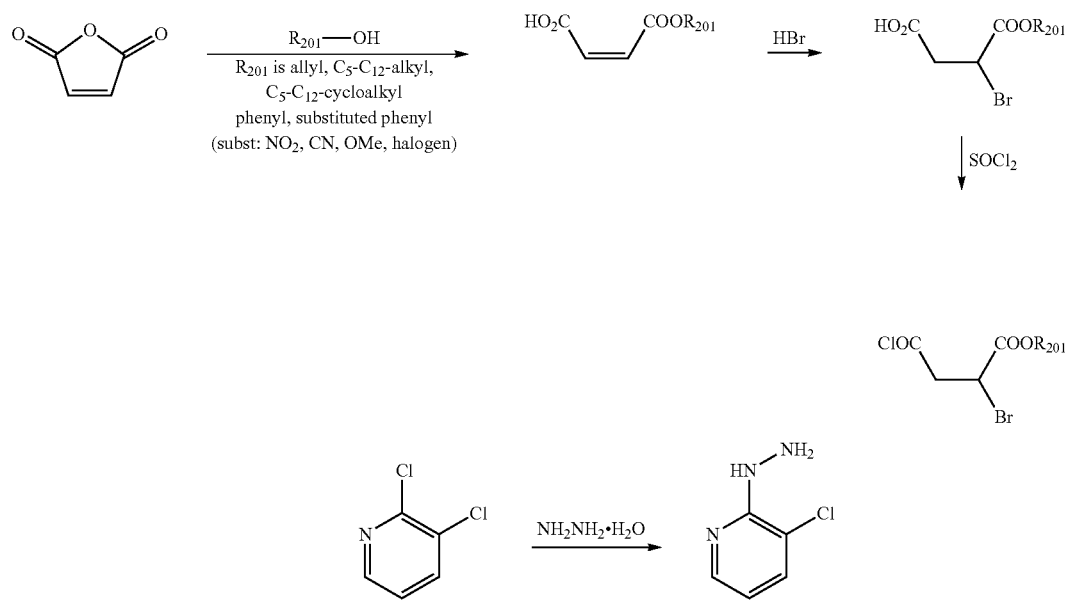

-continued
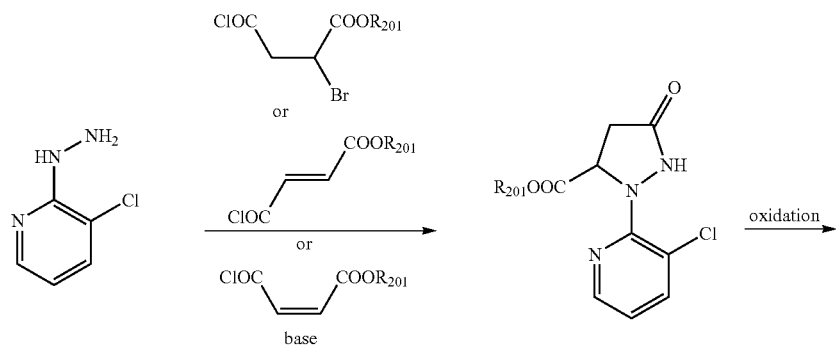
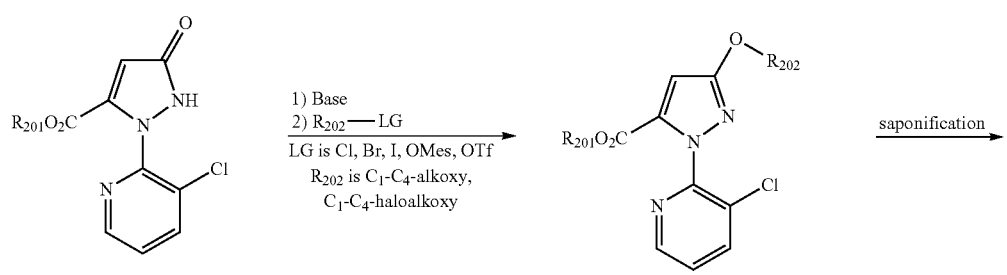
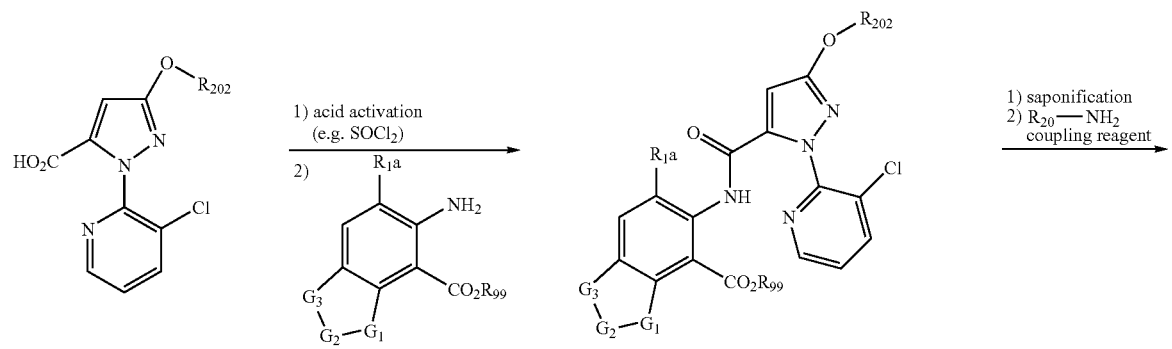
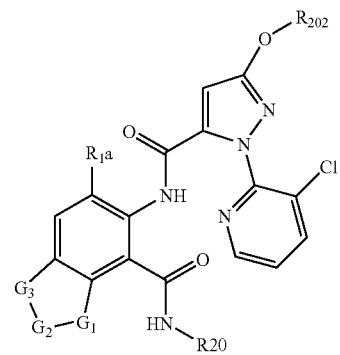

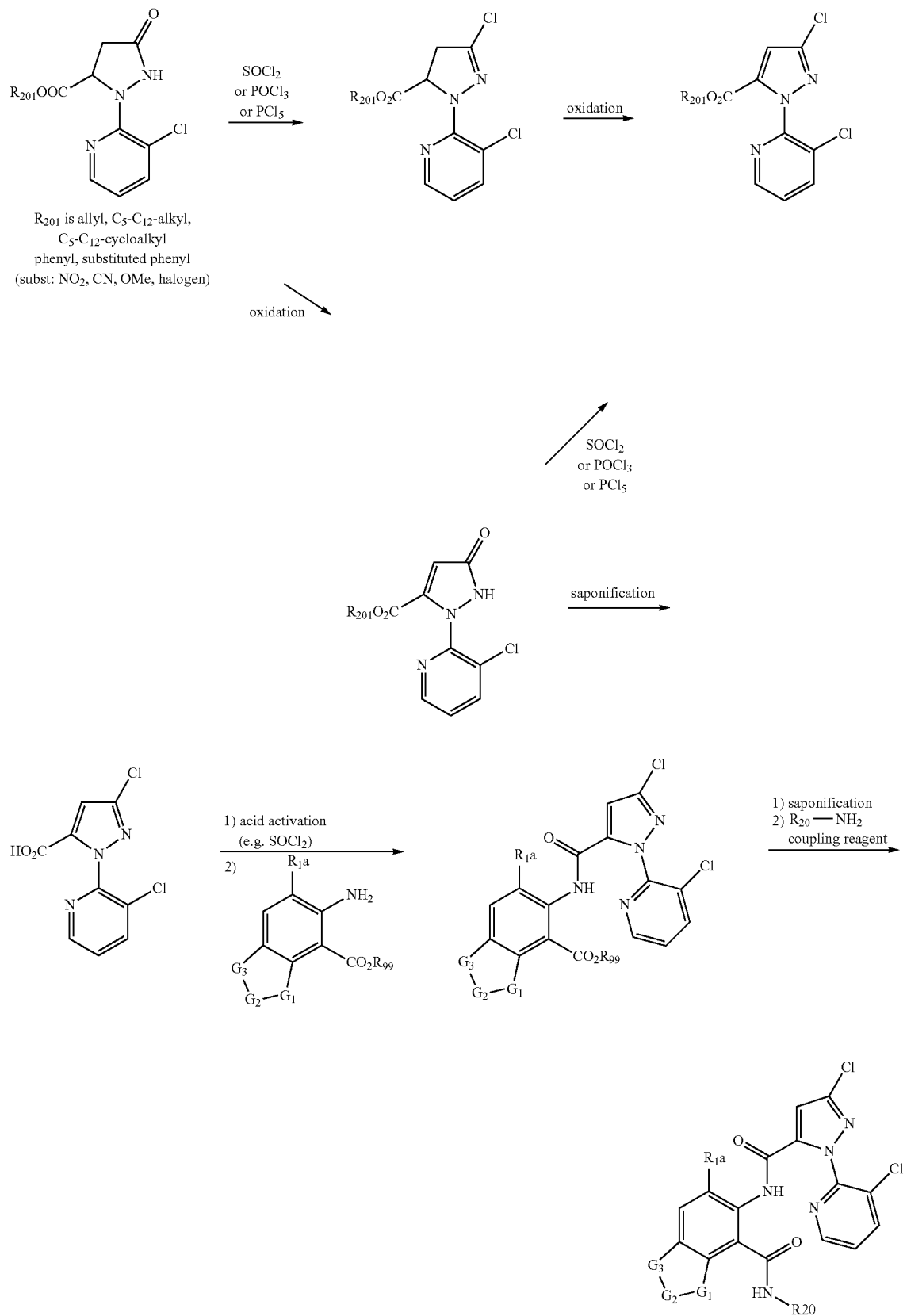
Reaction Scheme 9

Reaction Scheme 10
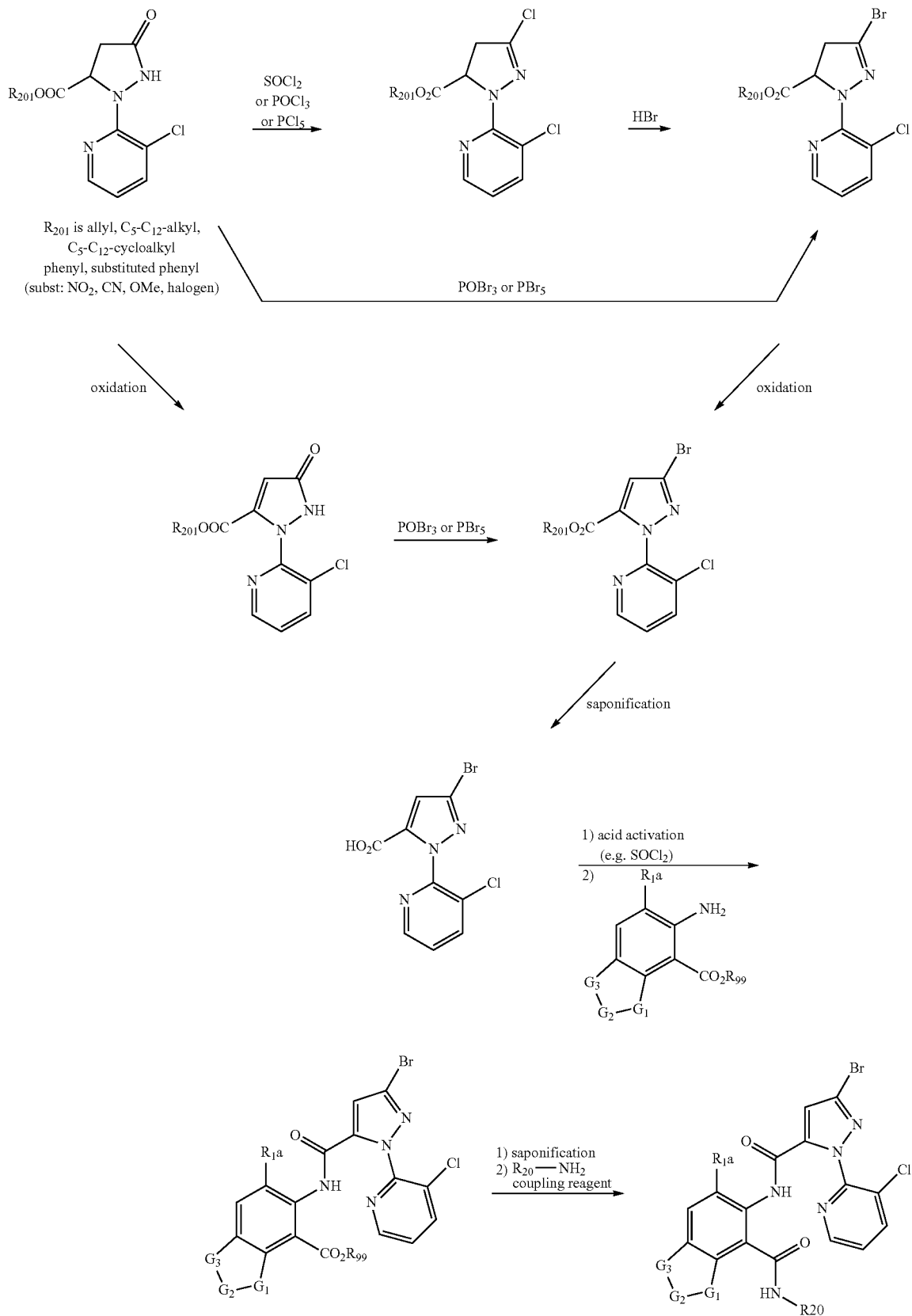

Reaction Scheme 11

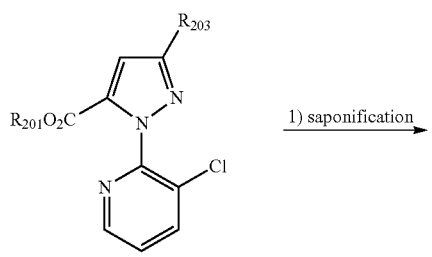

R$_{201}$ is allyl, C$_5$-C$_{12}$-alkyl,
C$_5$-C$_{12}$-cycloalkyl
phenyl, substituted phenyl
(subst: NO$_2$, CN, OMe, halogen)
R$_{203}$ = Cl, Br, CF$_3$, OR$_{202}$
R$_{202}$ is C$_1$-C$_4$-alkoxy,
C$_1$-C$_4$-haloalkoxy

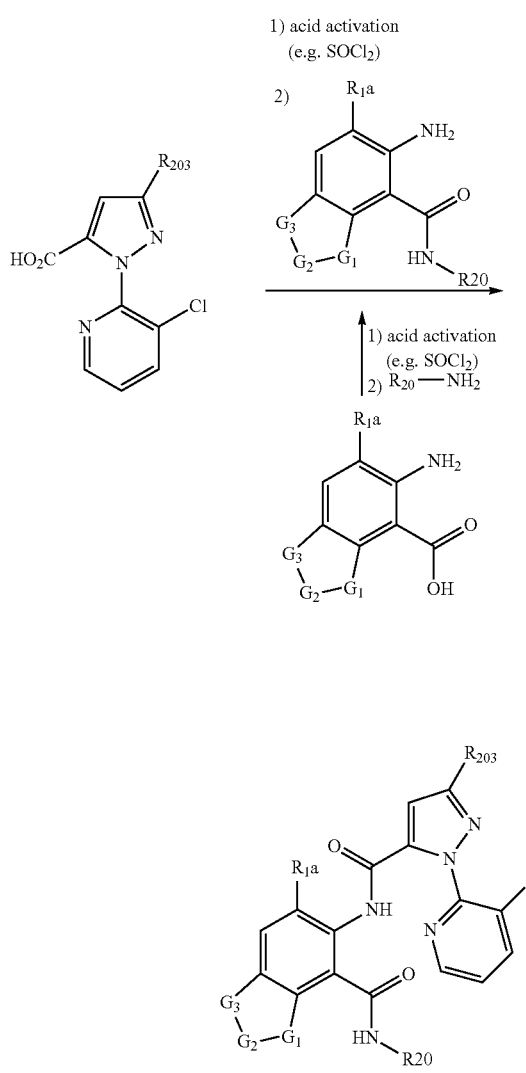

Intermediates of formula IIIa

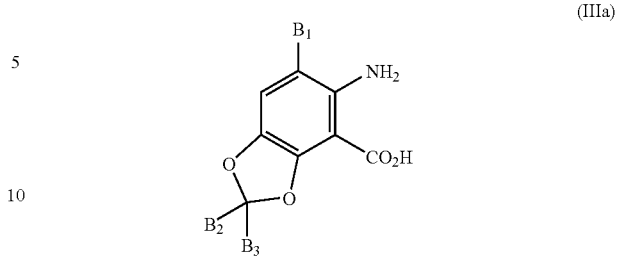
(IIIa)

where B$_1$ is H, Cl, Br, I or C1-6 alkyl and B$_2$ and B$_3$ are each independently H or F are novel. Examples of such compounds are given in Table B

TABLE B

| Anthranilic Acids Derivatives | Melting Point ° C. | LC-MS |
|---|---|---|
| (NH$_2$, CO$_2$H, F, F benzodioxole) | 204 | |
| (Cl, NH$_2$, CO$_2$H benzodioxole) | | 216/218 (M + 1)$^+$ |
| (Cl, NH$_2$, CO$_2$H, F, F benzodioxole) | 185-186 | |
| (Br, NH$_2$, CO$_2$H, F, F benzodioxole) | 199-201 | |
| (I, NH$_2$, CO$_2$H, F, F benzodioxole) | 174-175 | |

TABLE B-continued

| Anthranilic Acids Derivatives | Melting Point °C. | LC-MS |
|---|---|---|
| 6-methyl-5-amino, 4-CO2H benzodioxole with CF2 | >240 | — |
| 6-ethyl-5-amino, 4-CO2H benzodioxole with CF2 | >240 | — |
| 6-iodo-5-amino, 4-CO2Me benzodioxole | — | 326 |
| 6-methyl-5-N(Boc)2, 4-CO2Me benzodioxole | — | 521 |
| 6-methyl-5-amino, 4-CO2Me benzodioxole | — | 210 |

LC/MS data are obtained using a ZMD Mass Spectrometer from Waters (Single quadrupole mass spectrometer). Ionisation method: Electrospray; and HPLC from Agilent: quaternary HPLC pump HP1100, HP1100 Variable Wavelength Detector, HP1100 thermostatted column compartment and HP1100 solvent degasser. Eluents: A=water with 0.05% HCOOH, B=Acetonitril/Methanol (4:1, v/v)+0.04% HCOOH. Column: YMC-Pack ProC18, 3 micrometer particle size, 120 Angström, 33×3 mm.

TABLE C

| Intermediates | |
|---|---|
| | $R_{201}$ |
| C.1 | —$(CH_2)_4CH_3$ |
| C.2 | —$(CH_2)_5CH_3$ |
| C.3 | —$(CH_2)_6CH_3$ |
| C.4 | —$(CH_2)_7CH_3$ |
| C.5 | —$(CH_2)_8CH_3$ |
| C.6 | —$(CH_2)_9CH_3$ |
| C.7 | —$(CH_2)_{10}CH_3$ |
| C.8 | —$(CH_2)_{11}CH_3$ |
| C.9 | —$CH_2CH(CH_3)CH_2CH_3$ |
| C.10 | —$(CH_2)_2CH(CH_3)_2$ |
| C.11 | —$CH(CH_2CH_3)_2$ |
| C.12 | —$CH(CH_3)(CH_2)_2CH_3$ |
| C.13 | —$C(CH_3)_2CH_2CH_3$ |
| C.14 | —$CH_2C(CH_3)_3$ |
| C.15 | -cyclo-$C_6H_{11}$ |
| C.16 | —$CH_2CH{=}CH_2$ |
| C.17 | —$C_6H_5$ |
| C.18 | 4-nitrophenyl |
| C.19 | 2,4-dinitrophenyl (methyl-substituted) |
| C.20 | 2-nitrophenyl (methyl-substituted) |
| C.21 | pentafluorophenyl (methyl-substituted) |

Table C1: This table discloses the 21 compounds C1.1 to C1.21 of the formula TC1

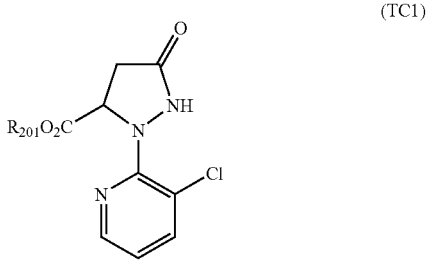

(TC1)

in which, for each of these 21 specific compounds, the variable $R_{201}$ has the specific meaning given in the corresponding line, appropriately selected from the 21 lines C.1.1 to C.1.21 of the Table C. The compounds of formula TC1, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C2: This table discloses the 21 compounds C2.1 to C2.21 of the formula TC2

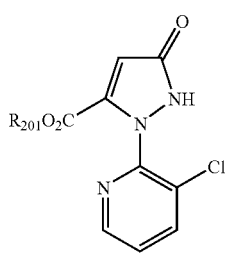
(TC2)

in which, for each of these 21 specific compounds, the variable $R_{201}$ has the specific meaning given in the corresponding line, appropriately selected from the 21 lines C.2.1 to C.2.21 of the table C. The compounds of formula TC2, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C3: This table discloses the 21 compounds C3.1 to C3.21 of the formula TC3

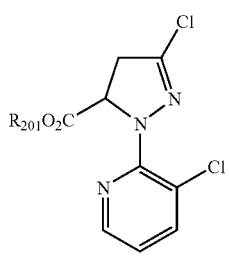
(TC3)

in which, for each of these 21 specific compounds, the variable $R_{201}$ has the specific meaning given in the corresponding line, appropriately selected from the 21 lines C.3.1 to C.3.21 of the table C. The compounds of formula TC3, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C4: This table discloses the 21 compounds C4.1 to C4.21 of the formula TC4

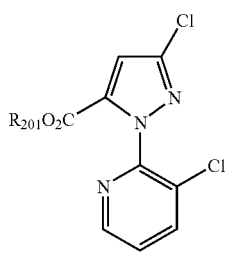
(TC4)

in which, for each of these 21 specific compounds, the variable $R_{201}$ has the specific meaning given in the corresponding line, appropriately selected from the 21 lines C.4.1 to C.4.21 of the table C. The compounds of formula TC4, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C5: This table discloses the 21 compounds C5.1 to C5.21 of the formula TC5

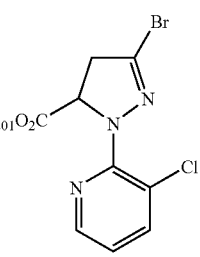
(TC5)

in which, for each of these 21 specific compounds, the variable $R_{201}$ has the specific meaning given in the corresponding line, appropriately selected from the 21 lines C.5.1 to C.5.21 of the table C. The compounds of formula TC5, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C6: This table discloses the 21 compounds C6.1 to C6.21 of the formula TC6

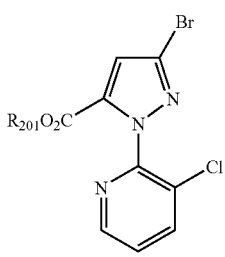
(TC6)

in which, for each of these 21 specific compounds, the variable $R_{201}$ has the specific meaning given in the corresponding line, appropriately selected from the 21 lines C.6.1 to C.6.21 of the table C. The compounds of formula TC6, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C7: This table discloses the 21 compounds C7.1 to C7.21 of the formula TC7

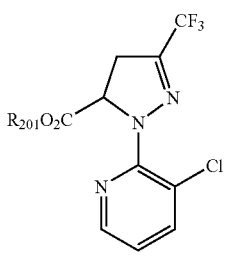
(TC7)

in which, for each of these 21 specific compounds, the variable $R_{201}$ has the specific meaning given in the corresponding line, appropriately selected from the 21 lines C.7.1 to C.7.21 of the table C. The compounds of formula TC7, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C8: This table discloses the 21 compounds C8.1 to C8.21 of the formula TC8

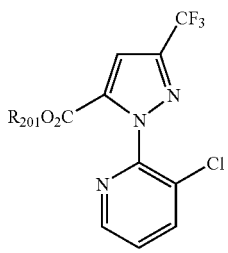
(TC8)

in which, for each of these 21 specific compounds, the variable $R_{201}$ has the specific meaning given in the corresponding line, appropriately selected from the 21 lines C.8.1 to C.8.21 of the table C. The compounds of formula TC8, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C9: This table discloses the 21 compounds C9.1 to C9.21 of the formula TC9

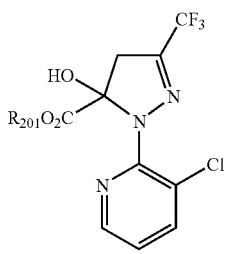
(TC9)

in which, for each of these 21 specific compounds, the variable $R_{201}$ has the specific meaning given in the corresponding line, appropriately selected from the 21 lines C.9.1 to C.9.21 of the table C. The compounds of formula TC9, wherein $R_{201}$ is $C_5$-$C_{12}$alkyl, cyclohexyl, allyl, pentafluorophenyl, 2-nitrophenyl, 4-nitrophenyl or 2,4-dinitrophenyl are novel and as such form a further aspect of the invention.

Table C10: This table discloses the 21 compounds C10.1 to C10.21 of the formula TC10

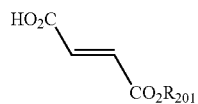
(TC10)

in which, for each of these 21 specific compounds, the variable $R_{201}$ has the specific meaning given in the corresponding line, appropriately selected from the 21 lines C.10.1 to C.10.21 of the table C.

Table C11: This table discloses the 21 compounds C11.1 to C11.21 of the formula TC11

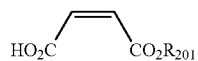
(TC11)

in which, for each of these 21 specific compounds, the variable $R_{201}$ has the specific meaning given in the corresponding line, appropriately selected from the 21 lines C.11.1 to C.11.21 of the table C.

Table C12: This table discloses the 21 compounds C12.1 to C12.21 of the formula TC12

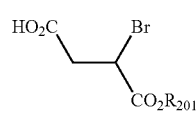
(TC12)

in which, for each of these 21 specific compounds, the variable R201 has the specific meaning given in the corresponding line, appropriately selected from the 21 lines C.12.1 to C.12.21 of the table C. Certain compounds of Table C12 are novel and as such form a further aspect of the invention. Compounds C12.4, C12.6, C12.8, C12.16 and C12.18 are known compounds.

Table C13: This table discloses the 21 compounds C13.1 to C13.21 of the formula TC13

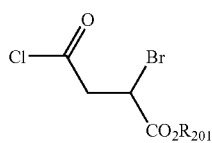
(TC13)

in which, for each of these 21 specific compounds, the variable $R_{201}$ has the specific meaning given in the corresponding line, appropriately selected from the 21 lines C.13.1 to C.13.21 of the table C. The compounds of Table C13 are novel and as such form a further aspect of the invention.

TABLE D

| | Intermediates | |
|---|---|---|
| | $R_{201}$ | $R_{202}$ |
| D.1 | —$(CH_2)_4CH_3$ | $CH_3$ |
| D.2 | —$(CH_2)_5CH_3$ | $CH_3$ |
| D.3 | —$(CH_2)_6CH_3$ | $CH_3$ |
| D.4 | —$(CH_2)_7CH_3$ | $CH_3$ |
| D.5 | —$(CH_2)_8CH_3$ | $CH_3$ |
| D.6 | —$(CH_2)_9CH_3$ | $CH_3$ |
| D.7 | —$(CH_2)_{10}CH_3$ | $CH_3$ |
| D.8 | —$(CH_2)_{11}CH_3$ | $CH_3$ |
| D.9 | —$CH_2CH(CH_3)CH_2CH_3$ | $CH_3$ |
| D.10 | —$(CH_2)_2CH(CH_3)_2$ | $CH_3$ |
| D.11 | —$CH(CH_2CH_3)_2$ | $CH_3$ |
| D.12 | —$CH(CH_3)(CH_2)_2CH_3$ | $CH_3$ |
| D.13 | —$C(CH_3)_2CH_2CH_3$ | $CH_3$ |
| D.14 | —$CH_2C(CH_3)_3$ | $CH_3$ |
| D.15 | -cyclo-$C_6H_{11}$ | $CH_3$ |
| D.16 | —$CH_2CH{=}CH_2$ | $CH_3$ |
| D.17 | —$C_6H_5$ | $CH_3$ |
| D.18 | —C₆H₄—NO₂ (para) | $CH_3$ |
| D.19 | —C₆H₃(NO₂)₂ (2,4-dinitro) | $CH_3$ |

TABLE D-continued

Intermediates

| | $R_{201}$ | $R_{202}$ |
|---|---|---|
| D.20 | 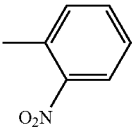 2-nitrophenyl (with methyl) | $CH_3$ |
| D.21 | 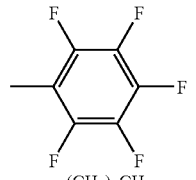 pentafluorophenyl (with methyl) | $CH_3$ |
| D.22 | —$(CH_2)_4CH_3$ | $CF_3$ |
| D.23 | —$(CH_2)_5CH_3$ | $CF_3$ |
| D.24 | —$(CH_2)_6CH_3$ | $CF_3$ |
| D.25 | —$(CH_2)_7CH_3$ | $CF_3$ |
| D.26 | —$(CH_2)_8CH_3$ | $CF_3$ |
| D.27 | —$(CH_2)_9CH_3$ | $CF_3$ |
| D.28 | —$(CH_2)_{10}CH_3$ | $CF_3$ |
| D.29 | —$(CH_2)_{11}CH_3$ | $CF_3$ |
| D.30 | —$CH_2CH(CH_3)CH_2CH_3$ | $CF_3$ |
| D.31 | —$(CH_2)_2CH(CH_3)_2$ | $CF_3$ |
| D.32 | —$CH(CH_2CH_3)_2$ | $CF_3$ |
| D.33 | —$CH(CH_3)(CH_2)_2CH_3$ | $CF_3$ |
| D.34 | —$C(CH_3)_2CH_2CH_3$ | $CF_3$ |
| D.35 | —$CH_2C(CH_3)_3$ | $CF_3$ |
| D.36 | -cyclo-$C_6H_{11}$ | $CF_3$ |
| D.37 | —$CH_2CH$=$CH_2$ | $CF_3$ |
| D.38 | —$C_6H_5$ | $CF_3$ |
| D.39 | 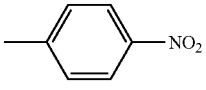 4-nitrophenyl | $CF_3$ |
| D.40 | 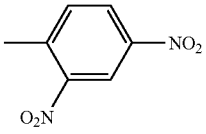 2,4-dinitrophenyl | $CF_3$ |
| D.41 | 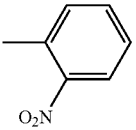 2-nitrophenyl | $CF_3$ |
| D.42 | 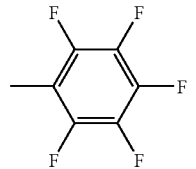 pentafluorophenyl | $CF_3$ |
| D.43 | —$(CH_2)_4CH_3$ | $CH_2CF_3$ |
| D.44 | —$(CH_2)_5CH_3$ | $CH_2CF_3$ |
| D.45 | —$(CH_2)_6CH_3$ | $CH_2CF_3$ |
| D.46 | —$(CH_2)_7CH_3$ | $CH_2CF_3$ |
| D.47 | —$(CH_2)_8CH_3$ | $CH_2CF_3$ |
| D.48 | —$(CH_2)_9CH_3$ | $CH_2CF_3$ |
| D.49 | —$(CH_2)_{10}CH_3$ | $CH_2CF_3$ |
| D.50 | —$(CH_2)_{11}CH_3$ | $CH_2CF_3$ |
| D.51 | —$CH_2CH(CH_3)CH_2CH_3$ | $CH_2CF_3$ |
| D.52 | —$(CH_2)_2CH(CH_3)_2$ | $CH_2CF_3$ |
| D.53 | —$CH(CH_2CH_3)_2$ | $CH_2CF_3$ |
| D.54 | —$CH(CH_3)(CH_2)_2CH_3$ | $CH_2CF_3$ |
| D.55 | —$C(CH_3)_2CH_2CH_3$ | $CH_2CF_3$ |
| D.56 | —$CH_2C(CH_3)_3$ | $CH_2CF_3$ |
| D.57 | -cyclo-$C_6H_{11}$ | $CH_2CF_3$ |
| D.58 | —$CH_2CH$=$CH_2$ | $CH_2CF_3$ |
| D.59 | —$C_6H_5$ | $CH_2CF_3$ |
| D.60 | 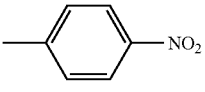 4-nitrophenyl | $CH_2CF_3$ |
| D.61 | 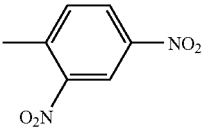 2,4-dinitrophenyl | $CH_2CF_3$ |
| D.62 | 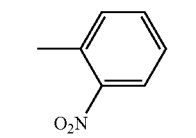 2-nitrophenyl | $CH_2CF_3$ |
| D.63 | 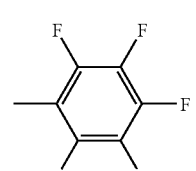 pentafluorophenyl | $CH_2CF_3$ |
| D.64 | —$(CH_2)_4CH_3$ | $CF_2H$ |
| D.65 | —$(CH_2)_5CH_3$ | $CF_2H$ |
| D.66 | —$(CH_2)_6CH_3$ | $CF_2H$ |
| D.67 | —$(CH_2)_7CH_3$ | $CF_2H$ |
| D.68 | —$(CH_2)_8CH_3$ | $CF_2H$ |
| D.69 | —$(CH_2)_9CH_3$ | $CF_2H$ |
| D.70 | —$(CH_2)_{10}CH_3$ | $CF_2H$ |
| D.71 | —$(CH_2)_{11}CH_3$ | $CF_2H$ |
| D.72 | —$CH_2CH(CH_3)CH_2CH_3$ | $CF_2H$ |
| D.73 | —$(CH_2)_2CH(CH_3)_2$ | $CF_2H$ |
| D.74 | —$CH(CH_2CH_3)_2$ | $CF_2H$ |
| D.75 | —$CH(CH_3)(CH_2)_2CH_3$ | $CF_2H$ |
| D.76 | —$C(CH_3)_2CH_2CH_3$ | $CF_2H$ |
| D.77 | —$CH_2C(CH_3)_3$ | $CF_2H$ |
| D.78 | -cyclo-$C_6H_{11}$ | $CF_2H$ |
| D.79 | —$CH_2CH$=$CH_2$ | $CF_2H$ |
| D.80 | —$C_6H_5$ | $CF_2H$ |
| D.81 | 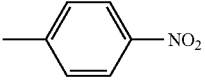 4-nitrophenyl | $CF_2H$ |
| D.82 | 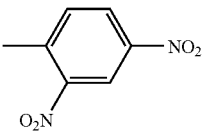 2,4-dinitrophenyl | $CF_2H$ |
| D.83 | 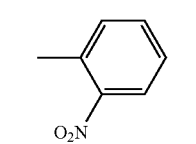 2-nitrophenyl | $CF_2H$ |

TABLE D-continued

Intermediates

| | $R_{201}$ | $R_{202}$ |
|---|---|---|
| D.84 | 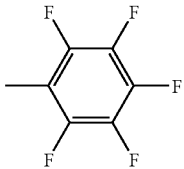 | $CF_2H$ |

Table D1: This table discloses the 84 compounds D1.1 to D1.84 of the formula TD1

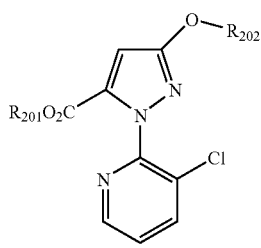
(TD1)

in which, for each of these 84 specific compounds, each of the of the variables $R_{201}$ and $R_{202}$ has the specific meaning given in the corresponding line, appropriately selected from the 84 lines D.1.1 to D.1.84 of the Table D.

TABLE E

Intermediates

| | $R_{202}$ |
|---|---|
| E.1 | $OCH_3$ |
| E.2 | $OCF_3$ |
| E.3 | $OCH_2CF_3$ |
| E.4 | $OCF_2H$ |

Table E1: This table discloses the 4 compounds E1.1 to E1.4 of the formula TE1

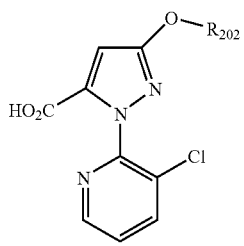
(TE1)

in which, for each of these 4 specific compounds, the variable $R_{202}$ has the specific meaning given in the corresponding line, appropriately selected from the 4 lines E.1.1 to E.1.4 of the Table E.

Certain intermediates of formula II and III are novel and as such form another aspect of the invention.

In particular compounds of formula II

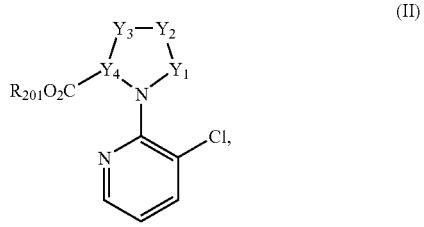
(II)

wherein $Y_1$ is NH or =N;
$Y_2$ is C=O, =C—Cl, =C—Br, =C—$CF_3$ or =C—$OR_{202}$;
$R_{202}$ is $CH_3$, $CF_3$, $CH_2CF_3$ or $CF_2H$;
$Y_3$ is $CH_2$ or =CH;
$Y_4$ is =C, CH or C—OH and
$R_{201}$ is $C_5$-$C_{12}$alkyl, cyclohexyl, allyl, pentafluorophenyl, 2-nitrophenyl, 4-nitrophenyl or 2,4-dinitrophenyl and compounds of formula III

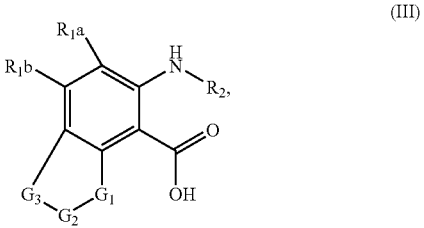
(III)

where $R_{1a}$, $R_{1b}$, $G_1$, $G_2$, $G_3$ and $R_2$ are as define above.

The starting compounds and intermediates of the reaction schemes are known or can be prepared according to methods known to a person skilled in the art.

The reactants can be reacted in the presence of a base. Examples of suitable bases are alkali metal or alkaline earth metal hydroxides, alkali metal or alkaline earth metal hydrides, to alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140°

C., preferably from approximately −30° C. to approximately +100° C., in many cases in the range between ambient temperature and approximately +80° C.

A compound I can be converted in a manner known per se into another compound I by replacing one or more substituents of the starting compound I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds I can be prepared in a manner known per se. Thus, for example, acid addition salts of compounds I are obtained by treatment with a suitable acid or a suitable ion exchanger reagent and salts with bases are obtained by treatment with a suitable base or with a suitable ion exchanger reagent.

Salts of compounds I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds I can be converted in a manner known per se into other salts of compounds I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds I, which have salt-forming properties can be obtained in free form or in the form of salts.

The compounds I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemLineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;

from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahlbergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri;*
from the order Hymenoptera, for example,
*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order *Mallophaga*, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Frankliniella* spp., *Hercinothrips* spp., *Scirtothrips aurantii, Taeniothrips* spp., *Thrips palmi* and *Thrips tabaci*; and
from the order Thysanura, for example, *Lepisma saccharina*.

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A;

or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are Generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton to variety that expresses a CryIA(c) and a CryIIA(b) toxin); VIPCOT® (cotton variety that expresses a VIP toxin); NewLeaf® (potato variety that expresses a CryIIIA toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/N000/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compositions according to the invention are active against ectoparasites such as hard ticks, soft ticks, mange mites, harvest mites, flies (biting and licking), parasitic fly larvae, lice, hair lice, bird lice and fleas. Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable Concentrates:

| active ingredient: | 1 to 95%, preferably 5 to 20% |
| surfactant: | 1 to 30%, preferably 10 to 20% |
| solvent: | 5 to 98%, preferably 70 to 85% |

Dusts:

| active ingredient: | 0.1 to 10%, preferably 0.1 to 1% |
| solid carrier: | 99.9 to 90%, preferably 99.9 to 99% |

Suspension Concentrates:

| active ingredient: | 5 to 75%, preferably 10 to 50% |
| water: | 94 to 24%, preferably 88 to 30% |
| surfactant: | 1 to 40%, preferably 2 to 30% |

Wettable Powders:

| active ingredient: | 0.5 to 90%, preferably 1 to 80% |
| surfactant: | 0.5 to 20%, preferably 1 to 15% |
| solid carrier: | 5 to 99%, preferably 15 to 98% |

Granulates:

| active ingredient: | 0.5 to 30%, preferably 3 to 15% |
| solid carrier: | 99.5 to 70%, preferably 97 to 85% |

PREPARATORY EXAMPLES

Example 1

Preparation of 5-chloro-6-{[2-(3-chloro-pyridin-2-yl)-5-trifluoromethyl-2H-pyrazole-3-carbonyl]-amino}-2,4-dioxolane-benzoic acid isopropylamide a) Preparation of

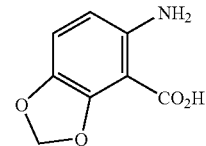

This compound is prepared as described in *J. Med. Chem.*, 1979, 22, 1355.

b) Preparation of

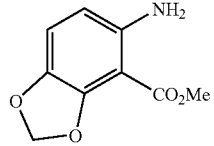 [SMILES: COC(=O)c1c(N)ccc2c1OCO2]

A solution of 5,6-dioxolane-2-nitrobenzoic acid (50 g, 0.23 mol) in N,N-dimethylformamide (500 ml) is treated with cesium carbonate (92 g, 0.23 mol), heated to 40° C., treated with methyl iodide (49 g, 0.34 mol), stirred for one hour, cooled to ambient temperature, and filtered. The filtrate is concentrated to about 10 ml, diluted with ethyl acetate, and washed with water. The combined organic layers are dried over sodium sulphate, filtered, and evaporated to give methyl 5,6-dioxolane-2-nitrobenzoate (50 g, 94%).

A solution of 5,6-dioxolane-2-nitrobenzoate (7.2 g, 32 mmol) in methanol/water 1:1 (500 ml) is treated with 20 g of iron powder, heated at 55° C., and treated with ammonium chloride (55.2 g, 32.2 mmol) in portions over 6 hours. The mixture is filtered through Celite, concentrated to ca. half the volume, and extracted with ethylacetate. Organic layer is separated, dried over sodium sulphate, filtered, and evaporated to give 3,4-dioxolane-anthranilic acid methyl ester (6 g, 96%); LC/MS: 196 (M+1)$^+$.

c) Preparation of

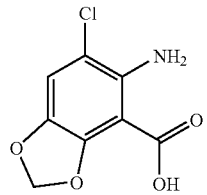

A solution of 3,4-dioxolane-anthranilic acid methyl ester (2 g, 10 mmol) in tetrahydrofuran (100 ml) is treated with N-chlorosuccinimide (1.4 g, 10.5 mmol) in portions over a period of 30 min and stirred for one hour. Tetrahydrofuran is evaporated and the residue is dissolved in ethylacetate. The solution is washed with water, dried over sodium sulphate, and filtered. Evaporation of solvent and purification by chromatography with ethylacetate/hexane (4:1) as eluent to afford 6-chloro-3,4-dioxolane-anthranilic acid methyl ester (1 g, 43%) as a solid.

A solution of 3,4-dioxolane-anthranilic acid methyl ester (1.3 g, 5.63 mmol) in acetonitrile/water 1:1 (30 ml) is treated with aqueous solution of sodium hydroxide (8.5 mmol) and stirred at 70° C. for 3 hours. The mixture is cooled to ambient temperature and washed with diethyl ether. Aqueous layer is acidified and extracted with ethyl acetate. Organic layer is then dried over sodium sulphate, filtered, and evaporated to give the product 6-chloro-3,4-dioxolane-anthranilic acid (1.1 g, 93%); LC/MS: 216/218 (M+1)$^+$.

d) Preparation of

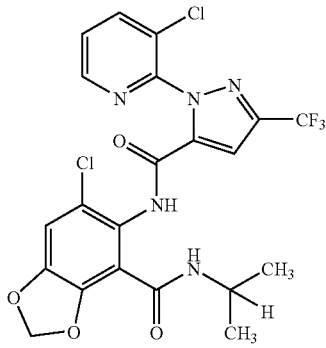 [SMILES: CC(C)NC(=O)c1c(NC(=O)c2cc(C(F)(F)F)nn2-c2ncccc2Cl)c(Cl)cc2c1OCO2]

To a mixture of 380 mg (1.3 mmol) of 2-(3-chloro-pyridin-2-yl)-5-trifluoromethyl-2H-pyrazole-3-carboxylic acid in 25 ml of acetonitrile is added 0.4 ml of pyridine and 300 mg (1.3 mmol) of 6-chloro-3,4-dioxolane-anthranilic acid. The mixture is cooled to 0-5° C. and to this is added 0.5 gm (4.4 mmol) of methanesulphonyl chloride and stirred at 25° C. for five hours. Acetonitrile is evaporated and the residue is dissolved in ethylacetate. The solution is washed with water, dried over sodium sulphate, filtered, and evaporated to give 5-chloro-7-[2-(3-chloro-pyridin-2-yl)-5-trifluoromethyl-2H-pyrazole-3-carbonyl]-1,3-dioxolane-8-oxa-naphthalen-9-one (650 mg) as a solid which is used directly in the next step.

To a solution of crude 5-chloro-7-[2-(3-chloro-pyridin-2-yl)-5-trifluoromethyl-2H-pyrazole-3-carbonyl]-1,3-dioxolane-8-oxa-naphthalen-9-one (330 mg, 0.7 mmol) in 20 ml tetrahydrofuran is added isopropylamine (830 mg, 14 mmol) below 15° C. and stirred for 3 hours. The solvent is evaporated and the residue purified by chromatography to give the product 5-chloro-6-{[2-(3-chloro-pyridin-2-yl)-5-trifluoromethyl-2H-pyrazole-3-carbonyl]-amino}-2,4-dioxolane-benzoic acid isopropylamide is obtained as a solid (350 mg, 94%); LC/MS: 530/532 (M+1)$^+$; m.p.: 156-158° C.

Example 2

Preparation of 5-chloro-6-{[2-(3-chloro-pyridin-2-yl)-5-trifluoromethyl-2H-pyrazole-3-carbonyl]-amino}-2,4-(3'3'difluoro) dioxolane-benzoic acid isopropylamide a) Preparation of

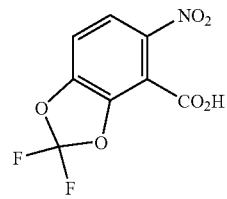 [SMILES: O=C(O)c1c([N+](=O)[O-])ccc2c1OC(F)(F)O2]

To a solution of 150 ml concentrated sulphuric acid is added 37.2 gm (0.2 mol) 2,2-Difluoro-4-formylbenzodioxole (commercial) with external cooling using an ice-bath. In a second flask 32 ml or 65% nitric acid is cooled to 0-5° C. and 32 ml of concentrated sulphuric acid is added slowly. This mixture is then added slowly to the aldehyde in sulphuric acid ensuring that the temperature remains below 20° C. during the addition. The mixture is stirred at ambient temperature for 15 hours and then, poured onto ice water. The precipitate is collected by filtration, washed with water, dissolved in dichloromethane and washed with water. After drying, filtering off the drying agent and evaporation of the solvent, die crude product is passed through a short column to give a mixture of two nitro isomers which are not separated but used directly in the next stage.

To a solution of 30 gm (0.13 mol) of 2,2-Difluoro-4-formyl-5-nitrobenzodioxole mixed with 2,2-Difluoro-4-formyl-6-nitrobenzodioxole in 650 ml acetone is added a hot solution (80° C.) of 34.4 gm KMnO$_4$ in 900 ml water. The addition is such that the exotherm reaches a temperature of 45° C. After stirring for one hour, the acetone is removed by evaporation and the residue is filtered through celite, washing well with water. To the filtrate is added concentrated hydrochloric acid to achieve a pH of 1; the resulting precipitate is collected by filtration, washed with water and dried to give 2,2-Difluoro-4-carboxy-6-nitrobenzodioxole. The aqueous filtrate is saturated with sodium chloride and extracted with ethyl acetate. The organic layer is dried with sodium sulphate, the drying agent removed by filtration and the solvent evaporated to give 2,2-Difluoro-4-carboxy-5-nitrobenzodioxole as an off-white solid with melting point 177-178° C.

b) Preparation of

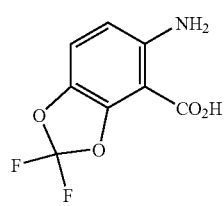

A mixture of 2.5 gm (10 mmol) of 2,2-Difluoro-4-carboxy-5-nitrobenzodioxole in 200 ml ethyl acetate and 200 ml 5% acetic acid is heated to reflux. 2.8 gm (50 mmol) iron powder is added portion-wise every five minutes. After the addition, the reaction is stirred at reflux for four hours. After cooling, the reaction is made basic by adding sodium bicarbonate and then filtered through celite. The solids are washed well with ethyl acetate and the filtrate transferred to a separating funnel where the aqueous layer is separated. The organic phase is washed with saturated salt solution, dried using sodium sulphate and the drying agent removed by filtration. Evaporation of the solvent gives 3,4-(2'2'difluoro)dioxolane-anthranilic acid as a solid with melting point 204° C.

c) Preparation of

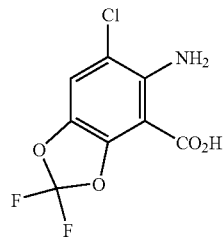

To a mixture of 6.5 gm (30 mmol) of 3,4-(2'2'difluoro) dioxolane-anthranilic acid in 50 ml of dimethylformamide is added 4.2 gm (31.5 mmol) of N-chlorosuccinimide. The reaction is heated to 90° C. for a period of four hours. After cooling, the mixture is poured onto ice-water and extracted with ethyl acetate. The organic phase is washed with sodium chloride solution, dried and the drying agent removed by filtration. Evaporation of the solvent gives the product 6-chloro-3,4-(2'2'-difluoro)dioxolane-anthranilic acid as a solid with melting point 185-186° C.

d) Preparation of

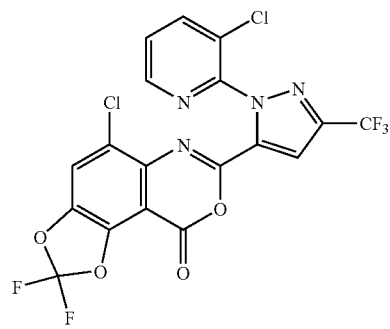 [SMILES: O=c1oc(-c2cc(C(F)(F)F)nn2-c2ncccc2Cl)nc2c(Cl)cc3c(c12)OC(F)(F)O3]

To a mixture of 1.75 gm (6 mmol) of 2-(3-chloro-pyridin-2-yl)-5-trifluoromethyl-2H-pyrazole-3-carboxylic acid in 70 ml of acetonitrile is added 2.2 ml of pyridine and 1.5 gm (6 mmol) of 6-chloro-3,4-(2'2'-difluoro)dioxolane-anthranilic acid. The mixture is cooled to 0-5° C. and to this is added 2.4 gm (20.9 mmol) of methanesulphonyl chloride. The reaction mixture is then stirred for 15 hours, then poured onto icewater, the solid filtered, washed with water and dried to give 5-chloro-7-[2-(3-chloro-pyridin-2-yl)-5-trifluoromethyl-2H-pyrazole-3-carbonyl]-1,3-(2'2'difluoro)dioxolane-8-oxa-naphthalen-9-one as a solid with melting point 198-200° C.

e) Preparation of

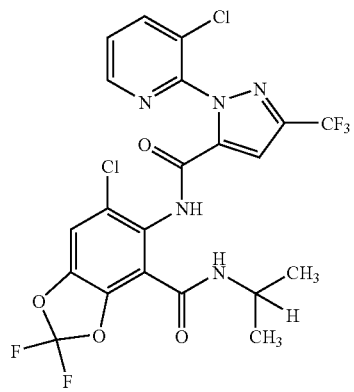 [SMILES: CC(C)NC(=O)c1c(NC(=O)c2cc(C(F)(F)F)nn2-c2ncccc2Cl)c(Cl)cc2c1OC(F)(F)O2]

To a solution of 355 mg (0.7 mmol) of 5-chloro-7-[2-(3-chloro-pyridin-2-yl)-5-trifluoromethyl-2H-pyrazole-3-carbonyl]-1,3-(2'2'difluoro) dioxolane-8-oxa-naphthalen-9-one in 8 ml tetrahydrofuran is added 0.18 ml (2.1 mmol) isopropylamine at ambient temperature. The mixture is stirred for 15 hours, the solvent evaporated and the residue purified by recrystallisation from a mixture of Ethyl acetate/Pentane. The product 5-chloro-6-{[2-(3-chloro-pyridin-2-yl)-5-trifluoromethyl-2H-pyrazole-3-carbonyl]-amino}-2,4-(3'3'difluoro) dioxolane-benzoic acid isopropylamide is obtained as a solid with melting point 186-187° C.

Example 3

Preparation of 5-methyl-6-{[2-(3-chloro-pyridin-2-yl)-5-bromo-2H-pyrazole-3-carbonyl]-amino}-2,4-(3'3'difluoro) dioxolane-benzoic acid isopropylamide a) Preparation of

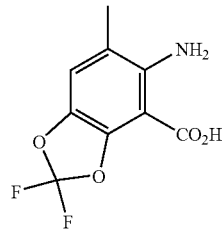

To a mixture of 434 mg (2 mmol) of 3,4-(2'2'difluoro) dioxolane-anthranilic acid in 8 ml of dimethylformamide is added 472 mg (2.1 mmol) of N-iodosuccinimide. The reaction is heated to 90° C. for a period of four hours. After cooling, the mixture is poured onto ice-water and extracted with ethyl acetate. The organic phase is washed with sodium chloride solution, dried and the drying agent removed by filtration. Evaporation of the solvent gives the product 6-iodo-3,4-(2'2'-difluoro)dioxolane-anthranilic acid as a solid with melting point 174-175° C.

b) Preparation of

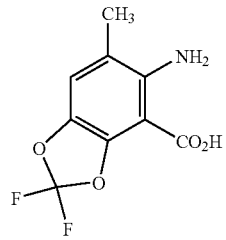

In a flame-dried flask under Argon 1.5 gm (6.7 mmol) of Indium trichloride is placed. This is again dried with an external flame then 15 ml tetrahydrofuran is added and the solution is cooled to −78° C. To this solution is slowly added 6.75 ml (20.2 mmol) of a 3 Molar solution of methylmagnesiumchloride in tetrahydrofuran, to generate in-situ trimethylindium. In a second flask is placed 2.3 gm (6.7 mmol) of 6-iodo-3,4-(2'2'-difluoro)dioxolane-anthranilic acid followed by 30 ml of tetrahydrofuran. To this solution is then added 55 mg (0.067 mmol) of the catalyst Pd(dppf)Cl$_2$.CH$_2$Cl$_2$ and this mixture is heated to reflux. To this refluxing solution is slowly added the solution of trimethylindium in tetrahydrofuran and the whole mixture is further heated at reflux for four hours. After cooling 10 ml of methanol is added, the mixture stirred for 30 minutes and then filtered through celite. The solvent is removed by evaporation and the crude product is stirred in 200 ml of hot ethyl acetate, filtered and partially evaporated. Pentane is then added and the mixture cooled to allow the precipitate to be isolated by filtration to give 6-methyl-3,4-(2'2'-difluoro)dioxolane-anthranilic acid as a solid with melting point>240° C.

c) Preparation of

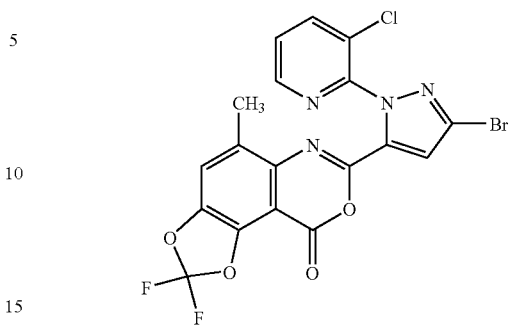

To a mixture of 1.96 gm (6.5 mmol) of 2-(3-chloro-pyridin-2-yl)-5-bromo-2H-pyrazole-3-carboxylic acid in 70 ml of acetonitrile is added 2.4 ml (29.3 mmol) of pyridine and 1.5 gm (6.5 mmol) of 6-methyl-3,4-(2'2'-difluoro)dioxolane-anthranilic acid. The mixture is cooled to 0-5° C. and to this is added 2.6 gm (22.6 mmol) of methanesulphonyl chloride. The reaction mixture is then stirred for 15 hours, then poured onto ice-water, the solid filtered, washed with water and dried to give 5-methyl-7-[2-(3-chloro-pyridin-2-yl)-5-bromo-2H-pyrazole-3-carbonyl]-1,3-(2'2'difluoro)dioxolane-8-oxa-naphthalen-9-one as a solid with melting point 223-225° C.

d) Preparation of

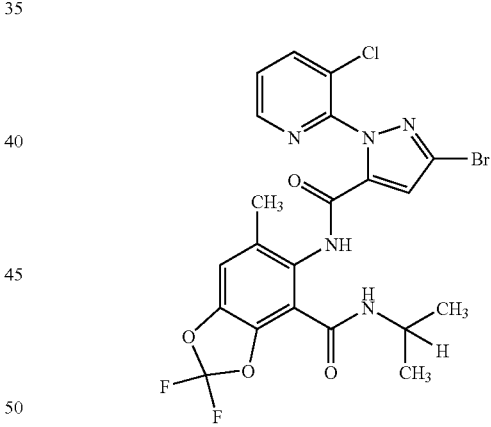

To a solution of 348 mg (0.7 mmol) of 5-methyl-7-[2-(3-chloro-pyridin-2-yl)-5-bromo-2H-pyrazole-3-carbonyl]-1,3-(2'2'difluoro) dioxolane-8-oxa-naphthalen-9-one in 8 ml tetrahydrofuran is added 0.18 ml (2.1 mmol) isopropylamine at ambient temperature. The mixture is stirred for 15 hours, the solvent evaporated and the residue purified by recrystallisation from a mixture of Ethyl acetate/Heptane. The product 5-methyl-6-{[2-(3-chloro-pyridin-2-yl)-5-bromo-2H-pyrazole-3-carbonyl]-amino}-2,4-(3'3'difluoro) dioxolane-benzoic acid isopropylamide is obtained as a solid with melting point 162-163° C.

Example 4

Preparation of 5-chloro-2-hydroxy-6-{[2-(3-chloro-pyridin-2-yl)-5-trifluoromethyl-2H-pyrazole-3-carbonyl]-amino}-indane carboxylic acid isopropylamide a) Preparation of

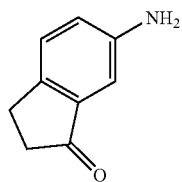 [SMILES: Nc1ccc2c(c1)C(=O)CC2]

This compound is prepared as described in the U.S. Pat. No. 0,167,128 A1, 2004.

b) Preparation of

A solution of 6-aminoindanone (12 g, 81.6 mmol) in N,N-dimethylformamide (220 ml) is treated with N-bromosuccinimide (14.5 g, 81.6 mmol) in portions over a period of one hour and stirred for one hour. Evaporation of the solvent and water/dichloromethane workup followed by purification by chromatography with EtOAc/hexane (1:3) as eluent gives the product 6-amino-7-bromoindanone; LC/MS: 226/228 (M+1)$^+$.

c) Preparation of

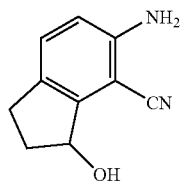 [SMILES: N#Cc1c(N)ccc2c1C(O)CC2]

A solution of 6-amino-7-bromoindanone (2.4 g, 10.6 mmol) in tetrahydrofuran (150 ml) is treated with sodium borohydride (360 mg, 10.6 mmol) in portions, stirred for two hours, and treated dropwise with water. Tetrahydrofuran is evaporated and the residue is dissolved in ethyl acetate and washed with water. The separated organic layer is dried over sodium sulfate, filtered, and evaporated to give 6-amino-7-bromoindan-1-ol; GC/MS: 228/230 (M+1)$^+$.

A suspension of 6-amino-7-bromoindan-1-ol (1 g, 4.3 mmol), zinc cyanide (290 mg, 2.6 mmol), zinc (140 mg, 2.1 mmol), Pd(dba)$_3$ (10 mol %), and dppf (50 mol %) in dimethylacetamide (8 ml) is heated at 140° C. under nitrogen for six hours. The solvent is distilled off at 100° C. under vacuum, the residue treated with dichloromethane, filtered through Celite, and the filtrate is washed with water. The organic layer is separated, dried over sodium sulfate, filtered, and evaporated. Chromatographic purification by using ethyl acetate/hexane as eluent gives 6-amino-7-cyanoindan-1-ol as solid; LC/MS: 175 (M+1)$^+$.

d) Preparation of

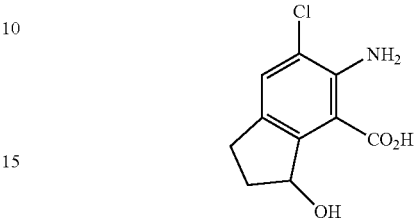

A solution of 6-amino-7-cyanoindan-1-ol (700 mg, 4 mmol) in tetrahydrofuran (50 ml) is treated with N-chlorosuccinimide (530 mg, 4 mmol) in portions over 20 minutes, stirred for 30 minutes, treated with sodiumborohydride (270 mg), and stirred for one hour. The mixture is quenched with water (30 ml), evaporated to remove tetrahydrofuran, and extracted with ethyl acetate. The organic layer is dried over sodium sulfate, filtered, and evaporated to give 6-amino-5-chloro-7-cyanoindan-1-ol (400 mg) which is directly used in the next step; LC/MS: 209/211 (M+1)$^+$.

A solution of the above 6-amino-5-chloro-7-cyanoindan-1-ol in isopropanol (20 ml) is treated with aqueous sodium hydroxide (380 mg in 1 ml of water) and heated at 120° C. for 15 hours. Solvent is evaporated, the residue is treated with water and washed with ethyl acetate. The aqueous layer is acidified and extracted with ethyl acetate. The separated organic layer is dried over sodium sulfate, filtered, and evaporated to give 6-amino-5-chloro-7-carboxy-indan-1-ol which is directly used in the next step. LC/MS: 228/230 (M+1)$^+$.

e) Preparation of

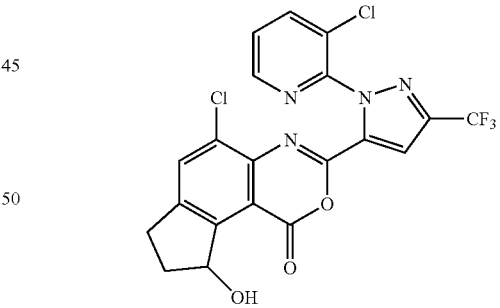

A solution of 6-amino-5-chloro-7-carboxy-indan-1-ol (100 mg, 0.44 mmol), 2-(3-chloro-pyridin-2-yl)-5-trifluoromethyl-2H-pyrazole-3-carboxylic acid (120 mg, 0.44 mmol), and pyridine (0.16 ml, 1.9 mmol) in acetonitrile (25 ml) is cooled to 0° C., treated with methanesulfonyl chloride (170 mg, 1.4 mmol), and stirred for 3 hours. Acetonitrile is evaporated and the residue is dissolved in chloroform. The mixture is washed with water, dried over sodium sulfate, filtered, and evaporated to give 5-chloro-1-hydroxy-7-[2-(3-chloro-pyridin-2-yl)-5-trifluoromethyl-2H-pyrazolyl]-indan-8-oxa-azin-9-one which is directly used in the next step.

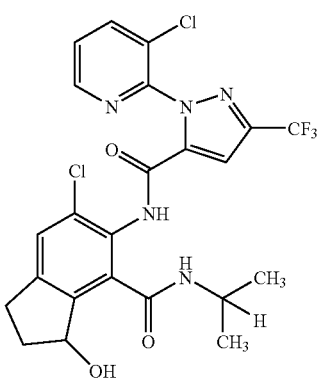 [SMILES: CC(C)NC(=O)c1c(NC(=O)c2cc(C(F)(F)F)nn2-c2ncccc2Cl)c(Cl)cc2c1C(O)CC2]

f) Preparation of

A solution of crude 5-chloro-1-hydroxy-7-[2-(3-chloro-pyridin-2-yl)-5-trifluoromethyl-2H-pyrazolyl]-indan-8-oxa-azin-9-one (60 mg, 0.1 mmol) and isopropylamine (10 mol eq) in tetrahydrofuran (10 ml) is stirred below 10° C. for 4 hours. Evaporation of solvent and purification by chromatography using ethyl acetate/hexane 1:3 as eluent provided the product 5-chloro-2-hydroxy-6-{[2-(3-chloro-pyridin-2-yl)-5-trifluoromethyl-2H-pyrazole-3-carbonyl]-amino}-indane carboxylic acid isopropylamide as a solid; LC/MS: 540/542 (M+1)$^+$; m.p.: 204-205° C.

Example 5

Preparation of 5-chloro-2-fluoro-6-{[2-(3-chloro-pyridin-2-yl)-5-trifluoromethyl-2H-pyrazole-3-carbonyl]-amino}-indane carboxylic acid isopropylamide Preparation of

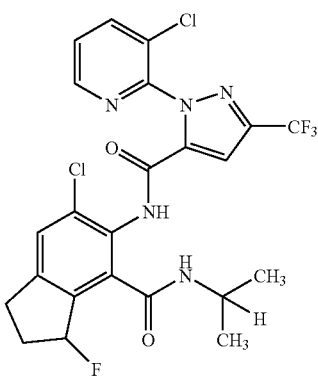 [SMILES: CC(C)NC(=O)c1c(NC(=O)c2cc(C(F)(F)F)nn2-c2ncccc2Cl)c(Cl)cc2c1C(F)CC2]

A solution of 5-chloro-2-hydroxy-6-{[2-(3-chloro-pyridin-2-yl)-5-trifluoromethyl-2H-pyrazole-3-carbonyl]-amino}-indane carboxylic acid isopropylamide (100 mg, 0.18 mmol) in dichloromethane is cooled to 0° C., treated with diethylaminosulfurtrifluoride (29 mg, 1.8 mmol), stirred for 2 hours, and treated with water. Organic layer is separated, dried over sodium sulfate, filtered, and evaporated. Purification by chromatography using ethyl acetate/hexane as eluent gives 5-chloro-2-fluoro-6-{[2-(3-chloro-pyridin-2-yl)-5-trifluoromethyl-2H-pyrazole-3-carbonyl]-amino}-indane carboxylic acid isopropylamide as solid; LC/MS: 542/544 (M+1)$^+$; m.p.: 98-99° C.

Example 6

Preparation of 5-chloro-6-{[2-(3-chloro-pyridin-2-yl)-5-trifluoromethyl-2H-pyrazole-3-carbonyl]-amino}-indan-2-one carboxylic acid isopropylamide Preparation of

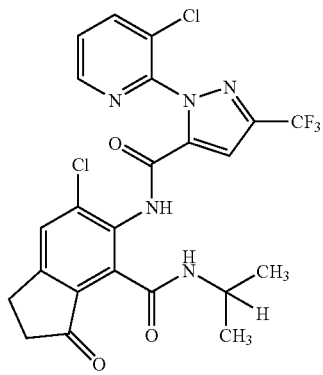 [SMILES: CC(C)NC(=O)c1c(NC(=O)c2cc(C(F)(F)F)nn2-c2ncccc2Cl)c(Cl)cc2c1C(=O)CC2]

A solution of 5-chloro-2-hydroxy-6-{[2-(3-chloro-pyridin-2-yl)-5-trifluoromethyl-2H-pyrazole-3-carbonyl]-amino}-indane carboxylic acid isopropylamide (230 mg, 0.35 mmol) in dichloromethane is treated with pyridinium chlorochromate (29 mg, 1.0 mmol), stirred for 10 hours, and treated with water. Organic layer is separated, dried over sodium sulfate, filtered, and evaporated. Purification by chromatography using ethyl acetate/hexane as eluent gives 5-chloro-6-{[2-(3-chloro-pyridin-2-yl)-5-trifluoromethyl-2H-pyrazole-3-carbonyl]-amino}-indan-2-one carboxylic acid isopropylamide as solid; LC/MS: 540/542 (M+1)$^+$; m.p.: 198-199° C.

Example 7

Preparation of 5-chloro-6-{[2-(3-chloro-pyridin-2-yl)-5-trifluoromethyl-2H-pyrazole-3-carbonyl]-amino}-indan-2-one-oxime carboxylic acid isopropylamide Preparation of

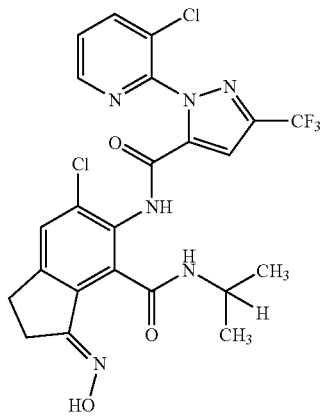 [SMILES: CC(C)NC(=O)c1c(NC(=O)c2cc(C(F)(F)F)nn2-c2ncccc2Cl)c(Cl)cc2c1/C(=N/O)CC2]

A suspension of 5-chloro-6-{[2-(3-chloro-pyridin-2-yl)-5-trifluoromethyl-2H-pyrazole-3-carbonyl]-amino}-indan-2- one carboxylic acid isopropylamide (77 mg, 0.14 mmol), hydroxylamine hydrochloride (19 mg, 0.28 mmol) and sodium acetate (24 mg, 0.29 mmol) in tetrahydrofuran (20 ml) is stirred for 4 hours. Solvent is evaporated and the residue is dissolved in ethyl acetate. The mixture is washed with water, dried over sodium sulfate, filtered, and evaporated. Purification by chromatography using ethyl acetate/hexane as eluent gives 5-chloro-6-{[2-(3-chloro-pyridin-2-yl)-5-trifluoromethyl-2H-pyrazole-3-carbonyl]-amino}-indan-2-one-oxime carboxylic acid isopropylamide as solid; LC/MS: 555/557 (M+1)⁺; m.p.: 188-190° C.

Example 8

Preparation of

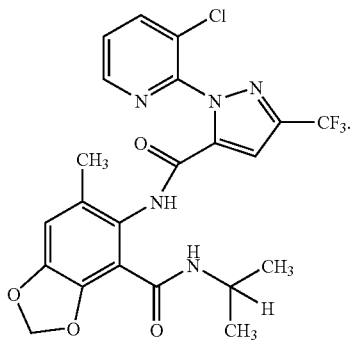 [SMILES: Cc1cc2c(c(C(=O)NC(C)C)c1NC(=O)c1cc(C(F)(F)F)nn1-c1ncccc1Cl)OCO2]

a) Preparation of

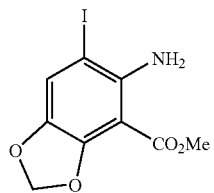 [SMILES: COC(=O)c1c(N)c(I)cc2c1OCO2]

A solution of 3,4-dioxolane-anthranilic acid methyl ester (2 g, 10 mmol) in THF (200 ml) is cooled to 0° C., treated with silver trifluoroacetate (3.35 g, 15 mmol) and Iodine (1.5 g, 6 mmol), and stirred for 30 min. The reaction mixture is quenched with aqueous sodium thiosulphate, concentrated to remove tetrahydrofuran, diluted with ethyl acetate, stirred for 5 min, and filtered through celite. The filtrate is washed with water (100 ml), dried with sodium sulphate, filtered, and evaporated. Purification by chromatography with ethyl acetate/hexane (1:9) as eluent gives 6-iodo-3,4-dioxolane-anthranilic acid methyl ester as a white solid besides minor amounts of the 5-iodo regioisomer; LC/MS: 326 (M+1)⁺.

b) Preparation of

Error! Objects cannot be created from editing field codes.

A solution of 6-iodo-3,4-dioxolane-anthranilic acid methyl ester (0.25 g, 0.77 mmol) in to tetrahydrofuran (15 ml) is treated with diisopropylethyl amine (0.99 g, 7.7 mmol) and di-tert-butylcarbonate (1.69 g, 7.7 mmol) and stirred at 50° C. for 10 hours. Tetrahydrofuran is evaporated and the residue is dissolved in ethyl acetate (50 ml), washed with water (30 ml), dried with sodium sulphate and evaporated. Purification by chromatography (ethyl acetate/hexane 1:9) gives 6-iodo-3,4-dioxolane-(di-N-tert-butyloxycarbonyl)-anthranilic acid methyl ester; LC/MS: 522 (M+1)⁺.

c) Preparation of

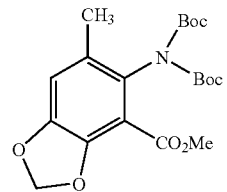 [SMILES: COC(=O)c1c2c(cc(C)c1N(C(=O)OC(C)(C)C)C(=O)OC(C)(C)C)OCO2]

A suspension of 6-iodo-3,4-dioxolane-(di-N-tert-butyloxycarbonyl)-anthranilic acid methyl ester (0.1 g, 0.019 mmol), potassium carbonate (0.026 g, 0.019 mmol), tetrakis(triphenyl phosphine)palladium (1 mol %) and trimethylboraxine (0.026 ml, 0.019 mmol) in 1,4-dioxane (5 ml) is stirred under nitrogen at 105° C. for 10 hours. Solvent is removed and the residue is taken in ethyl acetate (50 ml). This mixture is washed with water (30 ml), dried with sodium sulphate and evaporated. Purification by chromatography (ethyl acetate/hexane 1:9) gives 6-methyl-3,4-dioxolane-(di-N-butyloxycarbonyl)-anthranilic acid methyl ester; LC/MS: 410 (M+1)⁺.

d) Preparation of

Error! Objects cannot be created from editing field codes.

A solution of 5-amino-2,3-dioxolanebenzoic acid methyl ester (0.5 g 2.5 mmol) (Chemische Berichte 1971, 104(8), 2347) in H₂SO₄ (0.5 ml in 9.5 ml) at 0° C. is treated with a solution of sodium nitrite (0.21 ml, 3.1 mmol) in water (1 ml), stirred for 1 hour, treated with a solution of potassium iodide (1.24 g, 7.5 mmol) in water (2 ml), and stirred at 80° C. for 10 min. The reaction mixture is quenched with water and extracted with dichloromethane (20 ml). Organic layer is separated and washed with water (25 ml), dried with sodium sulphate, and evaporated to give 5-iodo-2,3-dioxolanebenzoic acid methyl ester which is directly used in the next step.

e) Preparation of

Error! Objects cannot be created from editing field codes.

A suspension of 5-iodo-2,3-dioxolanebenzoic acid methyl ester (0.1 g, 0.32 mmol), potassium carbonate (0.048 g, 0.35 mmol), tetrakis(triphenylphosphine)palladium (1 mol %) and trimethylboraxine (0.089 ml, 0.64 mmol) in 1,4-dioxane (5 ml) is stirred under nitrogen at 105° C. for 10 hours. Solvent is removed and the residue is taken in ethyl acetate (50 ml). This mixture is washed with water (30 ml), dried with sodium sulphate and evaporated. Purification by chromatography (ethyl acetate/hexane 5:95) gives 5-methyl-2,3-dioxolanebenzoic acid methyl ester; GC/MS: 194 (M+1)⁺.

f) Preparation of

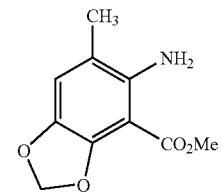

(i) From 6-methyl-3,4-dioxolane-(di-N-butyloxycarbonyl)-anthranilic acid methyl ester:

A solution of 6-methyl-3,4-dioxolane-(di-N-butyloxycarbonyl)-anthranilic acid methyl ester (0.05 g, 0.12 mmol) in dichloromethane (20 ml) at 0° C. is treated with trifluoroacetic acid (0.46 ml, 0.61 mmol) and stirred for 10 hours. The reaction mixture is quenched with 10% aqueous sodium bicarbonate solution and treated with dichloromethane (20 ml). Organic layer is separated, washed with water (25 ml), dried with sodium sulphate, and evaporated to afford 6-methyl-3,4-dioxolane-anthranilic acid methyl ester; LC/MS: 210 (M+1)⁺.

(ii) From 5-methyl-2,3-dioxolanebenzoic acid methyl ester:

A solution of 5-methyl-2,3-dioxolanebenzoic acid methyl ester (2 g, 10 mmol) and HNO$_3$ (1 ml) is stirred at 0° C. for 1 hour. The reaction mixture is quenched with water (5 ml) and extracted with ethyl acetate. The organic layer is washed with water (10 ml), dried with sodium sulphate, and evaporated to obtain 5-methyl-6-nitro-2,3-dioxolanebenzoic acid methyl ester (1.2 g, 36%) which is directly used in the next step.

A suspension of 5-methyl-6-nitro-2,3-dioxolanebenzoic acid methyl ester (2 g, 8.3 mmol) and Iron power (1.3 g, 25 mmol) in 1:1 methanol/water (50 ml) is heated to 55° C., treated with ammonium chloride (1.3 g, 25 mmol), and stirred for 3 hours. The hot mixture is filtered through celite and the filtrate is evaporated. The residue is dissolved in dichloromethane, washed with water (30 ml), dried with sodium sulphate, and evaporated to give 6-methyl-3,4-dioxolane-anthranilic acid methyl ester; LC/MS: 210 (M+1)⁺.

g) Preparation of

Error! Objects cannot be created from editing field codes.

A solution of 6-methyl-3,4-dioxolane-anthranilic acid methyl ester (0.24 g, 1.1 mmol) in 1:1 methanol/1,4-dioxane (15 ml) is treated with a solution of sodium hydroxide (0.05 g) in water (0.2 ml) and stirred at 70° C. for 4 hours. The mixture is concentrated, co-evaporated with toluene (2×20 ml) and dried under vacuum to give 6-methyl-3,4-dioxolane-anthranilic acid sodium salt.

A solution of the above salt, 2-(3-chloro-pyridin-2-yl)-5-trifluoromethyl-2H-pyrazole-3-carboxylic acid (0.35 g, 4.8 mmol), and pyridine (0.38 g, 4.8 mmol) in 1:1 acetonitrile and tetrahydrofuran (100 ml) is cooled to 0° C., treated with a solution of mesyl chloride (0.28 ml, 3.6 mmol) in acetonitrile (1 ml), stirred for 4 hours, and concentrated. The residue is dissolved in dichloromethane (50 ml), washed with water (50 ml), dried with sodium sulphate, and evaporated to give 5-methyl-7-[2-(3-chloro-pyridin-2-yl)-5-trifluoromethyl-2H-pyrazole-3-carbonyl]-1,3-dioxolane-8-oxa-naphthalen-9-one; LC/MS: 451/453 (M+1)⁺.

h) Preparation of

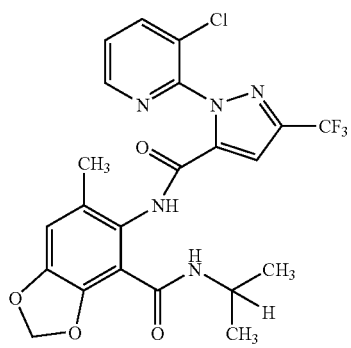 [SMILES: Cc1cc2c(c(C(=O)NC(C)C)c1NC(=O)c1cc(C(F)(F)F)nn1-c1ncccc1Cl)OCO2]

To a solution of crude 5-methyl-7-[2-(3-chloro-pyridin-2-yl)-5-trifluoromethyl-2H-pyrazole-3-carbonyl]-1,3-dioxolane-8-oxa-naphthalen-9-one (0.15 g, 0.33 mmol) in 50 ml tetrahydrofuran is added isopropylamine (0.14 ml, 1.6 mmol) below 15° C. and stirred for 3 hours. The solvent is evaporated and the residue purified by chromatography to give the product 5-methyl-6-{[2-(3-chloro-pyridin-2-yl)-5-trifluoromethyl-2H-pyrazole-3-carbonyl]-amino}-2,4-dioxolane-benzoic acid isopropylamide is obtained as a solid; LC/MS: 510 (M+1)⁺; m.p.: 133-135° C.

Example 9

Preparation of but-2-enedioic acid monopentyl ester

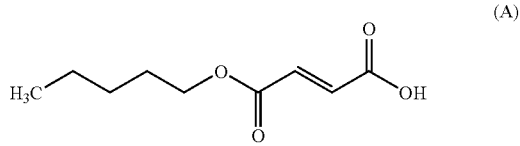

(A)

To a solution of 1-Pentanol (4.4 g, 0.05 mol) in dichloromethane (40 ml) is added maleicanhydride (9.0 g, 0.092 mol). The reaction mixture is cooled externally using an ice bath and then 4-dimethylaminopyridine (0.46 g, 3.8 mmol) added, followed by triethylamine (5.9 gm, 0.058 mol) maintaining a temperature of <10° C. The reaction mixture is then stirred overnight at room temperature. The solvent is removed by evaporation and the dark to residue is washed several times with ethyl acetate. The combined organic washings are washed twice with dilute hydrochloric acid followed by washing with salt solution. After drying over sodium sulphate and evaporation of the solvent, the residue is purified by chromatography. Fractions containing product are combined, evaporated and the product dissolved in ethyl acetate. The ethyl acetate is washed with dilute hydrochloric acid followed by salt solution, dried and evaporated to give the product A as a light-brown oil. ¹H NMR (CDCl$_3$): 0.9 (3H, m), 1.4 (4H, m), 1.7 (2H, m), 4.3 (2H, m), 6.4 (2H, dd), 10.0 (1H, broad). M+1: 187

Example 10

Preparation of 2-bromo-succinic acid 1-pentyl ester

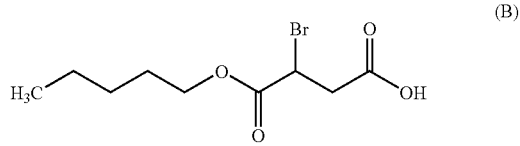

(B)

To a solution of hydrobromic acid (33% in acetic acid) (13.1 ml, 74.7 mmol) is added n-pentylfumarate-half ester (9.3 g, 50 mmol) dropwise. The reaction mixture is stirred at room temperature overnight and the solvent is then removed under reduced pressure. The product B is obtained in pure form as an oil. ¹H NMR (CDCl$_3$): 0.9 (3H, m), 1.3 (4H, m), 1.7 (2H, m), 3.0 (1H, dd), 3.35 (1H, dd), 4.2 (2H, m), 4.5 (1H, dd), 10.0 (1H, broad).

Example 11

Preparation of 2-bromo-3-chlorocarbonyl-propionic acid pentyl ester

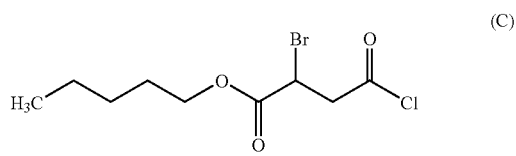

(C)

To a solution of B (108.7 g, 0.4 mol) in dichloromethane (500 ml) is added four drops of dimethylformamide. Oxalyl chloride (41.3 ml, 0.488 mol) is slowly added; after the addition is complete and gas evolution had ceased, the reaction mixture is heated to reflux and stirred 30 minutes. The solvent is then removed under reduced pressure to give product C as an oil. $^1$H NMR (CDCl$_3$): 0.9 (3H, m), 1.3 (4H, m), 1.7 (2H, m), 3.5 (1H, dd), 3.7 (1H, dd), 4.2 (2H, m), 4.55 (1H, dd).

Example 12

Preparation of 2-(3-chloro-pyridin-2-yl)-5-oxo-pyrazolidine-3-carboxylic acid pentyl ester

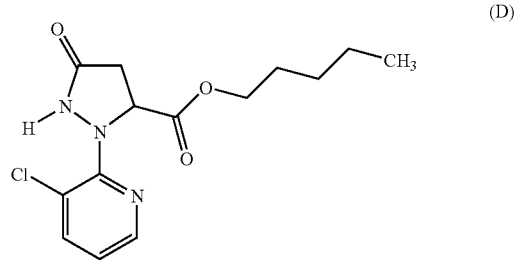 [SMILES: CCCCCOC(=O)C1CC(=O)NN1c1ncccc1Cl]

(D)

To a solution of 3-chloro-2-hydrazinonpyridine (54 g, 0.37 mol) in acetonitrile (750 ml) is added sodium bicarbonate (68 g, 0.81 mol). The mixture is stirred and the acid chloride C (115.7 g, 0.4 mol) is added drop-wise while cooling externally with an ice bath. The cooling bath is then removed and the mixture stirred four hours at ambient temperature. The mixture is then heated to 40° C. (internal temperature) and stirred overnight; TLC then showed a mixture of product and intermediate. Additional sodium bicarbonate (34 g, 0.4 mol) is added and the mixture stirred at 40° C. for 15 hours. The mixture is allowed to cool to room temperature, filtered through celite and the solvent removed by evaporation. The residue is purified by column chromatography using Heptane:Ethyl acetate (1:1) as eluant. Product D is obtained as an oil. $^1$H nmr (CDCl$_3$): 0.9 (3H, m), 1.3 (4H, m), 1.7 (2H, m), 2.7 (1H, dd), 3.1 (1H, dd), 4.2 (2H, m), 5.3 (1H, dd), 7.0 (1H, m), 7.7 (1H, m), 8.15 (1H, broad), 8.2 (1H, m). M+1: 313

Example 13

Preparation of 2-(3-chloro-pyridin-2-yl)-5-hydroxy-2H-pyrazole-3-carboxylic acid pentyl ester

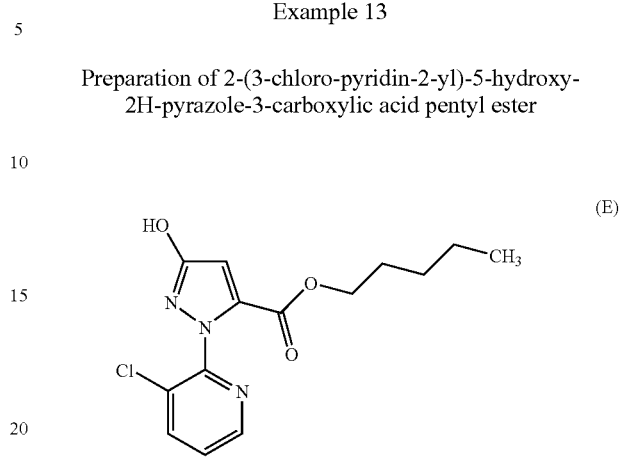

(E)

To a solution of D (9.35 g, 0.03 mol) in acetonitrile (100 ml) is added oxone (11.7 g, 0.019 mol) portion-wise with good stirring. The reaction mixture is then heated to 90° C. and stirred at this temperature overnight. After cooling to ambient temperature, the reaction mixture is filtered and the solvent is removed under reduced pressure. The residue is dissolved in ethyl acetate, washed with water, salt solution and the organic layer dried and evaporated. The crude product E is re-crystallised using a mixture of ethyl acetate and pentane to give E as a solid, m.p. 172-173° C. $^1$H nmr (CDCl$_3$): 0.9 (3H, m), 1.3 (4H, m), 1.55 (2H, m), 4.2 (2H, m), 6.35 (1H, s), 7.4 (1H, m), 7.9 (1H, m), 8.5 (1H, m), 10.5 (1H, broad). M+1: 310

Example 14

Preparation of 2-(3-chloro-pyridin-2-yl)-5-methoxy-2H-pyrazole-3-carboxylic acid pentyl ester

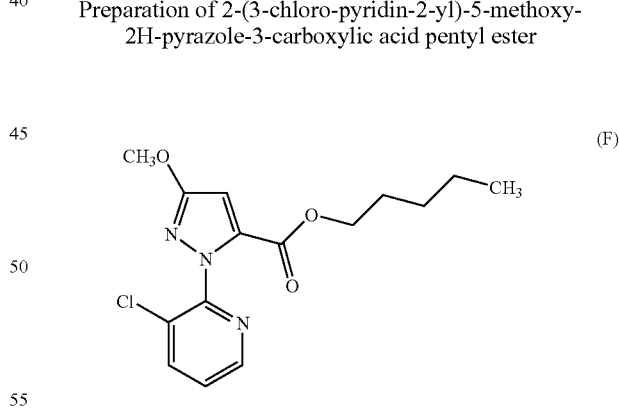

(F)

To a solution of E (6.5 g, 0.021 mol) in acetonitrile (120 ml) is added solid potassium carbonate (7.2 g, 0.05 mol) at ambient temperature. The mixture is stirred for 2 hours after which time a solution of methyl iodide (4.5 g 0.031 mol) in acetonitrile (5 ml) is added. The reaction mixture is then stirred at ambient temperature for 48 hours. The solvent is then evaporated and the residue portioned between water and ethyl acetate. The organic layer is separated, washed twice with salt solution, dried and evaporated. The crude product F is purified by chromatography using a mixture of heptane:ethyl acetate (3:1) as eluent. Product F is obtained as an oil. $^1$H nmr (CDCl$_3$): 0.9 (3H, t), 1.3 (4H, m), 1.55 (2H, m), 3.95 (1H, s), 4.2 (2H, t), 6.45 (1H, s), 7.4 (1H, m), 7.9 (1H, m), 8.5 (1H, m). M+1: 324

Example 15

Preparation of 5-chloro-2-(3-chloro-pyridin-2-yl)-3,4-dihydro-2H-pyrazole-3-carboxylic acid pentyl ester

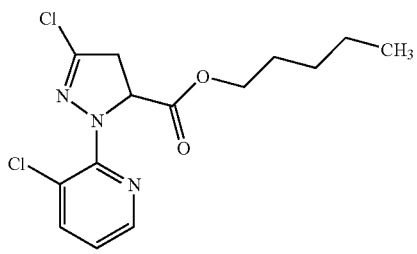

(G)

To a solution of D (11.5 g, 0.037 mol) in acetonitrile (100 ml) is added phosphorus oxychloride (4.3 ml, 0.041 mol) drop-wise under an atmosphere of argon. The reaction mixture is heated to reflux for a period of 45 minutes. After cooling to ambient temperature, most of the solvent is evaporated and the residue is then added drop-wise to a solution of sodium bicarbonate (0.17 mol) with stirring. After 15 minutes, dichloromethane is added and the mixture stirred for one hour. The organic layer is separated, washed twice with water, dried and evaporated to give product G as an oil. $^1$H nmr (CDCl$_3$): 0.9 (3H, t), 1.2 (4H, m), 1.55 (2H, m), 3.2 (1H, dd), 3.4 (1H, dd), 4.1 (2H, t), 5.3 (1H, dd), 6.9 (1H, m), 7.7 (1H, m), 8.1 (1H, m). M+1: 331

Example 16

Preparation of 5-chloro-2-(3-chloro-pyridin-2-yl)-2H-pyrazole-3-carboxylic acid pentyl ester

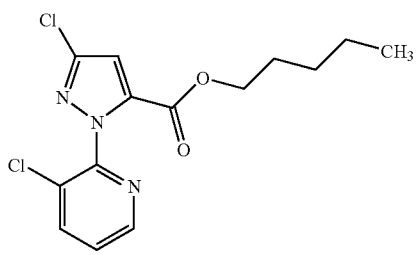

(H)

To a solution of G (10.4 g, 0.03 mol) in acetonitrile (120 ml) is added oxone (28.5 g, 0.046 mol) portion-wise with good stirring. The reaction mixture is then heated to 90° C. and stirred at this temperature for 15 hours. After cooling to ambient temperature, the reaction mixture is filtered and the solvent is removed under reduced pressure. The residue is dissolved in ethyl acetate, washed with water, salt solution and the organic layer dried and evaporated. The crude product H is purified by chromatography using a mixture of heptane:ethyl acetate (5:1) as eluent. Product H is obtained as an oil.

$^1$H nmr (CDCl$_3$): 0.9 (3H, t), 1.3 (4H, m), 1.55 (2H, m), 4.2 (2H, t), 6.9 (1H, s), 7.4 (1H, m), 7.9 (1H, m), 8.5 (1H, m). M+1: 329

Example 17

Preparation of 5-bromo-2-(3-chloro-pyridin-2-yl)-3,4-dihydro-2H-pyrazole-3-carboxylic acid pentyl ester

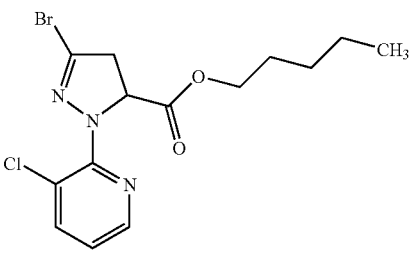

(I)

To a solution of D (11.5 g, 0.037 mol) in acetonitrile (100 ml) is added phosphorus oxybromide (6.8 g, 0.024 mol) drop-wise under an atmosphere of argon. The reaction mixture is heated to reflux for a period of 45 minutes. After cooling to ambient temperature, most of the solvent is evaporated and the residue is then added drop-wise to a solution of sodium bicarbonate (0.108 mol) with stirring. After 15 minutes, dichloromethane is added and the mixture stirred for one hour. The organic layer is separated, washed twice with water, dried and evaporated to give product I as an oil. $^1$H nmr (CDCl$_3$): 0.8 (3H, t), 1.2 (4H, m), 1.55 (2H, m), 3.2 (1H, dd), 3.45 (1H, dd), 4.1 (2H, t), 5.3 (1H, dd), 6.9 (1H, m), 7.7 (1H, m), 8.1 (1H, m). M+1: 376

Example 18

Preparation of 5-bromo-2-(3-chloro-pyridin-2-yl)-2H-pyrazole-3-carboxylic acid pentyl ester

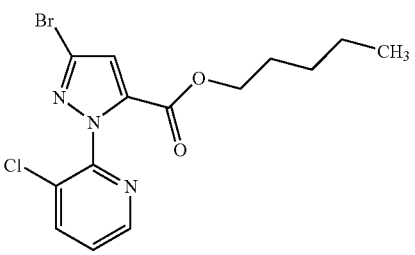

(J)

To a solution of J (11.5 g, 0.03 mol) in acetonitrile (120 ml) is added oxone (27.8 g, 0.045 mol) portion-wise with good stirring. The reaction mixture is then heated to 90° C. and stirred at this temperature overnight. After cooling to ambient temperature, the reaction mixture is filtered and the solvent is removed under reduced pressure. The residue is dissolved in ethyl acetate, washed with water, salt solution and the organic layer dried and evaporated. The crude product J is purified by chromatography using a mixture of heptane:ethyl acetate (5:1) as eluent. Product J is obtained as an oil. $^1$H nmr (CDCl₃): 0.9 (3H, t), 1.3 (4H, m), 1.55 (2H, m), 4.2 (2H, t), 6.9 (1H, s), 7.4 (1H, m), 7.9 (1H, m), 8.5 (1H, m). M+1: 374

TABLE P

Physical data of compounds of formula I:

| Compound No. | Structures | Melting Point °C. |
|---|---|---|
| P.1 | (structure) example 1 | 156-158 |
| P.2 | (structure) | 167-169 |
| P.3 | (structure) | 174-176 |
| P.4 | (structure) | 149-151 |

TABLE P-continued

Physical data of compounds of formula I:

| Compound No. | Structures | Melting Point °C. |
|---|---|---|
| P.5 | (structure) | 146-148 |
| P.6 | (structure) | 195-197 |
| P.7 | (structure) | 171-173 |
| P.8 | (structure) | 159-161 |

TABLE P-continued

Physical data of compounds of formula I:

| Compound No. | Structures | Melting Point °C. |
|---|---|---|
| P.9 | 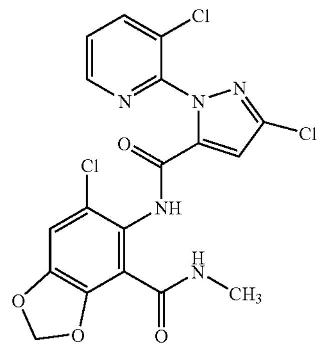 [SMILES: CNC(=O)c1c(NC(=O)c2cc(Cl)nn2-c2ncccc2Cl)c(Cl)cc2c1OCO2] | 224-226 |
| P.10 | 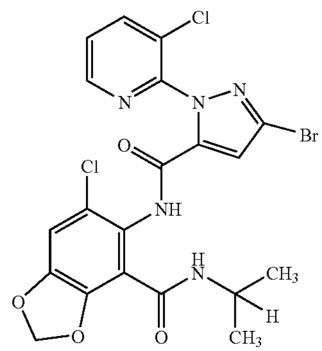 | 132-134 |
| P.11 | 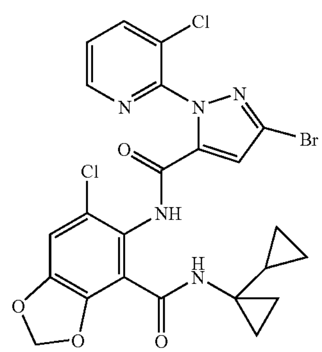 | 185-187 |
| P.12 | 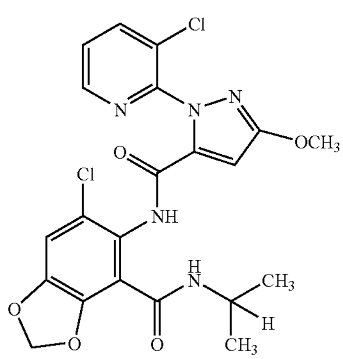 [SMILES: COc1cc(C(=O)Nc2c(Cl)cc3c(c2C(=O)NC(C)C)OCO3)n(-c2ncccc2Cl)n1] | 119-121 |
| P.13 | 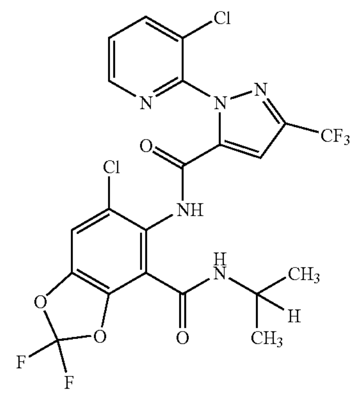 | 186-187 |
| | example 2 | |
| P.14 | 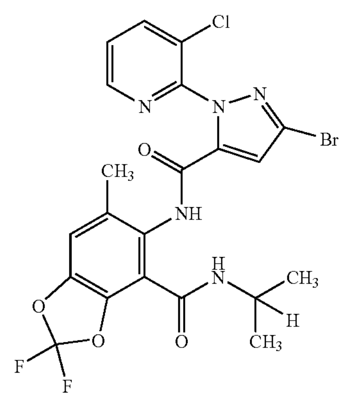 | 162-163 |
| | example 3 | |
| P.15 | 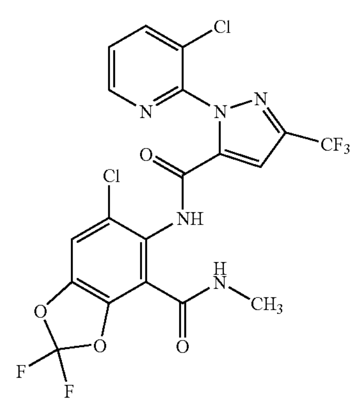 [SMILES: CNC(=O)c1c(NC(=O)c2cc(C(F)(F)F)nn2-c2ncccc2Cl)c(Cl)cc2c1OC(F)(F)O2] | 200-201 |

TABLE P-continued
Physical data of compounds of formula I:
| Compound No. | Structures | Melting Point °C. |
|---|---|---|
| P.16 | 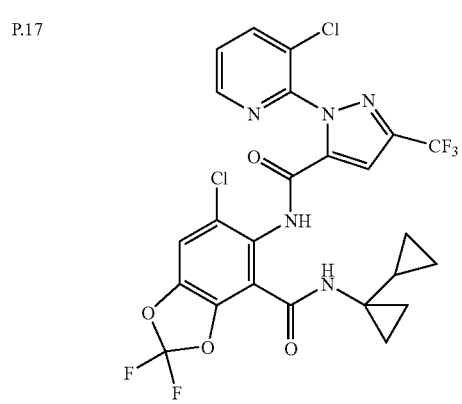 | 227-229 |
| P.17 | 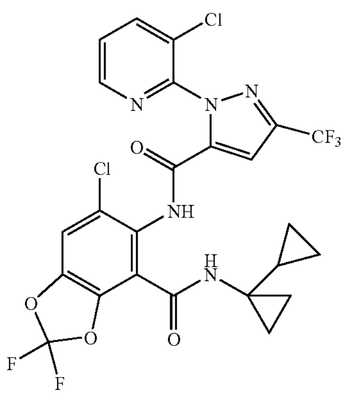 [SMILES: O=C(NC1(C2CC2)CC1)c1c(NC(=O)c2cc(C(F)(F)F)nn2-c2ncccc2Cl)c(Cl)cc2c1OC(F)(F)O2] | 223-224 |
| P.18 | 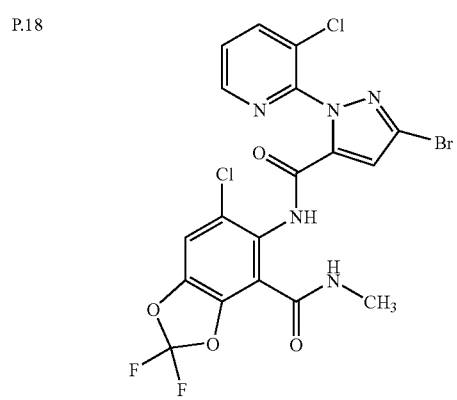 | 182-183 |
| P.19 | 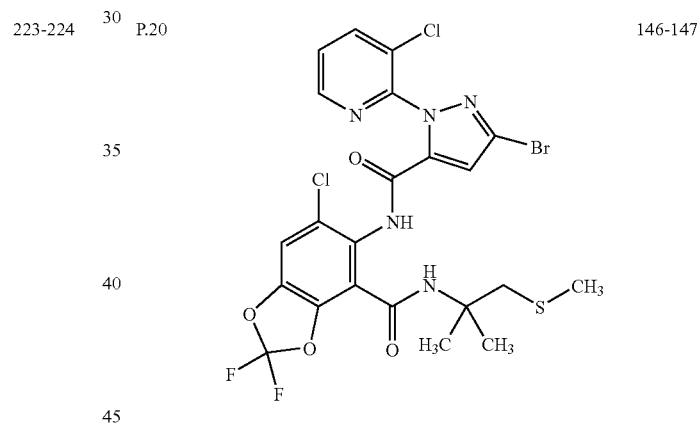 | 162-163 |
| P.20 | | 146-147 |
| P.21 | 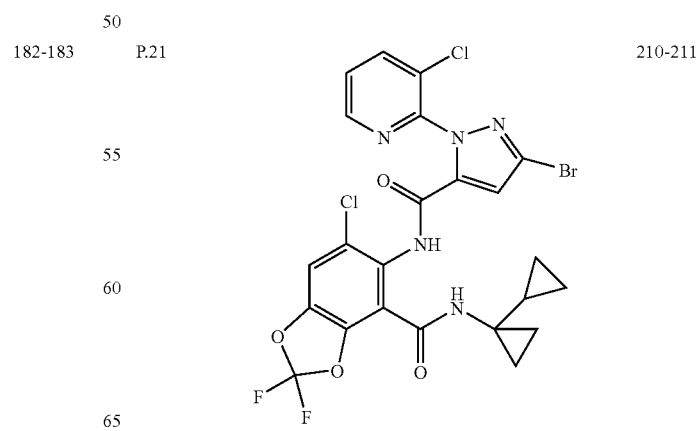 | 210-211 |

TABLE P-continued

Physical data of compounds of formula I:

| Compound No. | Structures | Melting Point °C. |
|---|---|---|
| P.22 | 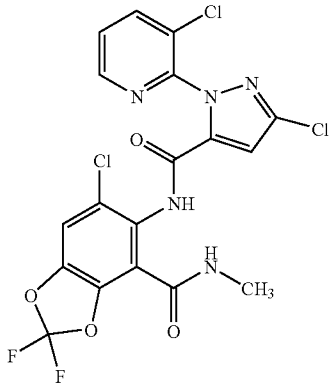 [SMILES: CNC(=O)c1c(NC(=O)c2cc(Cl)nn2-c2ncccc2Cl)c(Cl)cc2c1OC(F)(F)O2] | 200-201 |
| P.23 | 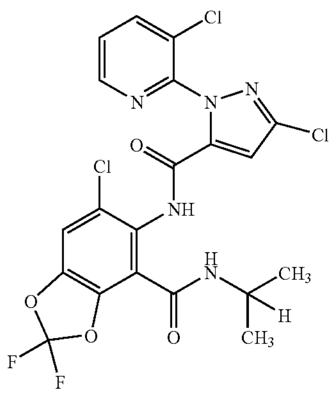 [SMILES: CC(C)NC(=O)c1c(NC(=O)c2cc(Cl)nn2-c2ncccc2Cl)c(Cl)cc2c1OC(F)(F)O2] | 154-156 |
| P.24 | 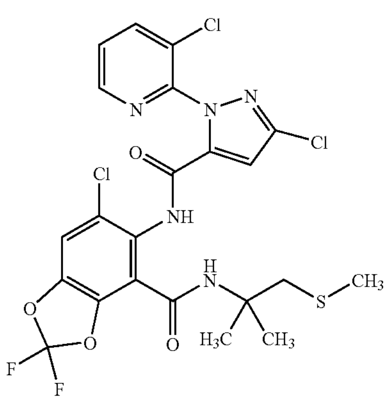 [SMILES: CSCC(C)(C)NC(=O)c1c(NC(=O)c2cc(Cl)nn2-c2ncccc2Cl)c(Cl)cc2c1OC(F)(F)O2] | 147-148 |
| P.25 | 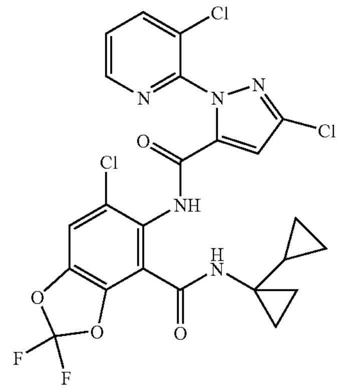 | 238-239 |
| P.26 | 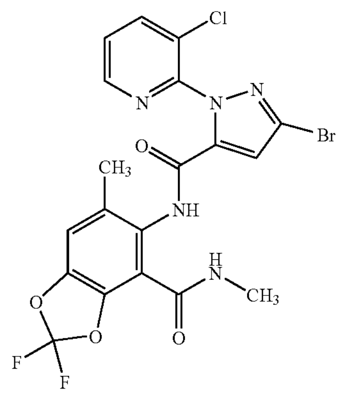 [SMILES: CNC(=O)c1c(NC(=O)c2cc(Br)nn2-c2ncccc2Cl)c(C)cc2c1OC(F)(F)O2] | 178-179 |
| P.27 | 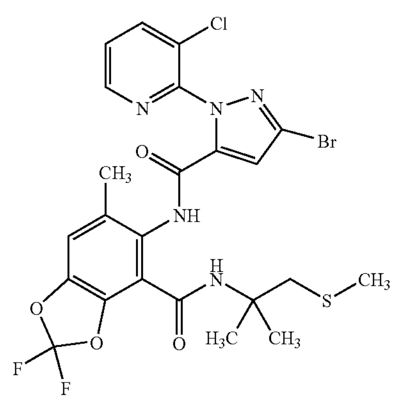 | 192-193 |

TABLE P-continued

Physical data of compounds of formula I:

| Compound No. | Structures | Melting Point °C. |
|---|---|---|
| P.28 | 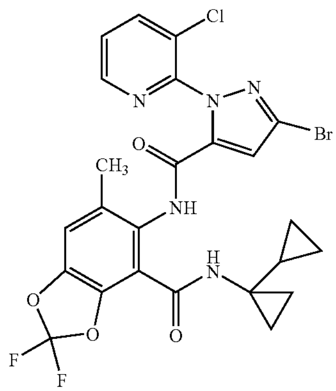 [SMILES: Cc1cc2c(c(C(=O)NC3(C4CC4)CC3)c1NC(=O)c1cc(Br)nn1-c1ncccc1Cl)OC(F)(F)O2] | 187-188 |
| P.29 | 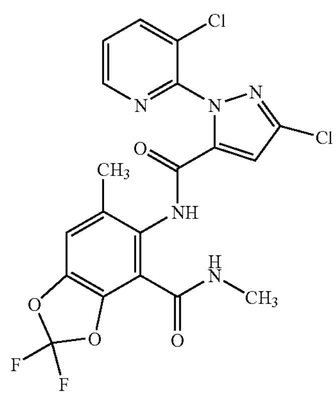 | 198-200 |
| P.30 | 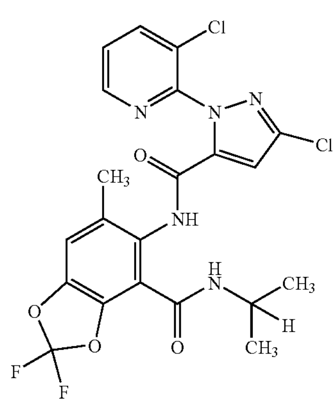 [SMILES: Cc1cc2c(c(C(=O)NC(C)C)c1NC(=O)c1cc(Cl)nn1-c1ncccc1Cl)OC(F)(F)O2] | 220-222 |
| P.31 | | 178-179 |
| P.32 | | 219-220 |
| P.33 | | 200-201 |

TABLE P-continued
Physical data of compounds of formula I:
| Compound No. | Structures | Melting Point °C. |
|---|---|---|
| P.34 | 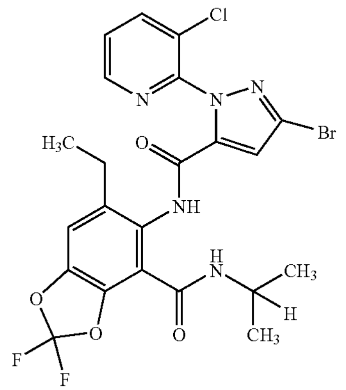 [SMILES: CCc1cc2c(c(C(=O)NC(C)C)c1NC(=O)c1cc(Br)nn1-c1ncccc1Cl)OC(F)(F)O2] | 221-222 |
| P.35 | 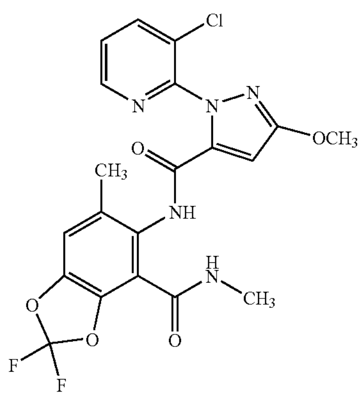 | 198-199 |
| P.36 | 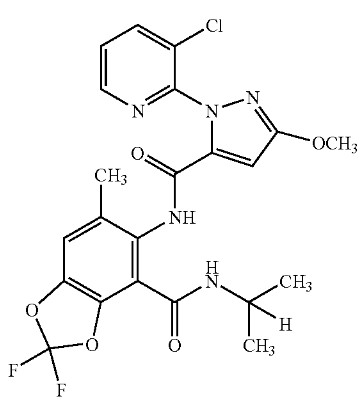 [SMILES: COc1cc(C(=O)Nc2c(C)cc3c(c2C(=O)NC(C)C)OC(F)(F)O3)n(-c2ncccc2Cl)n1] | 209-210 |
| P.37 | | 163-165 |
| P.38 | | 160-162 |
| P.39 | | 192-193 |
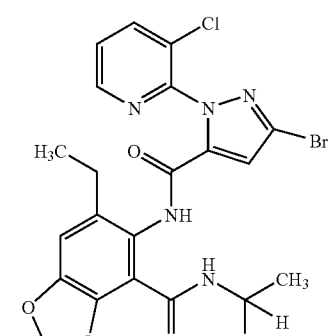

TABLE P-continued
Physical data of compounds of formula I:
| Compound No. | Structures | Melting Point °C. |
|---|---|---|
| P.40 | 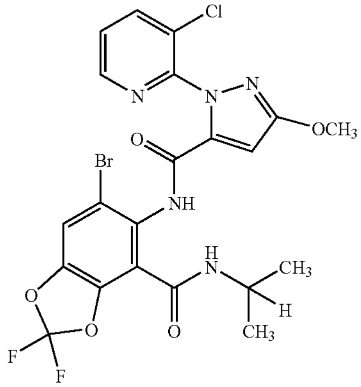 | 184-185 |
| P.41 | 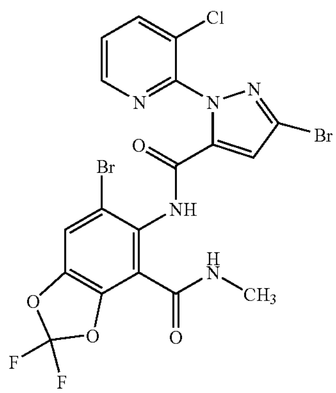 [SMILES: CNC(=O)c1c(NC(=O)c2cc(Br)nn2-c2ncccc2Cl)c(Br)cc2c1OC(F)(F)O2] | 209-211 |
| P.42 | 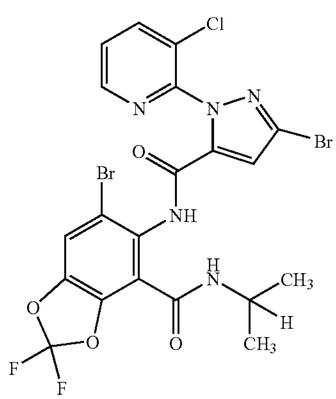 [SMILES: CC(C)NC(=O)c1c(NC(=O)c2cc(Br)nn2-c2ncccc2Cl)c(Br)cc2c1OC(F)(F)O2] | 158-160 |
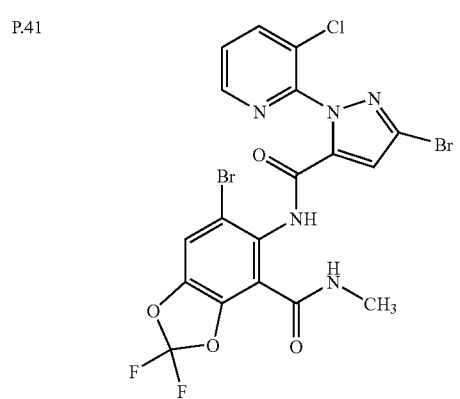
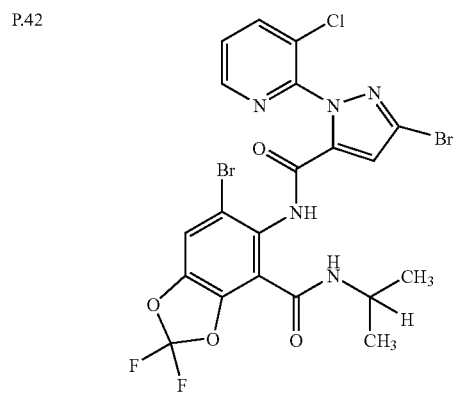
TABLE P-continued
Physical data of compounds of formula I:
| Compound No. | Structures | Melting Point °C. |
|---|---|---|
| P.43 | | 197-199 |
| P.44 | | 183-184 |
| P.45 | | 173-174 |

TABLE P-continued

Physical data of compounds of formula I:

| Compound No. | Structures | Melting Point ° C. |
|---|---|---|
| P.46 | 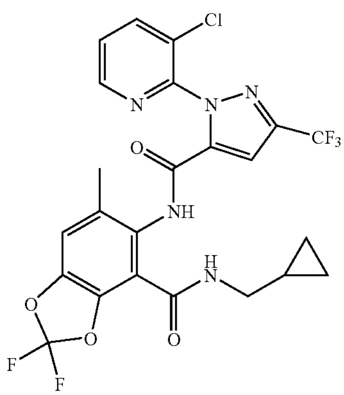 [SMILES: Cc1cc2c(c(C(=O)NCC3CC3)c1NC(=O)c1cc(C(F)(F)F)nn1-c1ncccc1Cl)OC(F)(F)O2] | 147-148 |
| P.47 | 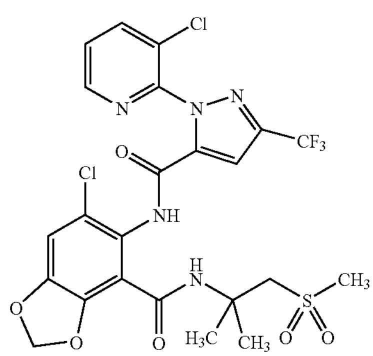 [SMILES: CC(C)(CS(C)(=O)=O)NC(=O)c1c(NC(=O)c2cc(C(F)(F)F)nn2-c2ncccc2Cl)c(Cl)cc2c1OCO2] | 88-90 |
| P.48 | (Example 4) | 204-205 |
| P.49 | (Example 5) | 98-99 |
| P.50 | (Example 6) | 198-199 |
| P.51 | | 205-207 |

TABLE P-continued

Physical data of compounds of formula I:

| Compound No. | Structures | Melting Point °C. |
|---|---|---|
| P.52 | (structure with 3-chloropyridyl-pyrazole-CF3, chloro-indane with hydroxyimino and N-isopropyl carboxamide) Example 7 | 188-190 |
| P.53 | (structure with 3-chloropyridyl-pyrazole-Br, chloro-indan-1-one with N-(1-cyclopropylcyclopropyl) carboxamide) | 123-125 |
| P.54 | (structure with 3-chloropyridyl-pyrazole-Br, chloro-1-hydroxyindane with N-isopropyl carboxamide) | 218-220 |
| P.55 | (structure with 3-chloropyridyl-pyrazole-Br, chloro-7-fluoroindane with N-(1-cyclopropylcyclopropyl) carboxamide) | 107-109 |
| P.56 | (structure with 3-chloropyridyl-pyrazole-Br, chloro-7-fluoroindane with N-isopropyl carboxamide) | 105-107 |
| P.57 | (structure with 3-chloropyridyl-pyrazole-OCH2CF3, chloro-benzodioxole with N-isopropyl carboxamide) | 201-203 |
| P.58 | (structure with 3-chloropyridyl-pyrazole-OCH2CF3, chloro-benzodioxole with N-ethyl carboxamide) | 205-207 |

TABLE P-continued

Physical data of compounds of formula I:

| Compound No. | Structures | Melting Point °C. |
|---|---|---|
| P.59 | (structure) | 217-218 |
| P.60 | (structure) | Waxy solid |
| P.61 | (structure) | 98-100 |
| P.62 | (structure) | 240-242 |
| P.63 | (structure) | 188-190 |
| P.64 | (structure) | 216-217 |
| P.65 | (structure) | 178-179 |

TABLE P-continued

Physical data of compounds of formula I:

| Compound No. | Structures | Melting Point °C. |
|---|---|---|
| P.66 | 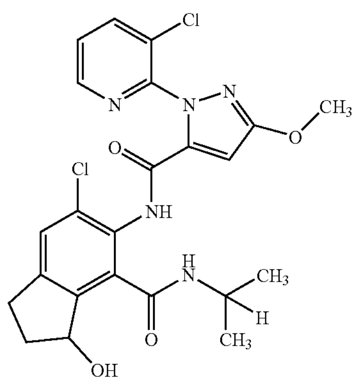 [SMILES: COc1cc(C(=O)Nc2c(Cl)cc3c(c2C(=O)NC(C)C)C(O)CC3)n(-c2ncccc2Cl)n1] | 148-150 |
| P.67 | 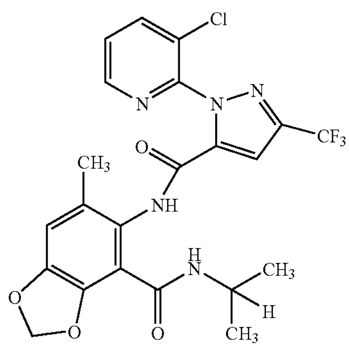 [SMILES: Cc1cc2c(c(C(=O)NC(C)C)c1NC(=O)c1cc(C(F)(F)F)nn1-c1ncccc1Cl)OCO2] | 133-135 |
| P.68 | 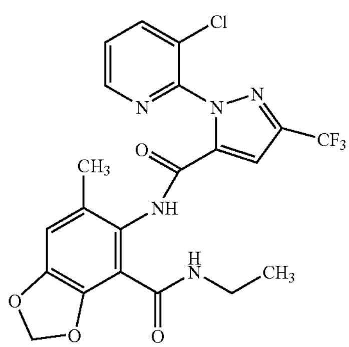 [SMILES: CCNC(=O)c1c(NC(=O)c2cc(C(F)(F)F)nn2-c2ncccc2Cl)c(C)cc2c1OCO2] | 225-227 |
| P.69 | 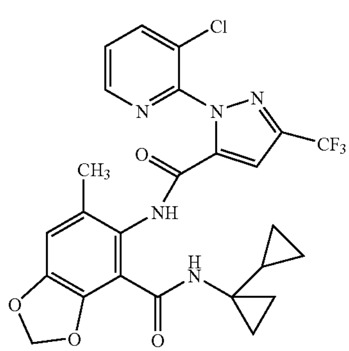 [SMILES: Cc1cc2c(c(C(=O)NC3(C4CC4)CC3)c1NC(=O)c1cc(C(F)(F)F)nn1-c1ncccc1Cl)OCO2] | 215-217 |
| P.70 | | 220-224 |
| P.71 | | 108-109 |
| P.72 | | 200-201 |
| P.73 | | 203-204 |

TABLE P-continued

Physical data of compounds of formula I:

| Compound No. | Structures | Melting Point °C. |
|---|---|---|
| P.74 | 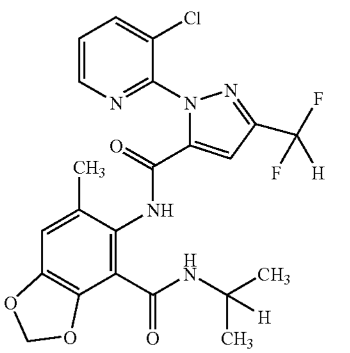 [SMILES: Cc1cc2c(c(C(=O)NC(C)C)c1NC(=O)c1cc(C(F)F)nn1-c1ncccc1Cl)OCO2] | 119-120 |
| P.75 | 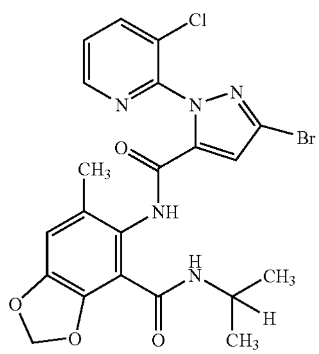 [SMILES: Cc1cc2c(c(C(=O)NC(C)C)c1NC(=O)c1cc(Br)nn1-c1ncccc1Cl)OCO2] | 135-137 |
| P.76 | 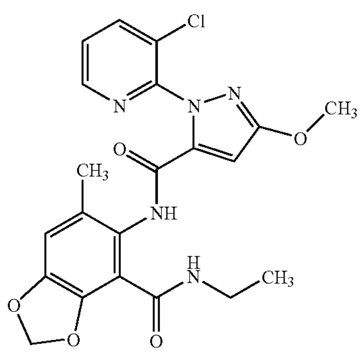 [SMILES: CCNC(=O)c1c(NC(=O)c2cc(OC)nn2-c2ncccc2Cl)c(C)cc2c1OCO2] | 72-74 |
| P.77 | 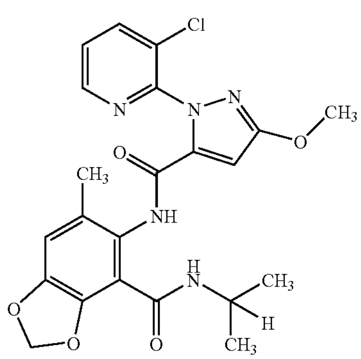 [SMILES: COc1cc(C(=O)Nc2c(C)cc3c(c2C(=O)NC(C)C)OCO3)n(-c2ncccc2Cl)n1] | 95-97 |
| P.78 | | 104-106 |
| P.79 | | 236-237 |
| P.80 | | 203-204 |
| P.81 | | 205-206 |

TABLE P-continued

Physical data of compounds of formula I:

| Compound No. | Structures | Melting Point °C |
|---|---|---|
| P.82 | | 140-142 |
| P.83 | | 212-214 |
| P.84 | | 170-172 |
| P.85 | 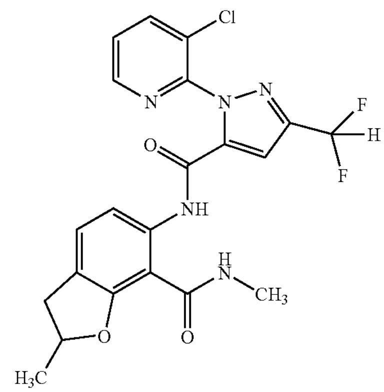 [SMILES: CNC(=O)c1c(NC(=O)c2cc(C(F)F)nn2-c2ncccc2Cl)ccc2c1OC(C)C2] | 211-213 |
| P.86 | 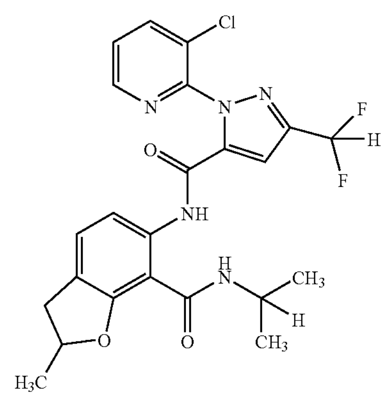 [SMILES: CC(C)NC(=O)c1c(NC(=O)c2cc(C(F)F)nn2-c2ncccc2Cl)ccc2c1OC(C)C2] | 169-170 |
| P.87 | 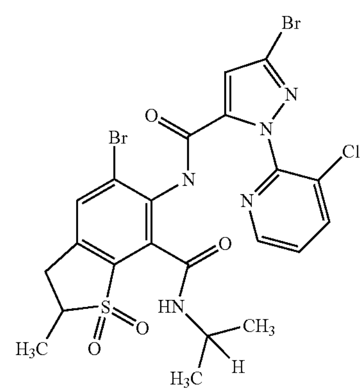 [SMILES: CC(C)NC(=O)c1c(NC(=O)c2cc(Br)nn2-c2ncccc2Cl)c(Br)cc2c1S(=O)(=O)C(C)C2] | 152-154 |
| P.88 | 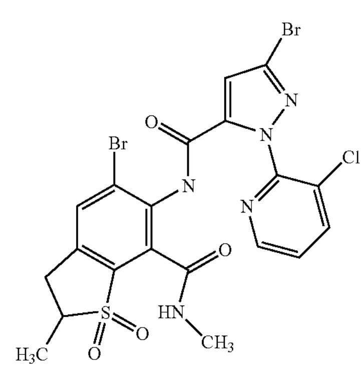 [SMILES: CNC(=O)c1c(NC(=O)c2cc(Br)nn2-c2ncccc2Cl)c(Br)cc2c1S(=O)(=O)C(C)C2] | 110-112 |

The compounds according to the following tables can be prepared analogously. The examples which follow are intended to illustrate the invention and show preferred compounds of formula I.

TABLE A

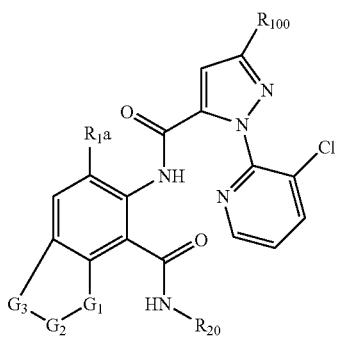

(Ib)

Compounds of formula Ib:

| Line | R₁a | R₁₀₀ | R₂₀ |
|---|---|---|---|
| A.1.1 | CH₃ | CF₃ | H |
| A.1.2 | CH₃ | CF₃ | CH₃ |
| A.1.3 | CH₃ | CF₃ | CH₂CH₃ |
| A.1.4 | CH₃ | CF₃ | CH(CH₃)CH₃ |
| A.1.5 | CH₃ | CF₃ | C(CH₃)(CH₃)CH₃ |
| A.1.6 | CH₃ | CF₃ |  |
| A.1.7 | CH₃ | CF₃ |  |
| A.1.8 | CH₃ | CF₃ |  |
| A.1.9 | CH₃ | CF₃ |  |
| A.1.10 | CH₃ | CF₃ | CH(CH₃)₂CH₂SCH₃ |
| A.1.11 | CH₃ | CF₃ | CH(CH₃)₂CH₂S(O)CH₃ |
| A.1.12 | CH₃ | CF₃ | CH(CH₃)₂CH₂S(O)₂CH₃ |
| A.1.13 | CH₃ | CF₃ | CH(CH₃)₂CH₂S(O)(NH)CH₃ |
| A.1.14 | CH₃ | CF₃ | 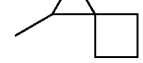 |
| A.1.15 | CH₃ | CF₃ | 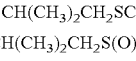 |
| A.1.16 | CH₃ | OCH₂CF₃ | H |
| A.1.17 | CH₃ | OCH₂CF₃ | CH₃ |
| A.1.18 | CH₃ | OCH₂CF₃ | CH₂CH₃ |
| A.1.19 | CH₃ | OCH₂CF₃ | CH(CH₃)CH₃ |
| A.1.20 | CH₃ | OCH2CF₃ | C(CH₃)(CH₃)CH₃ |

TABLE A-continued

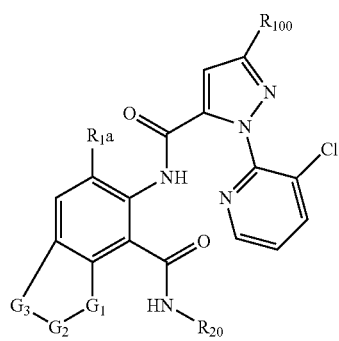

(Ib)

Compounds of formula Ib:

| Line | R₁a | R₁₀₀ | R₂₀ |
|---|---|---|---|
| A.1.21 | CH₃ | OCH₂CF₃ | 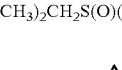 |
| A.1.22 | CH₃ | OCH₂CF₃ | 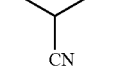 |
| A.1.23 | CH₃ | OCH₂CF₃ |  |
| A.1.24 | CH₃ | OCH₂CF₃ | 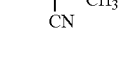 |
| A.1.25 | CH₃ | OCH₂CF₃ | CH(CH₃)₂CH₂SCH₃ |
| A.1.26 | CH₃ | OCH₂CF₃ | CH(CH₃)₂CH₂S(O)CH₃ |
| A.1.27 | CH₃ | OCH₂CF₃ | CH(CH₃)₂CH₂S(O)₂CH₃ |
| A.1.28 | CH₃ | OCH₂CF₃ | CH(CH₃)₂CH₂S(O)(NH)CH₃ |
| A.1.29 | CH₃ | OCH₂CF₃ |  |
| A.1.30 | CH₃ | OCH₂CF₃ |  |
| A.1.31 | CH₃ | Br | H |
| A.1.32 | CH₃ | Br | CH₃ |
| A.1.33 | CH₃ | Br | CH₂CH₃ |
| A.1.34 | CH₃ | Br | CH(CH₃)CH₃ |
| A.1.35 | CH₃ | Br | C(CH₃)(CH₃)CH₃ |

TABLE A-continued

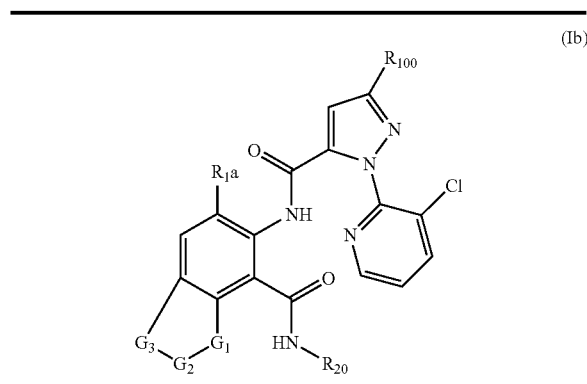

Compounds of formula Ib:

| Line | $R_1a$ | $R_{100}$ | $R_{20}$ |
|---|---|---|---|
| A.1.36 | $CH_3$ | Br | (cyclopropylmethyl) |
| A.1.37 | $CH_3$ | Br | (bicyclopropyl) |
| A.1.38 | $CH_3$ | Br | (methylbicyclopropyl) |
| A.1.39 | $CH_3$ | Br | (methyl cyclopropyl-cyclobutyl spiro) |
| A.1.40 | $CH_3$ | Br | $CH(CH_3)_2CH_2SCH_3$ |
| A.1.41 | $CH_3$ | Br | $CH(CH_3)_2CH_2S(O)CH_3$ |
| A.1.42 | $CH_3$ | Br | $CH(CH_3)_2CH_2S(O)_2CH_3$ |
| A.1.43 | $CH_3$ | Br | $CH(CH_3)_2CH_2S(O)(NH)CH_3$ |
| A.1.44 | $CH_3$ | Br | (cyclopropyl-CH(CN)-) |
| A.1.45 | $CH_3$ | Br | (cyclopropyl-C(CH_3)(CN)-) |
| A.1.46 | $CH_3$ | Cl | H |
| A.1.47 | $CH_3$ | Cl | $CH_3$ |
| A.1.48 | $CH_3$ | Cl | $CH_2CH_3$ |
| A.1.49 | $CH_3$ | Cl | $CH(CH_3)CH_3$ |
| A.1.50 | $CH_3$ | Cl | $C(CH_3)(CH_3)CH_3$ |
| A.1.51 | $CH_3$ | Cl | (cyclopropylmethyl) |
| A.1.52 | $CH_3$ | Cl | (bicyclopropyl) |

TABLE A-continued

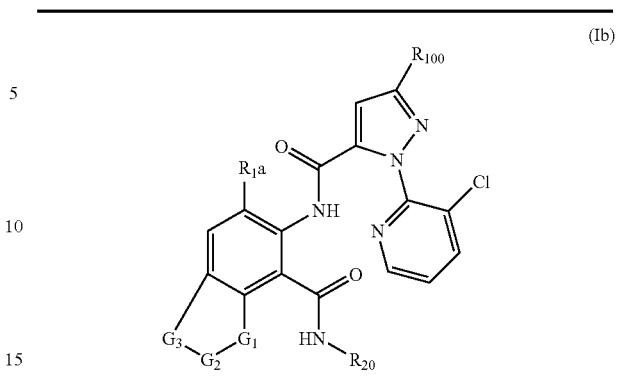

Compounds of formula Ib:

| Line | $R_1a$ | $R_{100}$ | $R_{20}$ |
|---|---|---|---|
| A.1.53 | $CH_3$ | Cl | (methylbicyclopropyl) |
| A.1.54 | $CH_3$ | Cl | (methyl cyclopropyl-cyclobutyl spiro) |
| A.1.55 | $CH_3$ | Cl | $CH(CH_3)_2CH_2SCH_3$ |
| A.1.56 | $CH_3$ | Cl | $CH(CH_3)_2CH_2S(O)CH_3$ |
| A.1.57 | $CH_3$ | Cl | $CH(CH_3)_2CH_2S(O)_2CH_3$ |
| A.1.58 | $CH_3$ | Cl | $CH(CH_3)_2CH_2S(O)(NH)CH_3$ |
| A.1.59 | $CH_3$ | Cl | (cyclopropyl-CH(CN)-) |
| A.1.60 | $CH_3$ | Cl | (cyclopropyl-C(CH_3)(CN)-) |
| A.1.61 | $CH_3$ | $CF_2H$ | H |
| A.1.62 | $CH_3$ | $CF_2H$ | $CH_3$ |
| A.1.63 | $CH_3$ | $CF_2H$ | $CH_2CH_3$ |
| A.1.64 | $CH_3$ | $CF_2H$ | $CH(CH_3)CH_3$ |
| A.1.65 | $CH_3$ | $CF_2H$ | $C(CH_3)(CH_3)CH_3$ |
| A.1.66 | $CH_3$ | $CF_2H$ | (cyclopropylmethyl) |
| A.1.67 | $CH_3$ | $CF_2H$ | (bicyclopropyl) |
| A.1.68 | $CH_3$ | $CF_2H$ | (methylbicyclopropyl) |
| A.1.69 | $CH_3$ | $CF_2H$ | (methyl cyclopropyl-cyclobutyl spiro) |
| A.1.70 | $CH_3$ | $CF_2H$ | $CH(CH_3)_2CH_2SCH_3$ |
| A.1.71 | $CH_3$ | $CF_2H$ | $CH(CH_3)_2CH_2S(O)CH_3$ |
| A.1.72 | $CH_3$ | $CF_2H$ | $CH(CH_3)_2CH_2S(O)_2CH_3$ |

TABLE A-continued

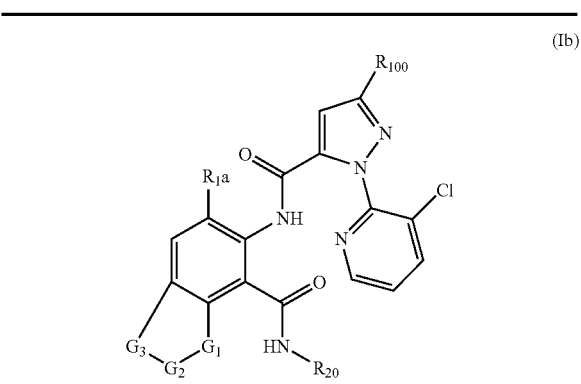

(Ib)

Compounds of formula Ib:

| Line | R₁a | R₁₀₀ | R₂₀ |
|---|---|---|---|
| A.1.73 | CH₃ | CF₂H | CH(CH₃)₂CH₂S(O)(NH)CH₃ |
| A.1.74 | CH₃ | CF₂H | 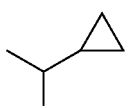 |
| A.1.75 | CH₃ | CF₂H | 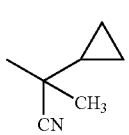 |
| A.1.76 | CH₃ | OCF₃ | H |
| A.1.77 | CH₃ | OCF₃ | CH₃ |
| A.1.78 | CH₃ | OCF₃ | CH₂CH₃ |
| A.1.79 | CH₃ | OCF₃ | CH(CH₃)CH₃ |
| A.1.80 | CH₃ | OCF₃ | C(CH₃)(CH₃)CH₃ |
| A.1.81 | CH₃ | OCF₃ | 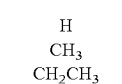 |
| A.1.82 | CH₃ | OCF₃ | 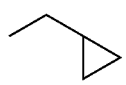 |
| A.1.83 | CH₃ | OCF₃ |  |
| A.1.84 | CH₃ | OCF₃ | 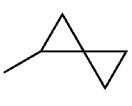 |
| A.1.85 | CH₃ | OCF₃ | CH(CH₃)₂CH₂SCH₃ |
| A.1.86 | CH₃ | OCF₃ | CH(CH₃)₂CH₂S(O)CH₃ |
| A.1.87 | CH₃ | OCF₃ | CH(CH₃)₂CH₂S(O)₂CH₃ |
| A.1.88 | CH₃ | OCF₃ | CH(CH₃)₂CH₂S(O)(NH)CH₃ |
| A.1.89 | CH₃ | OCF₃ | 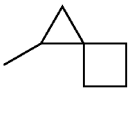 |
| A.1.90 | CH₃ | OCF₃ | 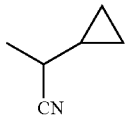 |
| A.1.91 | Cl | CF₃ | H |
| A.1.92 | Cl | CF₃ | CH₃ |
| A.1.93 | Cl | CF₃ | CH₂CH₃ |
| A.1.94 | Cl | CF₃ | CH(CH₃)CH₃ |
| A.1.95 | Cl | CF₃ | C(CH₃)(CH₃)CH₃ |
| A.1.96 | Cl | CF₃ | 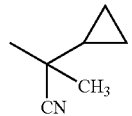 |
| A.1.97 | Cl | CF₃ | 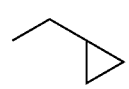 |
| A.1.98 | Cl | CF₃ |  |
| A.1.99 | Cl | CF₃ |  |
| A.1.100 | Cl | CF₃ | CH(CH₃)₂CH₂SCH₃ |
| A.1.101 | Cl | CF₃ | CH(CH₃)₂CH₂S(O)CH₃ |
| A.1.102 | Cl | CF₃ | CH(CH₃)₂CH₂S(O)₂CH₃ |
| A.1.103 | Cl | CF₃ | CH(CH₃)₂CH₂S(O)(NH)CH₃ |
| A.1.104 | Cl | CF₃ | 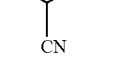 |
| A.1.105 | Cl | CF₃ |  |
| A.1.106 | Cl | OCH₂CF₃ | H |
| A.1.107 | Cl | OCH₂CF₃ | CH₃ |
| A.1.108 | Cl | OCH₂CF₃ | CH₂CH₃ |
| A.1.109 | Cl | OCH₂CF₃ | CH(CH₃)CH₃ |
| A.1.110 | Cl | OCH₂CF₃ | C(CH₃)(CH₃)CH₃ |

TABLE A-continued

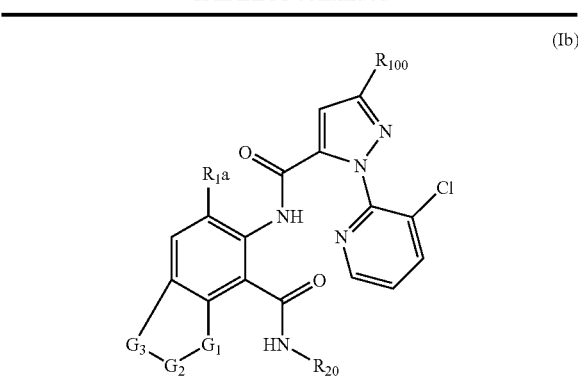

Compounds of formula Ib:

| Line | $R_1a$ | $R_{100}$ | $R_{20}$ |
|---|---|---|---|
| A.1.111 | Cl | $OCH_2CF_3$ | |
| A.1.112 | Cl | $OCH_2CF_3$ | |
| A.1.113 | Cl | $OCH_2CF_3$ | |
| A.1.114 | Cl | $OCH_2CF_3$ | |
| A.1.115 | Cl | $OCH_2CF_3$ | $CH(CH_3)_2CH_2SCH_3$ |
| A.1.116 | Cl | $OCH_2CF_3$ | $CH(CH_3)_2CH_2S(O)CH_3$ |
| A.1.117 | Cl | $OCH_2CF_3$ | $CH(CH_3)_2CH_2S(O)_2CH_3$ |
| A.1.118 | Cl | $OCH_2CF_3$ | $CH(CH_3)_2CH_2S(O)(NH)CH_3$ |
| A.1.119 | Cl | $OCH_2CF_3$ | |
| A.1.120 | Cl | $OCH_2CF_3$ | |
| A.1.121 | Cl | Br | H |
| A.1.122 | Cl | Br | $CH_3$ |
| A.1.123 | Cl | Br | $CH_2CH_3$ |
| A.1.124 | Cl | Br | $CH(CH_3)CH_3$ |
| A.1.125 | Cl | Br | $C(CH_3)(CH_3)CH_3$ |
| A.1.126 | Cl | Br | |
| A.1.127 | Cl | Br | |

TABLE A-continued

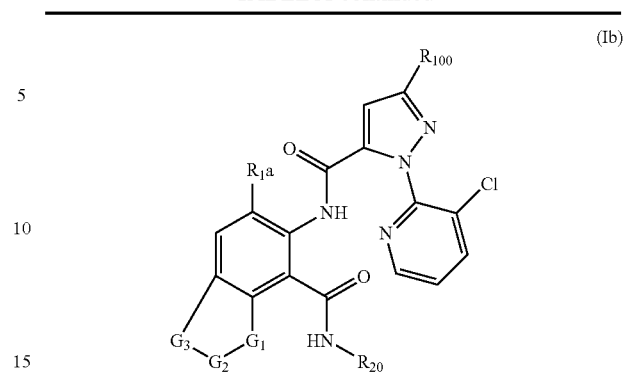

Compounds of formula Ib:

| Line | $R_1a$ | $R_{100}$ | $R_{20}$ |
|---|---|---|---|
| A.1.128 | Cl | Br | |
| A.1.129 | Cl | Br | |
| A.1.130 | Cl | Br | $CH(CH_3)_2CH_2SCH_3$ |
| A.1.131 | Cl | Br | $CH(CH_3)_2CH_2S(O)CH_3$ |
| A.1.132 | Cl | Br | $CH(CH_3)_2CH_2S(O)_2CH_3$ |
| A.1.133 | Cl | Br | $CH(CH_3)_2CH_2S(O)(NH)CH_3$ |
| A.1.134 | Cl | Br | |
| A.1.135 | Cl | Br | |
| A.1.137 | Cl | Cl | H |
| A.1.138 | Cl | Cl | $CH_3$ |
| A.1.139 | Cl | Cl | $CH_2CH_3$ |
| A.1.140 | Cl | Cl | $CH(CH_3)CH_3$ |
| A.1.141 | Cl | Cl | $C(CH_3)(CH_3)CH_3$ |
| A.1.142 | Cl | Cl | |
| A.1.143 | Cl | Cl | |
| A.1.144 | Cl | Cl | |
| A.1.145 | Cl | Cl | |
| A.1.146 | Cl | Cl | $CH(CH_3)_2CH_2SCH_3$ |
| A.1.147 | Cl | Cl | $CH(CH_3)_2CH_2S(O)CH_3$ |
| A.1.148 | Cl | Cl | $CH(CH_3)_2CH_2S(O)_2CH_3$ |

TABLE A-continued

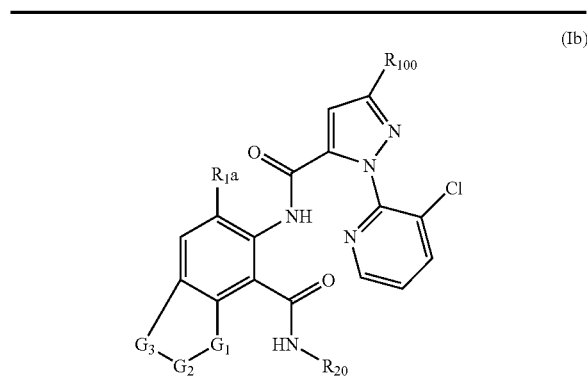

Compounds of formula Ib:

| Line | R₁a | R₁₀₀ | R₂₀ |
|---|---|---|---|
| A.1.149 | Cl | Cl | CH(CH₃)₂CH₂S(O)(NH)CH₃ |
| A.1.150 | Cl | Cl | (1-cyanoethyl)cyclopropyl |
| A.1.151 | Cl | Cl | 2-(cyclopropyl)-2-cyanopropyl (CH₃, CN) |
| A.1.152 | Cl | CF₂H | H |
| A.1.153 | Cl | CF₂H | CH₃ |
| A.1.154 | Cl | CF₂H | CH₂CH₃ |
| A.1.155 | Cl | CF₂H | CH(CH₃)CH₃ |
| A.1.156 | Cl | CF₂H | C(CH₃)(CH₃)CH₃ |
| A.1.157 | Cl | CF₂H | ethylcyclopropyl |
| A.1.158 | Cl | CF₂H | methyl-bicyclopropyl |
| A.1.159 | Cl | CF₂H | methyl-spiro[2.2]pentyl |
| A.1.160 | Cl | CF₂H | methyl-spiro[2.3]hexyl |
| A.1.161 | Cl | CF₂H | CH(CH₃)₂CH₂SCH₃ |
| A.1.162 | Cl | CF₂H | CH(CH₃)₂CH₂S(O)CH₃ |
| A.1.163 | Cl | CF₂H | CH(CH₃)₂CH₂S(O)₂CH₃ |
| A.1.164 | Cl | CF₂H | CH(CH₃)₂CH₂S(O)(NH)CH₃ |
| A.1.165 | Cl | CF₂H | (1-cyanoethyl)cyclopropyl |

TABLE A-continued

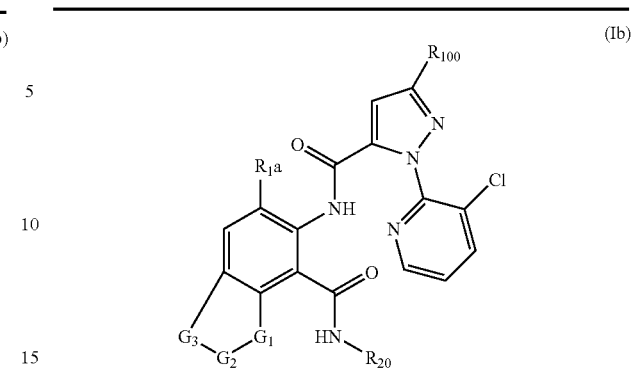

Compounds of formula Ib:

| Line | R₁a | R₁₀₀ | R₂₀ |
|---|---|---|---|
| A.1.166 | Cl | CF₂H | 2-(cyclopropyl)-2-cyanopropyl (CH₃, CN) |
| A.1.167 | Cl | OCF₃ | H |
| A.1.168 | Cl | OCF₃ | CH₃ |
| A.1.169 | Cl | OCF₃ | CH₂CH₃ |
| A.1.170 | Cl | OCF₃ | CH(CH₃)CH₃ |
| A.1.171 | Cl | OCF₃ | C(CH₃)(CH₃)CH₃ |
| A.1.172 | Cl | OCF₃ | ethylcyclopropyl |
| A.1.173 | Cl | OCF₃ | methyl-bicyclopropyl |
| A.1.174 | Cl | OCF₃ | methyl-spiro[2.2]pentyl |
| A.1.175 | Cl | OCF₃ | methyl-spiro[2.3]hexyl |
| A.1.176 | Cl | OCF₃ | CH(CH₃)₂CH₂SCH₃ |
| A.1.177 | Cl | OCF₃ | CH(CH₃)₂CH₂S(O)CH₃ |
| A.1.178 | Cl | OCF₃ | CH(CH₃)₂CH₂S(O)₂CH₃ |
| A.1.179 | Cl | OCF₃ | CH(CH₃)₂CH₂S(O)(NH)CH₃ |
| A.1.180 | Cl | OCF₃ | (1-cyanoethyl)cyclopropyl |
| A.1.181 | Cl | OCF₃ | 2-(cyclopropyl)-2-cyanopropyl (CH₃, CN) |
| A.1.182 | Br | CF₃ | H |
| A.1.183 | Br | CF₃ | CH₃ |
| A.1.184 | Br | CF₃ | CH₂CH₃ |
| A.1.185 | Br | CF₃ | CH(CH₃)CH₃ |
| A.1.186 | Br | CF₃ | C(CH₃)(CH₃)CH₃ |

TABLE A-continued

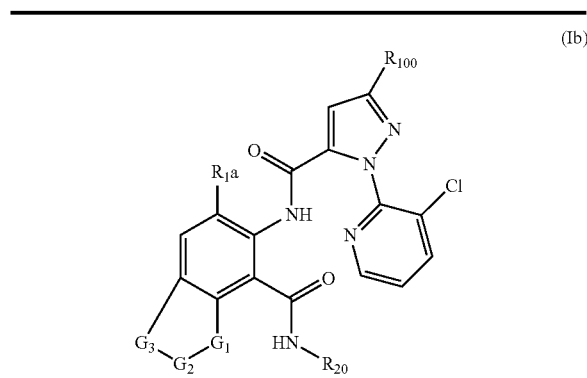

Compounds of formula Ib:

| Line | $R_1a$ | $R_{100}$ | $R_{20}$ |
|---|---|---|---|
| A.1.187 | Br | $CF_3$ | (cyclopropylmethyl) |
| A.1.188 | Br | $CF_3$ | (bicyclopropyl) |
| A.1.189 | Br | $CF_3$ | (methylbicyclopropyl) |
| A.1.190 | Br | $CF_3$ | (methyl-spiro cyclopropane-cyclobutane) |
| A.1.191 | Br | $CF_3$ | $CH(CH_3)_2CH_2SCH_3$ |
| A.1.192 | Br | $CF_3$ | $CH(CH_3)_2CH_2S(O)CH_3$ |
| A.1.193 | Br | $CF_3$ | $CH(CH_3)_2CH_2S(O)_2CH_3$ |
| A.1.194 | Br | $CF_3$ | $CH(CH_3)_2CH_2S(O)(NH)CH_3$ |
| A.1.195 | Br | $CF_3$ | (cyclopropyl-CH(CN)-) |
| A.1.196 | Br | $CF_3$ | (cyclopropyl-C(CH_3)(CN)-) |
| A.1.197 | Br | $OCH_2CF_3$ | H |
| A.1.198 | Br | $OCH_2CF_3$ | $CH_3$ |
| A.1.199 | Br | $OCH_2CF_3$ | $CH_2CH_3$ |
| A.1.200 | Br | $OCH_2CF_3$ | $CH(CH_3)CH_3$ |
| A.1.201 | Br | $OCH_2CF_3$ | $C(CH_3)(CH_3)CH_3$ |
| A.1.202 | Br | $OCH_2CF_3$ | (cyclopropylmethyl) |
| A.1.203 | Br | $OCH_2CF_3$ | (bicyclopropyl) |

TABLE A-continued

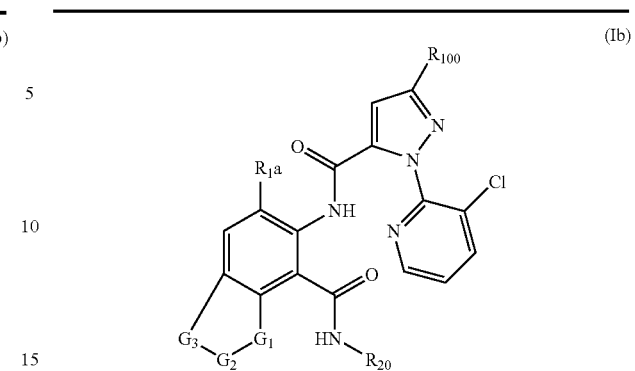

Compounds of formula Ib:

| Line | $R_1a$ | $R_{100}$ | $R_{20}$ |
|---|---|---|---|
| A.1.204 | Br | $OCH_2CF_3$ | (methylbicyclopropyl) |
| A.1.205 | Br | $OCH_2CF_3$ | (methyl-spiro cyclopropane-cyclobutane) |
| A.1.206 | Br | $OCH_2CF_3$ | $CH(CH_3)_2CH_2SCH_3$ |
| A.1.207 | Br | $OCH_2CF_3$ | $CH(CH_3)_2CH_2S(O)CH_3$ |
| A.1.208 | Br | $OCH_2CF_3$ | $CH(CH_3)_2CH_2S(O)_2CH_3$ |
| A.1.209 | Br | $OCH_2CF_3$ | $CH(CH_3)_2CH_2S(O)(NH)CH_3$ |
| A.1.210 | Br | $OCH_2CF_3$ | (cyclopropyl-CH(CN)-) |
| A.1.211 | Br | $OCH_2CF_3$ | (cyclopropyl-C(CH_3)(CN)-) |
| A.1.212 | Br | Br | H |
| A.1.213 | Br | Br | $CH_3$ |
| A.1.214 | Br | Br | $CH_2CH_3$ |
| A.1.215 | Br | Br | $CH(CH_3)CH_3$ |
| A.1.216 | Br | Br | $C(CH_3)(CH_3)CH_3$ |
| A.1.217 | Br | Br | (cyclopropylmethyl) |
| A.1.218 | Br | Br | (bicyclopropyl) |
| A.1.219 | Br | Br | (methylbicyclopropyl) |
| A.1.220 | Br | Br | (methyl-spiro cyclopropane-cyclobutane) |
| A.1.221 | Br | Br | $CH(CH_3)_2CH_2SCH_3$ |
| A.1.222 | Br | Br | $CH(CH_3)_2CH_2S(O)CH_3$ |
| A.1.223 | Br | Br | $CH(CH_3)_2CH_2S(O)_2CH_3$ |

TABLE A-continued

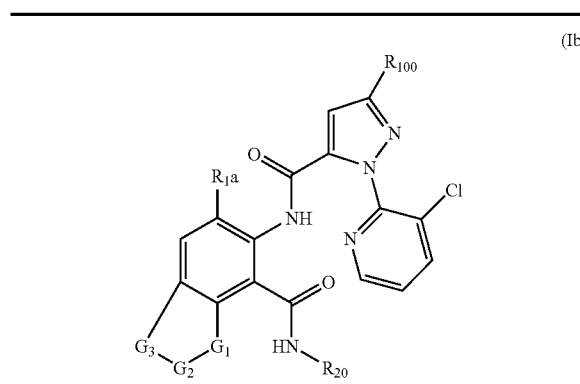

Compounds of formula Ib:

| Line | R₁a | R₁₀₀ | R₂₀ |
|---|---|---|---|
| A.1.224 | Br | Br | CH(CH₃)₂CH₂S(O)(NH)CH₃ |
| A.1.225 | Br | Br | (1-cyanoethyl)cyclopropyl |
| A.1.226 | Br | Br | (2-cyanopropan-2-yl)cyclopropyl |
| A.1.227 | Br | Cl | H |
| A.1.228 | Br | Cl | CH₃ |
| A.1.229 | Br | Cl | CH₂CH₃ |
| A.1.230 | Br | Cl | CH(CH₃)CH₃ |
| A.1.231 | Br | Cl | C(CH₃)(CH₃)CH₃ |
| A.1.232 | Br | Cl | cyclopropylmethyl |
| A.1.233 | Br | Cl | 1-methyl-bicyclopropyl |
| A.1.234 | Br | Cl | methyl-spiro[2.2]pentyl |
| A.1.235 | Br | Cl | methyl-spiro[2.3]hexyl |
| A.1.236 | Br | Cl | CH(CH₃)₂CH₂SCH₃ |
| A.1.237 | Br | Cl | CH(CH₃)₂CH₂S(O)CH₃ |
| A.1.238 | Br | Cl | CH(CH₃)₂CH₂S(O)₂CH₃ |
| A.1.239 | Br | Cl | CH(CH₃)₂CH₂S(O)(NH)CH₃ |
| A.1.240 | Br | Cl | (1-cyanoethyl)cyclopropyl |

TABLE A-continued

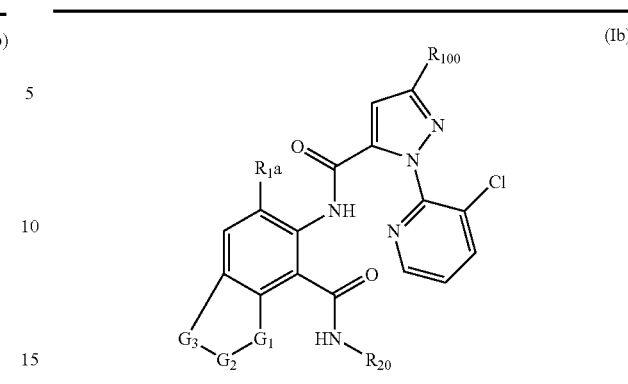

Compounds of formula Ib:

| Line | R₁a | R₁₀₀ | R₂₀ |
|---|---|---|---|
| A.1.241 | Br | Cl | (2-cyanopropan-2-yl)cyclopropyl |
| A.1.242 | Br | CF₂H | H |
| A.1.243 | Br | CF₂H | CH₃ |
| A.1.244 | Br | CF₂H | CH₂CH₃ |
| A.1.245 | Br | CF₂H | CH(CH₃)CH₃ |
| A.1.246 | Br | CF₂H | C(CH₃)(CH₃)CH₃ |
| A.1.247 | Br | CF₂H | cyclopropylmethyl |
| A.1.248 | Br | CF₂H | methyl-bicyclopropyl |
| A.1.249 | Br | CF₂H | methyl-spiro[2.2]pentyl |
| A.1.250 | Br | CF₂H | methyl-spiro[2.3]hexyl |
| A.1.251 | Br | CF₂H | CH(CH₃)₂CH₂SCH₃ |
| A.1.252 | Br | CF₂H | CH(CH₃)₂CH₂S(O)CH₃ |
| A.1.253 | Br | CF₂H | CH(CH₃)₂CH₂S(O)₂CH₃ |
| A.1.254 | Br | CF₂H | CH(CH₃)₂CH₂S(O)(NH)CH₃ |
| A.1.255 | Br | CF₂H | (1-cyanoethyl)cyclopropyl |
| A.1.256 | Br | CF₂H | (2-cyanopropan-2-yl)cyclopropyl |
| A.1.257 | Br | OCF₃ | H |
| A.1.258 | Br | OCF₃ | CH₃ |
| A.1.259 | Br | OCF₃ | CH₂CH₃ |
| A.1.260 | Br | OCF₃ | CH(CH₃)CH₃ |
| A.1.261 | Br | OCF₃ | C(CH₃)(CH₃)CH₃ |

TABLE A-continued

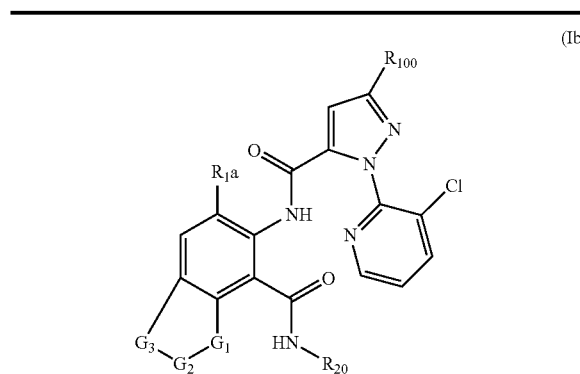

(Ib)

Compounds of formula Ib:

| Line | R₁a | R₁₀₀ | R₂₀ |
|---|---|---|---|
| A.1.262 | Br | OCF$_3$ | cyclopropylmethyl |
| A.1.263 | Br | OCF$_3$ | bicyclopropyl |
| A.1.264 | Br | OCF$_3$ | 1-methyl-bicyclopropyl |
| A.1.265 | Br | OCF$_3$ | 1-methyl-spiro[2.3]hexyl |
| A.1.266 | Br | OCF$_3$ | CH(CH$_3$)$_2$CH$_2$SCH$_3$ |
| A.1.267 | Br | OCF$_3$ | CH(CH$_3$)$_2$CH$_2$S(O)CH$_3$ |
| A.1.268 | Br | OCF$_3$ | CH(CH$_3$)$_2$CH$_2$S(O)$_2$CH$_3$ |
| A.1.269 | Br | OCF$_3$ | CH(CH$_3$)$_2$CH$_2$S(O)(NH)CH$_3$ |
| A.1.270 | Br | OCF$_3$ | 1-cyclopropyl-1-cyano-ethyl |
| A.1.271 | Br | OCF$_3$ | 1-cyclopropyl-1-methyl-1-cyano |
| A.1.272 | CN | CF$_3$ | H |
| A.1.273 | CN | CF$_3$ | CH$_3$ |
| A.1.274 | CN | CF$_3$ | CH$_2$CH$_3$ |
| A.1.275 | CN | CF$_3$ | CH(CH$_3$)CH$_3$ |
| A.1.276 | CN | CF$_3$ | C(CH$_3$)(CH$_3$)CH$_3$ |
| A.1.277 | CN | CF$_3$ | cyclopropylmethyl |
| A.1.278 | CN | CF$_3$ | bicyclopropyl |
| A.1.279 | CN | CF$_3$ | 1-methyl-bicyclopropyl |
| A.1.280 | CN | CF$_3$ | 1-methyl-spiro[2.3]hexyl |
| A.1.281 | CN | CF$_3$ | CH(CH$_3$)$_2$CH$_2$SCH$_3$ |
| A.1.282 | CN | CF$_3$ | CH(CH$_3$)$_2$CH$_2$S(O)CH$_3$ |
| A.1.283 | CN | CF$_3$ | CH(CH$_3$)$_2$CH$_2$S(O)$_2$CH$_3$ |
| A.1.284 | CN | CF$_3$ | CH(CH$_3$)$_2$CH$_2$S(O)(NH)CH$_3$ |
| A.1.285 | CN | CF$_3$ | 1-cyclopropyl-1-cyano-ethyl |
| A.1.286 | CN | CF$_3$ | 1-cyclopropyl-1-methyl-1-cyano |
| A.1.287 | CN | OCH$_2$CF$_3$ | H |
| A.1.288 | CN | OCH$_2$CF$_3$ | CH$_3$ |
| A.1.289 | CN | OCH$_2$CF$_3$ | CH$_2$CH$_3$ |
| A.1.290 | CN | OCH$_2$CF$_3$ | CH(CH$_3$)CH$_3$ |
| A.1.291 | CN | OCH$_2$CF$_3$ | C(CH$_3$)(CH$_3$)CH$_3$ |
| A.1.292 | CN | OCH$_2$CF$_3$ | cyclopropylmethyl |
| A.1.293 | CN | OCH$_2$CF$_3$ | 1-methyl-bicyclopropyl |
| A.1.294 | CN | OCH$_2$CF$_3$ | bicyclopropyl |
| A.1.295 | CN | OCH$_2$CF$_3$ | 1-methyl-spiro[2.3]hexyl |
| A.1.296 | CN | OCH$_2$CF$_3$ | CH(CH$_3$)$_2$CH$_2$SCH$_3$ |
| A.1.297 | CN | OCH$_2$CF$_3$ | CH(CH$_3$)$_2$CH$_2$S(O)CH$_3$ |
| A.1.298 | CN | OCH$_2$CF$_3$ | CH(CH$_3$)$_2$CH$_2$S(O)$_2$CH$_3$ |

TABLE A-continued

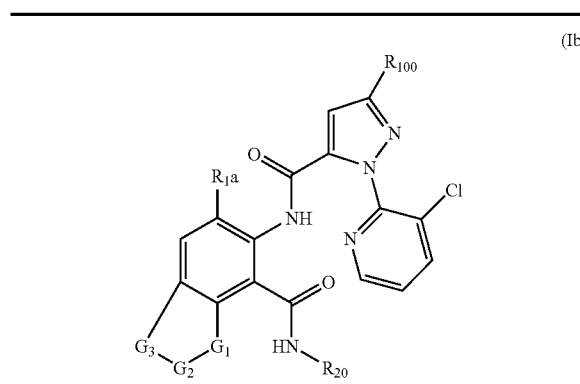

Compounds of formula Ib:

| Line | $R_1a$ | $R_{100}$ | $R_{20}$ |
|---|---|---|---|
| A.1.299 | CN | $OCH_2CF_3$ | $CH(CH_3)_2CH_2S(O)(NH)CH_3$ |
| A.1.300 | CN | $OCH_2CF_3$ | ![cyclopropyl-CH(CN)-] |
| A.1.301 | CN | $OCH_2CF_3$ | ![cyclopropyl-C(CH_3)(CN)-] |
| A.1.302 | CN | Br | H |
| A.1.303 | CN | Br | $CH_3$ |
| A.1.304 | CN | Br | $CH_2CH_3$ |
| A.1.305 | CN | Br | $CH(CH_3)CH_3$ |
| A.1.306 | CN | Br | $C(CH_3)(CH_3)CH_3$ |
| A.1.307 | CN | Br | ![cyclopropylmethyl] |
| A.1.308 | CN | Br | ![bicyclopropyl] |
| A.1.309 | CN | Br | ![spiro] |
| A.1.310 | CN | Br | ![spiro cyclobutyl] |
| A.1.311 | CN | Br | $CH(CH_3)_2CH_2SCH_3$ |
| A.1.312 | CN | Br | $CH(CH_3)_2CH_2S(O)CH_3$ |
| A.1.313 | CN | Br | $CH(CH_3)_2CH_2S(O)_2CH_3$ |
| A.1.314 | CN | Br | $CH(CH_3)_2CH_2S(O)(NH)CH_3$ |
| A.1.315 | CN | Br | ![cyclopropyl-CH(CN)-] |
| A.1.316 | CN | Br | ![cyclopropyl-C(CH_3)(CN)-] |
| A.1.317 | CN | Cl | H |
| A.1.318 | CN | Cl | $CH_3$ |
| A.1.319 | CN | Cl | $CH_2CH_3$ |
| A.1.320 | CN | Cl | $CH(CH_3)CH_3$ |
| A.1.321 | CN | Cl | $C(CH_3)(CH_3)CH_3$ |
| A.1.322 | CN | Cl | ![cyclopropylmethyl] |
| A.1.323 | CN | Cl | ![bicyclopropyl] |
| A.1.324 | CN | Cl | ![spiro] |
| A.1.325 | CN | Cl | ![spiro cyclobutyl] |
| A.1.326 | CN | Cl | $CH(CH_3)_2CH_2SCH_3$ |
| A.1.327 | CN | Cl | $CH(CH_3)_2CH_2S(O)CH_3$ |
| A.1.328 | CN | Cl | $CH(CH_3)_2CH_2S(O)_2CH_3$ |
| A.1.329 | CN | Cl | $CH(CH_3)_2CH_2S(O)(NH)CH_3$ |
| A.1.330 | CN | Cl | ![cyclopropyl-CH(CN)-] |
| A.1.331 | CN | Cl | ![cyclopropyl-C(CH_3)(CN)-] |
| A.1.332 | CN | $CF_2H$ | H |
| A.1.333 | CN | $CF_2H$ | $CH_3$ |
| A.1.334 | CN | $CF_2H$ | $CH_2CH_3$ |
| A.1.335 | CN | $CF_2H$ | $CH(CH_3)CH_3$ |
| A.1.336 | CN | $CF_2H$ | $C(CH_3)(CH_3)CH_3$ |

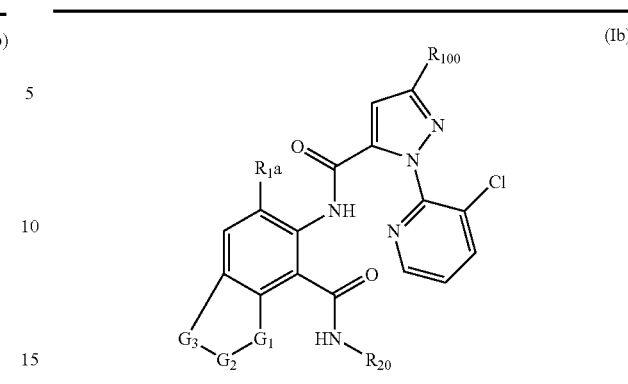

TABLE A-continued

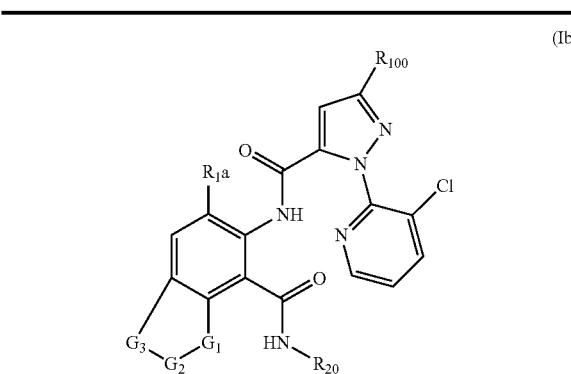

Compounds of formula Ib:

| Line | R₁a | R₁₀₀ | R₂₀ |
|---|---|---|---|
| A.1.337 | CN | $CF_2H$ | cyclopropyl |
| A.1.338 | CN | $CF_2H$ | bicyclopropyl |
| A.1.339 | CN | $CF_2H$ | methylbicyclopropyl |
| A.1.340 | CN | $CF_2H$ | methyl-spiro[2.3]hexyl |
| A.1.341 | CN | $CF_2H$ | $CH(CH_3)_2CH_2SCH_3$ |
| A.1.342 | CN | $CF_2H$ | $CH(CH_3)_2CH_2S(O)CH_3$ |
| A.1.343 | CN | $CF_2H$ | $CH(CH_3)_2CH_2S(O)_2CH_3$ |
| A.1.344 | CN | $CF_2H$ | $CH(CH_3)_2CH_2S(O)(NH)CH_3$ |
| A.1.345 | CN | $CF_2H$ | cyclopropyl-CH(CN)- |
| A.1.346 | CN | $CF_2H$ | cyclopropyl-C(CH₃)(CN)- |
| A.1.347 | CN | $OCF_3$ | H |
| A.1.348 | CN | $OCF_3$ | $CH_3$ |
| A.1.349 | CN | $OCF_3$ | $CH_2CH_3$ |
| A.1.350 | CN | $OCF_3$ | $CH(CH_3)CH_3$ |
| A.1.351 | CN | $OCF_3$ | $C(CH_3)(CH_3)CH_3$ |
| A.1.352 | CN | $OCF_3$ | cyclopropylmethyl |
| A.1.353 | CN | $OCF_3$ | bicyclopropyl |
| A.1.354 | CN | $OCF_3$ | methylbicyclopropyl |
| A.1.355 | CN | $OCF_3$ | methyl-spiro[2.3]hexyl |
| A.1.356 | CN | $OCF_3$ | $CH(CH_3)_2CH_2SCH_3$ |
| A.1.357 | CN | $OCF_3$ | $CH(CH_3)_2CH_2S(O)CH_3$ |
| A.1.358 | CN | $OCF_3$ | $CH(CH_3)_2CH_2S(O)_2CH_3$ |
| A.1.359 | CN | $OCF_3$ | $CH(CH_3)_2CH_2S(O)(NH)CH_3$ |
| A.1.360 | CN | $OCF_3$ | cyclopropyl-CH(CN)- |
| A.1.361 | CN | $OCF_3$ | cyclopropyl-C(CH₃)(CN)- |
| A.1.362 | I | $CF_3$ | H |
| A.1.363 | I | $CF_3$ | $CH_3$ |
| A.1.364 | I | $CF_3$ | $CH_2CH_3$ |
| A.1.365 | I | $CF_3$ | $CH(CH_3)CH_3$ |
| A.1.366 | I | $CF_3$ | $C(CH_3)(CH_3)CH_3$ |
| A.1.367 | I | $CF_3$ | cyclopropylmethyl |
| A.1.368 | I | $CF_3$ | bicyclopropyl |
| A.1.369 | I | $CF_3$ | methylbicyclopropyl |
| A.1.370 | I | $CF_3$ | methyl-spiro[2.3]hexyl |
| A.1.371 | I | $CF_3$ | $CH(CH_3)_2CH_2SCH_3$ |
| A.1.372 | I | $CF_3$ | $CH(CH_3)_2CH_2S(O)CH_3$ |
| A.1.373 | I | $CF_3$ | $CH(CH_3)_2CH_2S(O)_2CH_3$ |
| A.1.374 | I | $CF_3$ | $CH(CH_3)_2CH_2S(O)(NH)CH_3$ |

TABLE A-continued

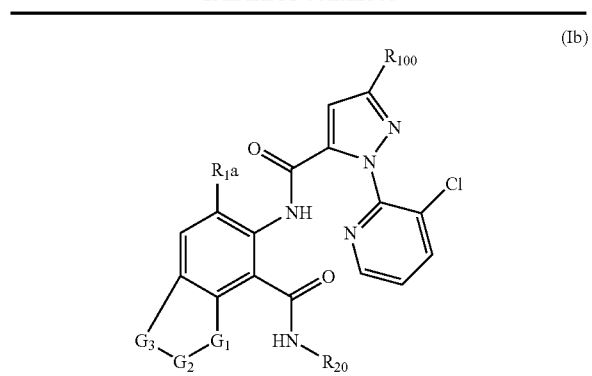

Compounds of formula Ib:

| Line | R₁a | R₁₀₀ | R₂₀ |
|---|---|---|---|
| A.1.375 | I | CF₃ | (1-cyanoethyl)cyclopropyl |
| A.1.376 | I | CF₃ | 2-cyano-2-cyclopropylpropyl (CH₃, CN) |
| A.1.377 | I | OCH₂CF₃ | H |
| A.1.378 | I | OCH₂CF₃ | CH₃ |
| A.1.379 | I | OCH₂CF₃ | CH₂CH₃ |
| A.1.380 | I | OCH₂CF₃ | CH(CH₃)CH₃ |
| A.1.381 | I | OCH₂CF₃ | C(CH₃)(CH₃)CH₃ |
| A.1.382 | I | OCH₂CF₃ | cyclopropylmethyl |
| A.1.383 | I | OCH₂CF₃ | bicyclopropyl |
| A.1.384 | I | OCH₂CF₃ | spiro[2.2]pentyl |
| A.1.385 | I | OCH₂CF₃ | spiro[2.3]hexyl |
| A.1.386 | I | OCH₂CF₃ | CH(CH₃)₂CH₂SCH₃ |
| A.1.387 | I | OCH₂CF₃ | CH(CH₃)₂CH₂S(O)CH₃ |
| A.1.388 | I | OCH₂CF₃ | CH(CH₃)₂CH₂S(O)₂CH₃ |
| A.1.389 | I | OCH₂CF₃ | CH(CH₃)₂CH₂S(O)(NH)CH₃ |
| A.1.390 | I | OCH₂CF₃ | (1-cyanoethyl)cyclopropyl |
| A.1.391 | I | OCH₂CF₃ | 2-cyano-2-cyclopropylpropyl |

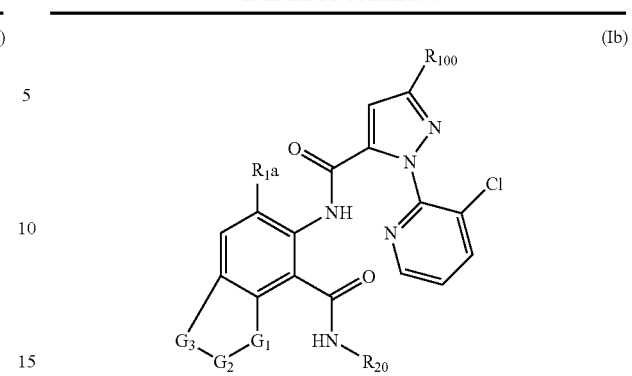

Compounds of formula Ib:

| Line | R₁a | R₁₀₀ | R₂₀ |
|---|---|---|---|
| A.1.392 | I | Br | H |
| A.1.393 | I | Br | CH₃ |
| A.1.394 | I | Br | CH₂CH₃ |
| A.1.395 | I | Br | CH(CH₃)CH₃ |
| A.1.396 | I | Br | C(CH₃)(CH₃)CH₃ |
| A.1.397 | I | Br | cyclopropylmethyl |
| A.1.398 | I | Br | bicyclopropyl |
| A.1.399 | I | Br | spiro[2.2]pentyl |
| A.1.400 | I | Br | spiro[2.3]hexyl |
| A.1.401 | I | Br | CH(CH₃)₂CH₂SCH₃ |
| A.1.402 | I | Br | CH(CH₃)₂CH₂S(O)CH₃ |
| A.1.403 | I | Br | CH(CH₃)₂CH₂S(O)₂CH₃ |
| A.1.404 | I | Br | CH(CH₃)₂CH₂S(O)(NH)CH₃ |
| A.1.405 | I | Br | (1-cyanoethyl)cyclopropyl |
| A.1.406 | I | Br | 2-cyano-2-cyclopropylpropyl |
| A.1.407 | I | Cl | H |
| A.1.408 | I | Cl | CH₃ |
| A.1.409 | I | Cl | CH₂CH₃ |
| A.1.410 | I | Cl | CH(CH₃)CH₃ |
| A.1.411 | I | Cl | C(CH₃)(CH₃)CH₃ |
| A.1.412 | I | Cl | cyclopropylmethyl |

TABLE A-continued

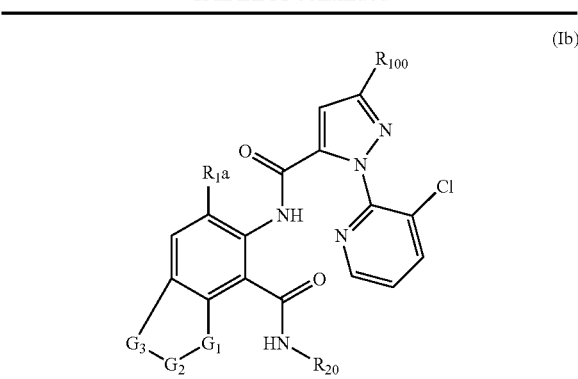

Compounds of formula Ib:

| Line | R₁a | R₁₀₀ | R₂₀ |
|---|---|---|---|
| A.1.413 | I | Cl | (cyclopropyl-cyclopropyl methyl) |
| A.1.414 | I | Cl | (spiro[2.2]pentyl methyl) |
| A.1.415 | I | Cl | (spiro[2.3]hexyl methyl) |
| A.1.416 | I | Cl | CH(CH₃)₂CH₂SCH₃ |
| A.1.417 | I | Cl | CH(CH₃)₂CH₂S(O)CH₃ |
| A.1.418 | I | Cl | CH(CH₃)₂CH₂S(O)₂CH₃ |
| A.1.419 | I | Cl | CH(CH₃)₂CH₂S(O)(NH)CH₃ |
| A.1.420 | I | Cl | (1-cyclopropyl-1-cyano ethyl) |
| A.1.421 | I | Cl | (2-cyclopropyl-2-cyanopropyl) |
| A.1.422 | I | CF₂H | H |
| A.1.423 | I | CF₂H | CH₃ |
| A.1.424 | I | CF₂H | CH₂CH₃ |
| A.1.425 | I | CF₂H | CH(CH₃)CH₃ |
| A.1.426 | I | CF₂H | C(CH₃)(CH₃)CH₃ |
| A.1.427 | I | CF₂H | (cyclopropylmethyl) |
| A.1.428 | I | CF₂H | (cyclopropyl-cyclopropyl methyl) |
| A.1.429 | I | CF₂H | (spiro[2.2]pentyl methyl) |

TABLE A-continued

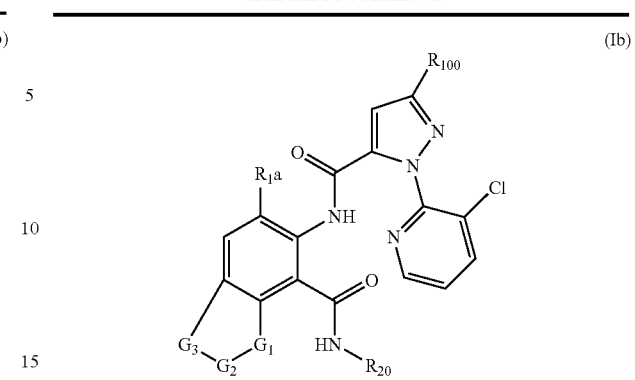

Compounds of formula Ib:

| Line | R₁a | R₁₀₀ | R₂₀ |
|---|---|---|---|
| A.1.430 | I | CF₂H | (spiro[2.3]hexyl methyl) |
| A.1.431 | I | CF₂H | CH(CH₃)₂CH₂SCH₃ |
| A.1.432 | I | CF₂H | CH(CH₃)₂CH₂S(O)CH₃ |
| A.1.433 | I | CF₂H | CH(CH₃)₂CH₂S(O)₂CH₃ |
| A.1.434 | I | CF₂H | CH(CH₃)₂CH₂S(O)(NH)CH₃ |
| A.1.435 | I | CF₂H | (1-cyclopropyl-1-cyano ethyl) |
| A.1.436 | I | CF₂H | (2-cyclopropyl-2-cyanopropyl) |
| A.1.437 | I | OCF₃ | H |
| A.1.438 | I | OCF₃ | CH₃ |
| A.1.439 | I | OCF₃ | CH₂CH₃ |
| A.1.440 | I | OCF₃ | CH(CH₃)CH₃ |
| A.1.441 | I | OCF₃ | C(CH₃)(CH₃)CH₃ |
| A.1.442 | I | OCF₃ | (cyclopropylmethyl) |
| A.1.443 | I | OCF₃ | (cyclopropyl-cyclopropyl methyl) |
| A.1.444 | I | OCF₃ | (spiro[2.2]pentyl methyl) |
| A.1.445 | I | OCF₃ | (spiro[2.3]hexyl methyl) |
| A.1.446 | I | OCF₃ | CH(CH₃)₂CH₂SCH₃ |
| A.1.447 | I | OCF₃ | CH(CH₃)₂CH₂S(O)CH₃ |
| A.1.448 | I | OCF₃ | CH(CH₃)₂CH₂S(O)₂CH₃ |
| A.1.449 | I | OCF₃ | CH(CH₃)₂CH₂S(O)(NH)CH₃ |

TABLE A-continued

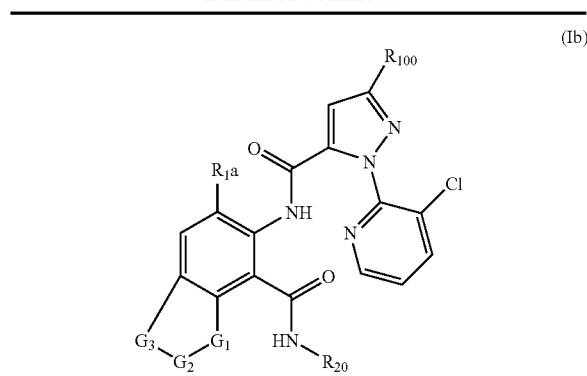

Compounds of formula Ib:

| Line | R₁a | R₁₀₀ | R₂₀ |
|---|---|---|---|
| A.1.450 | I | OCF₃ | (1-cyanoethyl-cyclopropyl) |
| A.1.451 | I | OCF₃ | (2-cyano-2-methyl-cyclopropyl) |
| A.1.452 | C≡CH | CF₃ | H |
| A.1.453 | C≡CH | CF₃ | CH₃ |
| A.1.454 | C≡CH | CF₃ | CH₂CH₃ |
| A.1.455 | C≡CH | CF₃ | CH(CH₃)CH₃ |
| A.1.456 | C≡CH | CF₃ | C(CH₃)(CH₃)CH₃ |
| A.1.457 | C≡CH | CF₃ | (methylcyclopropyl) |
| A.1.458 | C≡CH | CF₃ | (bicyclopropyl) |
| A.1.459 | C≡CH | CF₃ | (methylbicyclopropyl) |
| A.1.460 | C≡CH | CF₃ | (spiro cyclopropane-cyclobutane) |
| A.1.461 | C≡CH | CF₃ | CH(CH₃)₂CH₂SCH₃ |
| A.1.462 | C≡CH | CF₃ | CH(CH₃)₂CH₂S(O)CH₃ |
| A.1.463 | C≡CH | CF₃ | CH(CH₃)₂CH₂S(O)₂CH₃ |
| A.1.464 | C≡CH | CF₃ | CH(CH₃)₂CH₂S(O)(NH)CH₃ |
| A.1.465 | C≡CH | CF₃ | (1-cyanoethyl-cyclopropyl) |
| A.1.466 | C≡CH | CF₃ | (2-cyano-2-methyl-cyclopropyl) |

TABLE A-continued

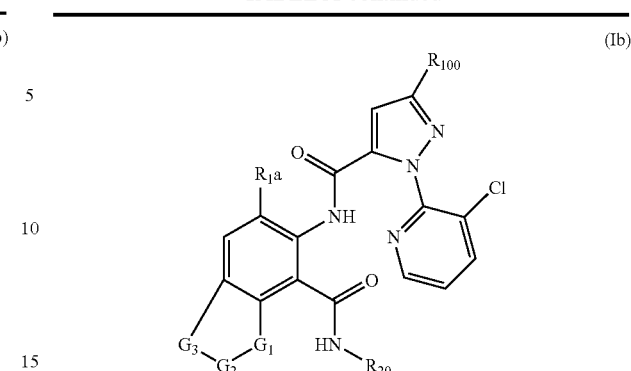

Compounds of formula Ib:

| Line | R₁a | R₁₀₀ | R₂₀ |
|---|---|---|---|
| A.1.467 | C≡CH | OCH₂CF₃ | H |
| A.1.468 | C≡CH | OCH₂CF₃ | CH₃ |
| A.1.469 | C≡CH | OCH₂CF₃ | CH₂CH₃ |
| A.1.470 | C≡CH | OCH₂CF₃ | CH(CH₃)CH₃ |
| A.1.471 | C≡CH | OCH₂CF₃ | C(CH₃)(CH₃)CH₃ |
| A.1.472 | C≡CH | OCH₂CF₃ | (methylcyclopropyl) |
| A.1.473 | C≡CH | OCH₂CF₃ | (bicyclopropyl) |
| A.1.474 | C≡CH | OCH₂CF₃ | (methylbicyclopropyl) |
| A.1.475 | C≡CH | OCH₂CF₃ | (spiro cyclopropane-cyclobutane) |
| A.1.476 | C≡CH | OCH₂CF₃ | CH(CH₃)₂CH₂SCH₃ |
| A.1.477 | C≡CH | OCH₂CF₃ | CH(CH₃)₂CH₂S(O)CH₃ |
| A.1.478 | C≡CH | OCH₂CF₃ | CH(CH₃)₂CH₂S(O)₂CH₃ |
| A.1.479 | C≡CH | OCH₂CF₃ | CH(CH₃)₂CH₂S(O)(NH)CH₃ |
| A.1.480 | C≡CH | OCH₂CF₃ | (1-cyanoethyl-cyclopropyl) |
| A.1.481 | C≡CH | OCH₂CF₃ | (2-cyano-2-methyl-cyclopropyl) |
| A.1.482 | C≡CH | Br | H |
| A.1.483 | C≡CH | Br | CH₃ |
| A.1.484 | C≡CH | Br | CH₂CH₃ |
| A.1.485 | C≡CH | Br | CH(CH₃)CH₃ |
| A.1.486 | C≡CH | Br | C(CH₃)(CH₃)CH₃ |
| A.1.487 | C≡CH | Br | (methylcyclopropyl) |

TABLE A-continued

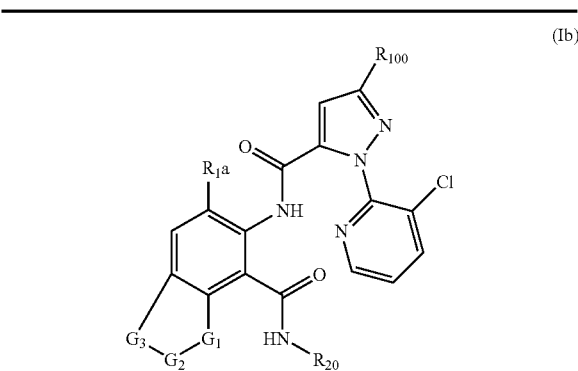

Compounds of formula Ib:

| Line | $R_1a$ | $R_{100}$ | $R_{20}$ |
|---|---|---|---|
| A.1.488 | C≡CH | Br | |
| A.1.489 | C≡CH | Br | |
| A.1.490 | C≡CH | Br | |
| A.1.491 | C≡CH | Br | $CH(CH_3)_2CH_2SCH_3$ |
| A.1.492 | C≡CH | Br | $CH(CH_3)_2CH_2S(O)CH_3$ |
| A.1.493 | C≡CH | Br | $CH(CH_3)_2CH_2S(O)_2CH_3$ |
| A.1.494 | C≡CH | Br | $CH(CH_3)_2CH_2S(O)(NH)CH_3$ |
| A.1.495 | C≡CH | Br | |
| A.1.496 | C≡CH | Br | |
| A.1.497 | C≡CH | Cl | H |
| A.1.498 | C≡CH | Cl | $CH_3$ |
| A.1.499 | C≡CH | Cl | $CH_2CH_3$ |
| A.1.500 | C≡CH | Cl | $CH(CH_3)CH_3$ |
| A.1.501 | C≡CH | Cl | $C(CH_3)(CH_3)CH_3$ |
| A.1.502 | C≡CH | Cl | |
| A.1.503 | C≡CH | Cl | |
| A.1.504 | C≡CH | Cl | |

TABLE A-continued

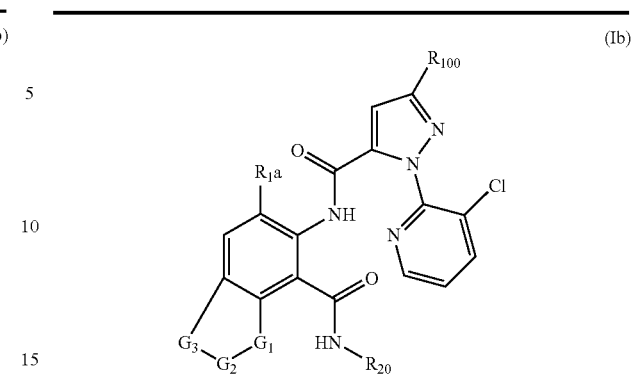

Compounds of formula Ib:

| Line | $R_1a$ | $R_{100}$ | $R_{20}$ |
|---|---|---|---|
| A.1.505 | C≡CH | Cl | |
| A.1.506 | C≡CH | Cl | $CH(CH_3)_2CH_2SCH_3$ |
| A.1.507 | C≡CH | Cl | $CH(CH_3)_2CH_2S(O)CH_3$ |
| A.1.508 | C≡CH | Cl | $CH(CH_3)_2CH_2S(O)_2CH_3$ |
| A.1.509 | C≡CH | Cl | $CH(CH_3)_2CH_2S(O)(NH)CH_3$ |
| A.1.510 | C≡CH | Cl | |
| A.1.511 | C≡CH | Cl | |
| A.1.512 | C≡CH | $CF_2H$ | H |
| A.1.513 | C≡CH | $CF_2H$ | $CH_3$ |
| A.1.514 | C≡CH | $CF_2H$ | $CH_2CH_3$ |
| A.1.515 | C≡CH | $CF_2H$ | $CH(CH_3)CH_3$ |
| A.1.516 | C≡CH | $CF_2H$ | $C(CH_3)(CH_3)CH_3$ |
| A.1.517 | C≡CH | $CF_2H$ | |
| A.1.518 | C≡CH | $CF_2H$ | |
| A.1.519 | C≡CH | $CF_2H$ | |
| A.1.520 | C≡CH | $CF_2H$ | |
| A.1.521 | C≡CH | $CF_2H$ | $CH(CH_3)_2CH_2SCH_3$ |
| A.1.522 | C≡CH | $CF_2H$ | $CH(CH_3)_2CH_2S(O)CH_3$ |
| A.1.523 | C≡CH | $CF_2H$ | $CH(CH_3)_2CH_2S(O)_2CH_3$ |
| A.1.524 | C≡CH | $CF_2H$ | $CH(CH_3)_2CH_2S(O)(NH)CH_3$ |

TABLE A-continued

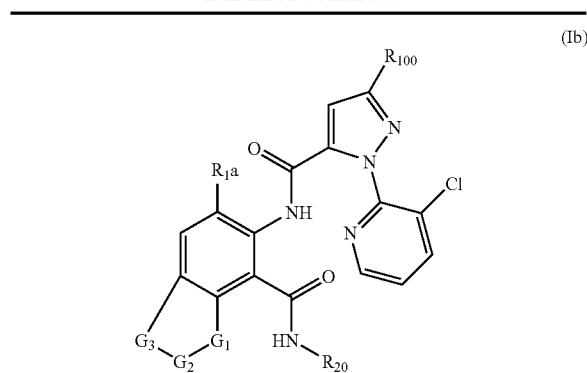

Compounds of formula Ib:

| Line | $R_1a$ | $R_{100}$ | $R_{20}$ |
|---|---|---|---|
| A.1.525 | C≡CH | $CF_2H$ | (cyclopropyl-CH(CH3)-CN) |
| A.1.526 | C≡CH | $CF_2H$ | (cyclopropyl-C(CH3)(CN)-) |
| A.1.527 | C≡CH | $OCF_3$ | H |
| A.1.528 | C≡CH | $OCF_3$ | $CH_3$ |
| A.1.529 | C≡CH | $OCF_3$ | $CH_2CH_3$ |
| A.1.530 | C≡CH | $OCF_3$ | $CH(CH_3)CH_3$ |
| A.1.531 | C≡CH | $OCF_3$ | $C(CH_3)(CH_3)CH_3$ |
| A.1.532 | C≡CH | $OCF_3$ | (cyclopropyl-CH2-) |
| A.1.533 | C≡CH | $OCF_3$ | (bicyclopropyl-CH-) |
| A.1.534 | C≡CH | $OCF_3$ | (methyl-bicyclopropyl) |
| A.1.535 | C≡CH | $OCF_3$ | (methyl-spiro cyclopropyl-cyclobutyl) |
| A.1.536 | C≡CH | $OCF_3$ | $CH(CH_3)_2CH_2SCH_3$ |
| A.1.537 | C≡CH | $OCF_3$ | $CH(CH_3)_2CH_2S(O)CH_3$ |
| A.1.538 | C≡CH | $OCF_3$ | $CH(CH_3)_2CH_2S(O)_2CH_3$ |
| A.1.539 | C≡CH | $OCF_3$ | $CH(CH_3)_2CH_2S(O)(NH)CH_3$ |
| A.1.540 | C≡CH | $OCF_3$ | (cyclopropyl-CH(CH3)-CN) |
| A.1.541 | C≡CH | $OCF_3$ | (cyclopropyl-C(CH3)(CN)-) |

TABLE A-continued

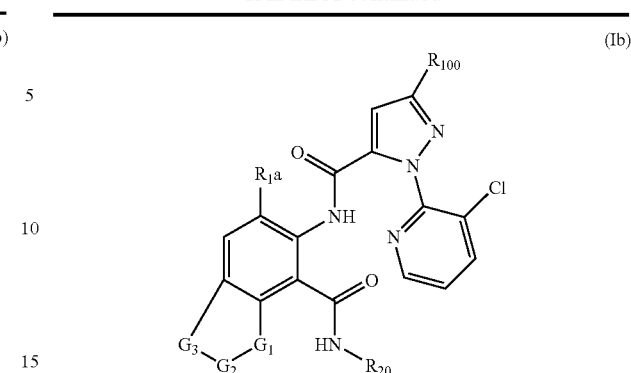

Compounds of formula Ib:

| Line | $R_1a$ | $R_{100}$ | $R_{20}$ |
|---|---|---|---|
| A.1.542 | C≡CH | $CF_3$ | H |
| A.1.543 | C≡CH | $CF_3$ | $CH_3$ |
| A.1.544 | C≡CH | $CF_3$ | $CH_2CH_3$ |
| A.1.545 | C≡CH | $CF_3$ | $CH(CH_3)CH_3$ |
| A.1.546 | C≡CH | $CF_3$ | $C(CH_3)(CH_3)CH_3$ |
| A.1.547 | C≡CH | $CF_3$ | (cyclopropyl-CH2-) |
| A.1.548 | C≡CH | $CF_3$ | (bicyclopropyl-CH-) |
| A.1.549 | C≡CH | $CF_3$ | (methyl-bicyclopropyl) |
| A.1.550 | C≡CH | $CF_3$ | (methyl-spiro cyclopropyl-cyclobutyl) |
| A.1.551 | C≡CH | $CF_3$ | $CH(CH_3)_2CH_2SCH_3$ |
| A.1.552 | C≡CH | $CF_3$ | $CH(CH_3)_2CH_2S(O)CH_3$ |
| A.1.553 | C≡CH | $CF_3$ | $CH(CH_3)_2CH_2S(O)_2CH_3$ |
| A.1.554 | C≡CH | $CF_3$ | $CH(CH_3)_2CH_2S(O)(NH)CH_3$ |
| A.1.555 | C≡CH | $CF_3$ | (cyclopropyl-CH(CH3)-CN) |
| A.1.556 | C≡CH | $CF_3$ | (cyclopropyl-C(CH3)(CN)-) |
| A.1.557 | H | $OCH_2CF_3$ | H |
| A.1.558 | H | $OCH_2CF_3$ | $CH_3$ |
| A.1.559 | H | $OCH_2CF_3$ | $CH_2CH_3$ |
| A.1.560 | H | $OCH_2CF_3$ | $CH(CH_3)CH_3$ |
| A.1.561 | H | $OCH_2CF_3$ | $C(CH_3)(CH_3)CH_3$ |
| A.1.562 | H | $OCH_2CF_3$ | (cyclopropyl-CH2-) |

TABLE A-continued

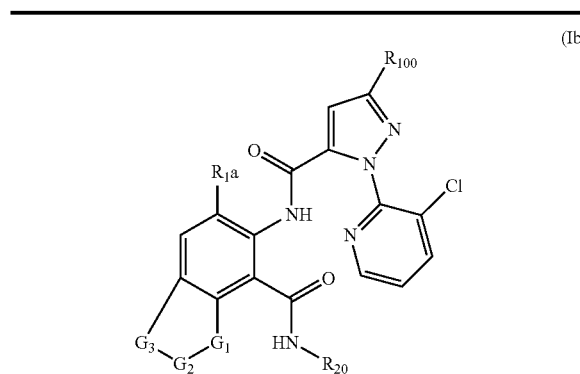

(Ib)

Compounds of formula Ib:

| Line | R₁a | R₁₀₀ | R₂₀ |
|---|---|---|---|
| A.1.563 | H | OCH₂CF₃ | (bicyclopropyl-methyl) |
| A.1.564 | H | OCH₂CF₃ | (cyclopropyl-cyclopropyl) |
| A.1.565 | H | OCH₂CF₃ | (spiro cyclopropyl-cyclobutyl) |
| A.1.566 | H | OCH₂CF₃ | CH(CH₃)₂CH₂SCH₃ |
| A.1.567 | H | OCH₂CF₃ | CH(CH₃)₂CH₂S(O)CH₃ |
| A.1.568 | H | OCH₂CF₃ | CH(CH₃)₂CH₂S(O)₂CH₃ |
| A.1.569 | H | OCH₂CF₃ | CH(CH₃)₂CH₂S(O)(NH)CH₃ |
| A.1.570 | H | OCH₂CF₃ | (cyclopropyl-CH(CN)) |
| A.1.571 | H | OCH₂CF₃ | (cyclopropyl-C(CH₃)(CN)) |
| A.1.572 | H | Br | H |
| A.1.573 | H | Br | CH₃ |
| A.1.574 | H | Br | CH₂CH₃ |
| A.1.575 | H | Br | CH(CH₃)CH₃ |
| A.1.576 | H | Br | C(CH₃)(CH₃)CH₃ |
| A.1.577 | H | Br | (cyclopropylmethyl) |
| A.1.578 | H | Br | (bicyclopropyl-methyl) |
| A.1.579 | H | Br | (cyclopropyl-cyclopropyl) |

TABLE A-continued

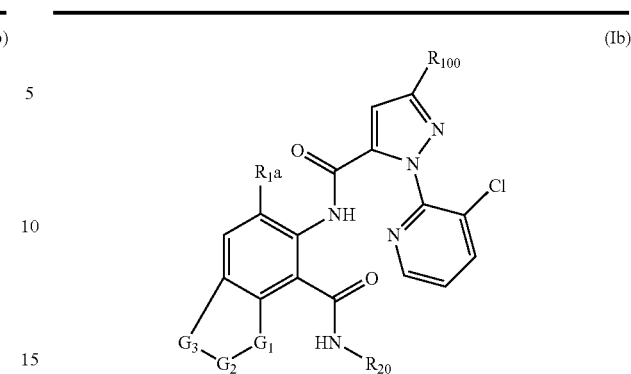

(Ib)

Compounds of formula Ib:

| Line | R₁a | R₁₀₀ | R₂₀ |
|---|---|---|---|
| A.1.580 | H | Br | (spiro cyclopropyl-cyclobutyl) |
| A.1.581 | H | Br | CH(CH₃)₂CH₂SCH₃ |
| A.1.582 | H | Br | CH(CH₃)₂CH₂S(O)CH₃ |
| A.1.583 | H | Br | CH(CH₃)₂CH₂S(O)₂CH₃ |
| A.1.584 | H | Br | CH(CH₃)₂CH₂S(O)(NH)CH₃ |
| A.1.585 | H | Br | (cyclopropyl-CH(CN)) |
| A.1.586 | H | Br | (cyclopropyl-C(CH₃)(CN)) |
| A.1.587 | H | Cl | H |
| A.1.588 | H | Cl | CH₃ |
| A.1.589 | H | Cl | CH₂CH₃ |
| A.1.590 | H | Cl | CH(CH₃)CH₃ |
| A.1.591 | H | Cl | C(CH₃)(CH₃)CH₃ |
| A.1.592 | H | Cl | (cyclopropylmethyl) |
| A.1.593 | H | Cl | (bicyclopropyl-methyl) |
| A.1.594 | H | Cl | (cyclopropyl-cyclopropyl) |
| A.1.595 | H | Cl | (spiro cyclopropyl-cyclobutyl) |
| A.1.596 | H | Cl | CH(CH₃)₂CH₂SCH₃ |
| A.1.597 | H | Cl | CH(CH₃)₂CH₂S(O)CH₃ |
| A.1.598 | H | Cl | CH(CH₃)₂CH₂S(O)₂CH₃ |
| A.1.599 | H | Cl | CH(CH₃)₂CH₂S(O)(NH)CH₃ |

TABLE A-continued

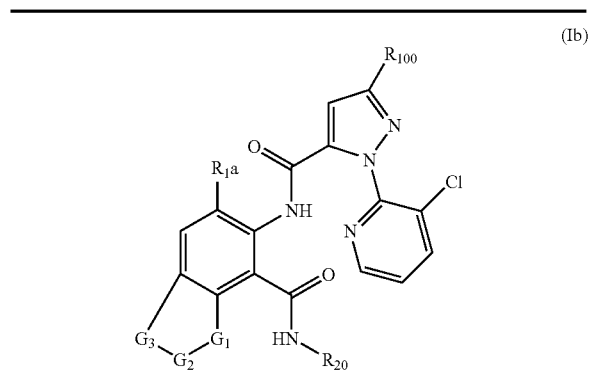

Compounds of formula Ib:

| Line | R₁a | R₁₀₀ | R₂₀ |
|---|---|---|---|
| A.1.600 | H | Cl | (1-cyanoethyl-cyclopropyl) |
| A.1.601 | H | Cl | (2-cyano-2-methyl-cyclopropyl-ethyl) |
| A.1.602 | H | CF₂H | H |
| A.1.603 | H | CF₂H | CH₃ |
| A.1.604 | H | CF₂H | CH₂CH₃ |
| A.1.605 | H | CF₂H | CH(CH₃)CH₃ |
| A.1.606 | H | CF₂H | C(CH₃)(CH₃)CH₃ |
| A.1.607 | H | CF₂H | (ethylcyclopropyl) |
| A.1.608 | H | CF₂H | (methylbicyclopropyl) |
| A.1.609 | H | CF₂H | (methylbicyclopropyl) |
| A.1.610 | H | CF₂H | (methylspiro[2.3]hexane) |
| A.1.611 | H | CF₂H | CH(CH₃)₂CH₂SCH₃ |
| A.1.612 | H | CF₂H | CH(CH₃)₂CH₂S(O)CH₃ |
| A.1.613 | H | CF₂H | CH(CH₃)₂CH₂S(O)₂CH₃ |
| A.1.614 | H | CF₂H | CH(CH₃)₂CH₂S(O)(NH)CH₃ |
| A.1.615 | H | CF₂H | (1-cyanoethyl-cyclopropyl) |
| A.1.616 | H | CF₂H | (2-cyano-2-methyl-cyclopropyl) |

TABLE A-continued

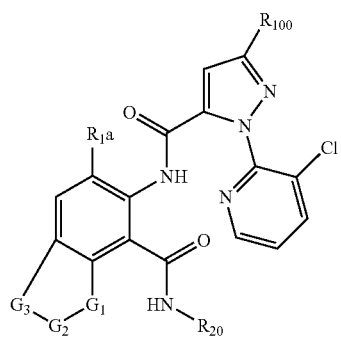

Compounds of formula Ib:

| Line | R₁a | R₁₀₀ | R₂₀ |
|---|---|---|---|
| A.1.617 | H | OCF₃ | H |
| A.1.618 | H | OCF₃ | CH₃ |
| A.1.619 | H | OCF₃ | CH₂CH₃ |
| A.1.620 | H | OCF₃ | CH(CH₃)CH₃ |
| A.1.621 | H | OCF₃ | C(CH₃)(CH₃)CH₃ |
| A.1.622 | H | OCF₃ | (ethylcyclopropyl) |
| A.1.623 | H | OCF₃ | (methylbicyclopropyl) |
| A.1.624 | H | OCF₃ | (methylbicyclopropyl) |
| A.1.625 | H | OCF₃ | (methylspiro[2.3]hexane) |
| A.1.626 | H | OCF₃ | CH(CH₃)₂CH₂SCH₃ |
| A.1.627 | H | OCF₃ | CH(CH₃)₂CH₂S(O)CH₃ |
| A.1.628 | H | OCF₃ | CH(CH₃)₂CH₂S(O)₂CH₃ |
| A.1.629 | H | OCF₃ | CH(CH₃)₂CH₂S(O)(NH)CH₃ |
| A.1.630 | H | OCF₃ | (1-cyanoethyl-cyclopropyl) |
| A.1.631 | H | OCF₃ | (2-cyano-2-methyl-cyclopropyl) |
| A.1.632 | Cl | OCH₃ | H |
| A.1.633 | Cl | OCH₃ | CH₃ |
| A.1.634 | Cl | OCH₃ | CH₂CH₃ |
| A.1.635 | Cl | OCH₃ | CH(CH₃)CH₃ |
| A.1.636 | Cl | OCH₃ | C(CH₃)(CH₃)CH₃ |
| A.1.637 | Cl | OCH₃ | (ethylcyclopropyl) |

TABLE A-continued

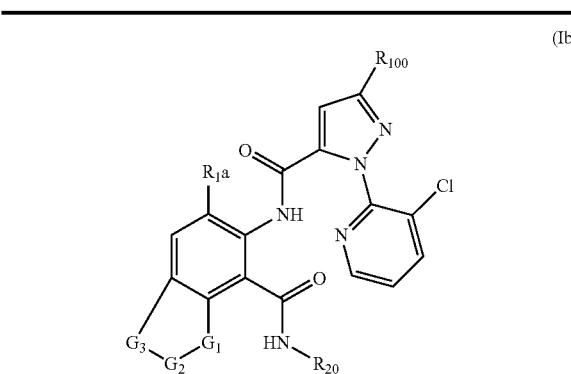

Compounds of formula Ib:

| Line | R₁a | R₁₀₀ | R₂₀ |
|---|---|---|---|
| A.1.638 | Cl | OCH₃ | (methylbicyclopropyl) |
| A.1.639 | Cl | OCH₃ | (bicyclopropyl) |
| A.1.640 | Cl | OCH₃ | (methylspiro[2.3]hexyl) |
| A.1.641 | Cl | OCH₃ | CH(CH₃)₂CH₂SCH₃ |
| A.1.642 | Cl | OCH₃ | CH(CH₃)₂CH₂S(O)CH₃ |
| A.1.643 | Cl | OCH₃ | CH(CH₃)₂CH₂S(O)₂CH₃ |
| A.1.644 | Cl | OCH₃ | CH(CH₃)₂CH₂S(O)(NH)CH₃ |
| A.1.645 | Cl | OCH₃ | (1-cyclopropylethyl with CN) |
| A.1.646 | Cl | OCH₃ | (1-cyclopropyl-1-methyl with CN) |
| A.1.647 | Br | OCH₃ | H |
| A.1.648 | Br | OCH₃ | CH₃ |
| A.1.649 | Br | OCH₃ | CH₂CH₃ |
| A.1.650 | Br | OCH₃ | CH(CH₃)CH₃ |
| A.1.651 | Br | OCH₃ | C(CH₃)(CH₃)CH₃ |
| A.1.652 | Br | OCH₃ | (cyclopropylmethyl deriv.) |
| A.1.653 | Br | OCH₃ | (bicyclopropyl deriv.) |
| A.1.654 | Br | OCH₃ | (bicyclopropyl deriv.) |

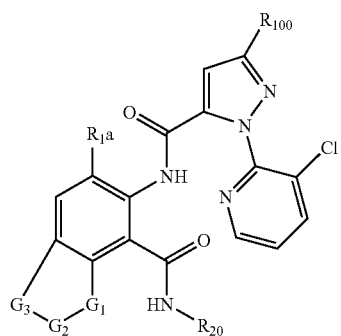

Compounds of formula Ib:

| Line | R₁a | R₁₀₀ | R₂₀ |
|---|---|---|---|
| A.1.655 | Br | OCH₃ | (methylspiro[2.3]hexyl) |
| A.1.656 | Br | OCH₃ | CH(CH₃)₂CH₂SCH₃ |
| A.1.657 | Br | OCH₃ | CH(CH₃)₂CH₂S(O)CH₃ |
| A.1.658 | Br | OCH₃ | CH(CH₃)₂CH₂S(O)₂CH₃ |
| A.1.659 | Br | OCH₃ | CH(CH₃)₂CH₂S(O)(NH)CH₃ |
| A.1.660 | Br | OCH₃ | (1-cyclopropylethyl with CN) |
| A.1.661 | Br | OCH₃ | (1-cyclopropyl-1-methyl with CN) |
| A.1.662 | CH₃ | OCH₃ | H |
| A.1.663 | CH₃ | OCH₃ | CH₃ |
| A.1.664 | CH₃ | OCH₃ | CH₂CH₃ |
| A.1.665 | CH₃ | OCH₃ | CH(CH₃)CH₃ |
| A.1.666 | CH₃ | OCH₃ | C(CH₃)(CH₃)CH₃ |
| A.1.667 | CH₃ | OCH₃ | (cyclopropylmethyl deriv.) |
| A.1.668 | CH₃ | OCH₃ | (bicyclopropyl deriv.) |
| A.1.669 | CH₃ | OCH₃ | (bicyclopropyl deriv.) |
| A.1.670 | CH₃ | OCH₃ | (methylspiro[2.3]hexyl) |
| A.1.671 | CH₃ | OCH₃ | CH(CH₃)₂CH₂SCH₃ |
| A.1.672 | CH₃ | OCH₃ | CH(CH₃)₂CH₂S(O)CH₃ |
| A.1.673 | CH₃ | OCH₃ | CH(CH₃)₂CH₂S(O)₂CH₃ |
| A.1.674 | CH₃ | OCH₃ | CH(CH₃)₂CH₂S(O)(NH)CH₃ |

TABLE A-continued

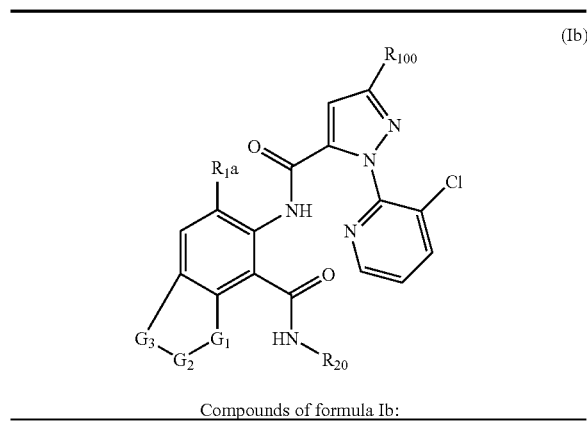

Compounds of formula Ib:

| Line | $R_1a$ | $R_{100}$ | $R_{20}$ |
|---|---|---|---|
| A.1.675 | $CH_3$ | $OCH_3$ | *cyclopropyl-CH(CH_3)-CN* |
| A.1.676 | $CH_3$ | $OCH_3$ | *cyclopropyl-C(CH_3)(CN)-* |
| A.1.677 | H | $OCH_3$ | H |
| A.1.678 | H | $OCH_3$ | $CH_3$ |
| A.1.679 | H | $OCH_3$ | $CH_2CH_3$ |
| A.1.680 | H | $OCH_3$ | $CH(CH_3)CH_3$ |
| A.1.681 | H | $OCH_3$ | $C(CH_3)(CH_3)CH_3$ |
| A.1.682 | H | $OCH_3$ | *cyclopropyl-CH(CH_3)-* |
| A.1.683 | H | $OCH_3$ | *bicyclopropyl* |
| A.1.684 | H | $OCH_3$ | *methyl-bicyclopropyl* |
| A.1.685 | H | $OCH_3$ | *methyl-spiro[2.3]* |
| A.1.686 | H | $OCH_3$ | $CH(CH_3)_2CH_2SCH_3$ |
| A.1.687 | H | $OCH_3$ | $CH(CH_3)_2CH_2S(O)CH_3$ |
| A.1.688 | H | $OCH_3$ | $CH(CH_3)_2CH_2S(O)_2CH_3$ |
| A.1.689 | H | $OCH_3$ | $CH(CH_3)_2CH_2S(O)(NH)CH_3$ |
| A.1.690 | H | $OCH_3$ | *cyclopropyl-CH(CH_3)-CN* |
| A.1.691 | H | $OCH_3$ | *cyclopropyl-C(CH_3)(CN)-* |

TABLE A-continued

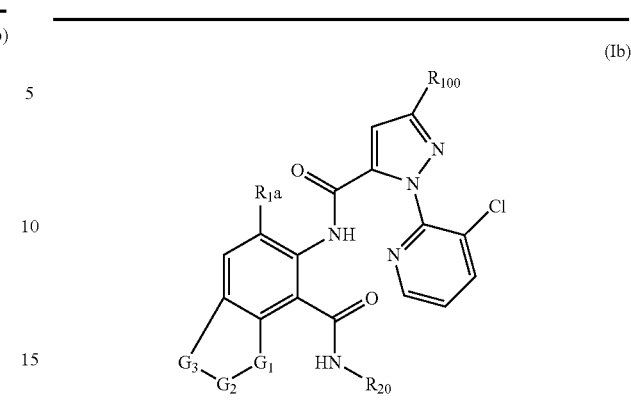

Compounds of formula Ib:

| Line | $R_1a$ | $R_{100}$ | $R_{20}$ |
|---|---|---|---|
| A.1.692 | C≡CH | $OCH_3$ | H |
| A.1.693 | C≡CH | $OCH_3$ | $CH_3$ |
| A.1.694 | C≡CH | $OCH_3$ | $CH_2CH_3$ |
| A.1.695 | C≡CH | $OCH_3$ | $CH(CH_3)CH_3$ |
| A.1.696 | C≡CH | $OCH_3$ | $C(CH_3)(CH_3)CH_3$ |
| A.1.697 | C≡CH | $OCH_3$ | *cyclopropyl* |
| A.1.698 | C≡CH | $OCH_3$ | *methyl-bicyclopropyl* |
| A.1.699 | C≡CH | $OCH_3$ | *bicyclopropyl* |
| A.1.700 | C≡CH | $OCH_3$ | *methyl-spiro[2.3]* |
| A.1.701 | C≡CH | $OCH_3$ | $CH(CH_3)_2CH_2SCH_3$ |
| A.1.702 | C≡CH | $OCH_3$ | $CH(CH_3)_2CH_2S(O)CH_3$ |
| A.1.703 | C≡CH | $OCH_3$ | $CH(CH_3)_2CH_2S(O)_2CH_3$ |
| A.1.704 | C≡CH | $OCH_3$ | $CH(CH_3)_2CH_2S(O)(NH)CH_3$ |
| A.1.705 | C≡CH | $OCH_3$ | *cyclopropyl-CH(CH_3)-CN* |
| A.1.706 | C≡CH | $OCH_3$ | *cyclopropyl-C(CH_3)(CN)-* |

Table 1: This table discloses the 706 compounds T1.1.1 to T1.1.706 of the formula

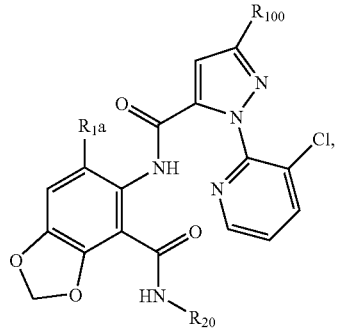

(T1)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A. For example, the specific compound T1.1.23 is the compound of the formula T1, in which each of the variables $R_{1a}$, $R_{20}$ and $R_{100}$ has the specific meaning given in the line A.1.23 of the Table A. According to the same system, also all of the other 706 specific compounds disclosed in the Table 1 as well as all of the specific compounds disclosed in the Tables 2 to 55 are specified analogously.

Table 2: This table discloses the 706 compounds T2.1.1 to T2.1.706 of the formula

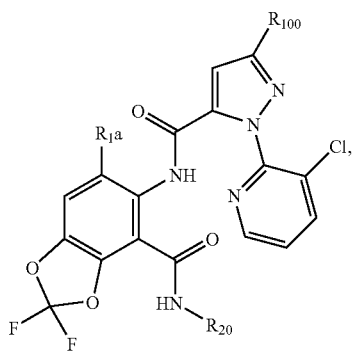

(T2)

in which, for each of these 706 specific compounds, each of the of the variables $R_{1a}$, $R_{20}$ and $R_{100}$ has the specific meaning given in the corresponding line, appropriately selected from the 564 lines A.1.1 to A.1.706 of the Table A.

Table 3: This table discloses the 706 compounds T3.1.1 to T3.1.706 of the formula

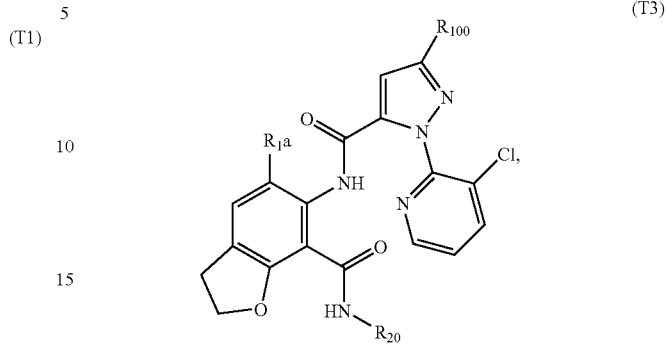

(T3)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 4: This table discloses the 706 compounds T4.1.1 to T4.1.706 of the formula

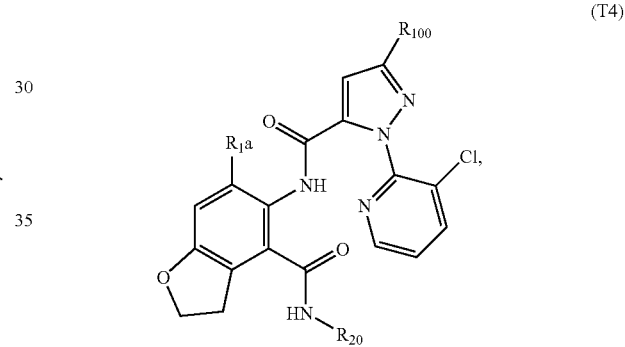

(T4)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 5: This table discloses the 706 compounds T5.1.1 to T5.1.706 of the formula

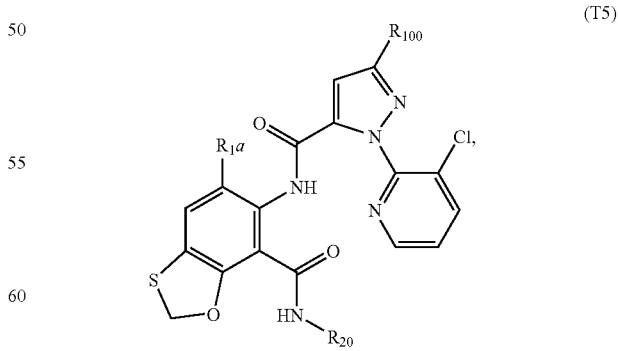

(T5)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 6: This table discloses the 706 compounds T6.1.1 to T6.1.706 of the formula

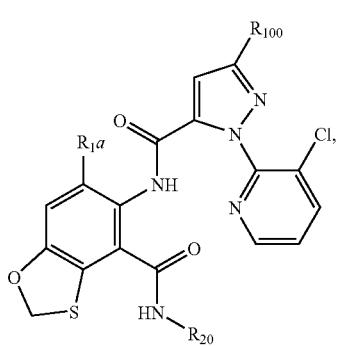
(T6)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 7: This table discloses the 706 compounds T7.1.1 to T7.1.706 of the formula

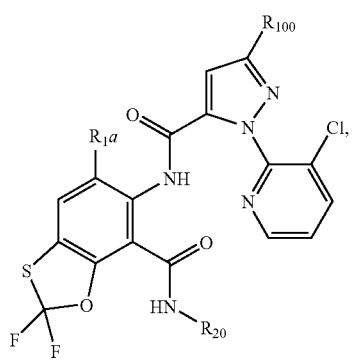
(T7)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 8: This table discloses the 706 compounds T8.1.1 to T8.1.706 of the formula

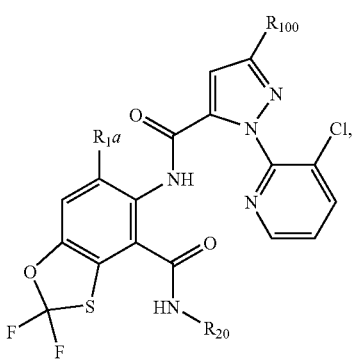
(T8)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 9: This table discloses the 706 compounds T9.1.1 to T9.1.706 of the formula

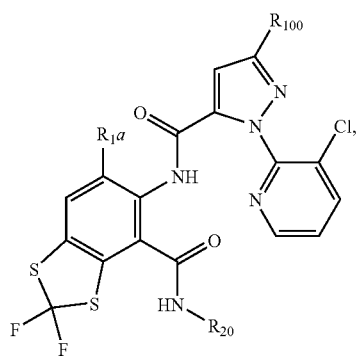
(T9)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 10: This table discloses the 706 compounds T10.1.1 to T10.1.706 of the formula

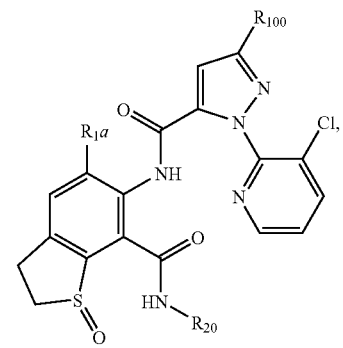
(T10)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 11: This table discloses the 706 compounds T11.1.1 to T11.1.706 of the formula (T11)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 12: This table discloses the 706 compounds T12.1.1 to T12.1.706 of the formula

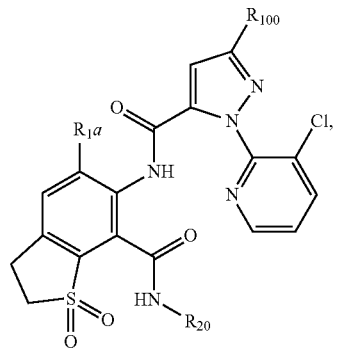
(T12)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 13: This table discloses the 706 compounds T13.1.1 to T13.1.706 of the formula

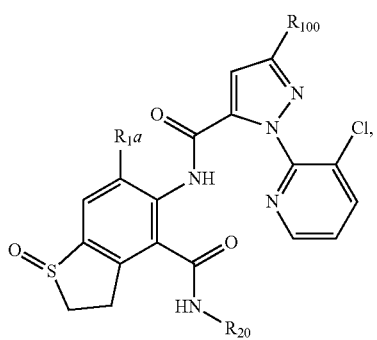
(T13)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 14: This table discloses the 706 compounds T14.1.1 to T14.1.706 of the formula

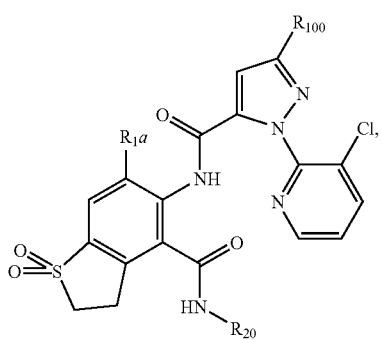
(T14)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 15: This table discloses the 706 compounds T15.1.1 to T15.1.706 of the formula

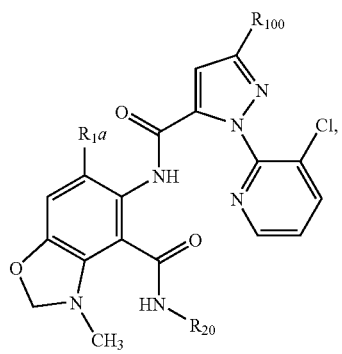
(T15)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 16: This table discloses the 706 compounds T16.1.1 to T16.1.706 of the formula

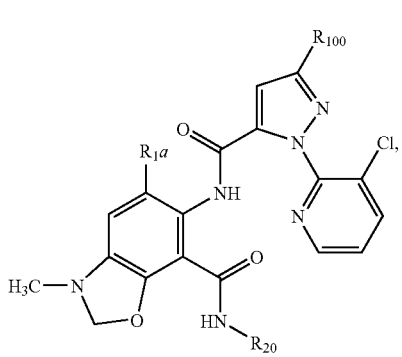
(T16)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 17: This table discloses the 706 compounds T17.1.1 to T17.1.706 of the formula

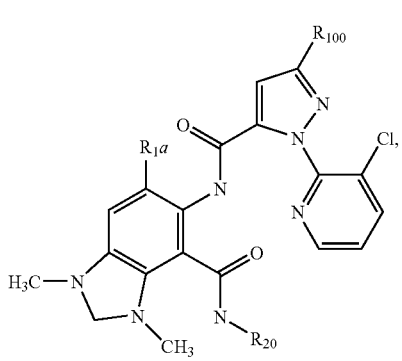
(T17)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 18: This table discloses the 706 compounds T18.1.1 to T18.1.706 of the formula

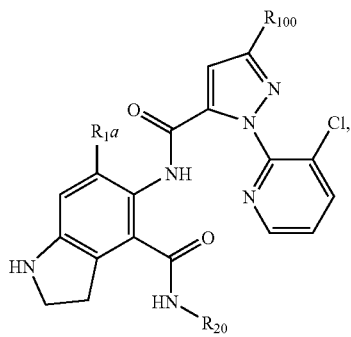
(T18)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1706 of the Table A.

Table 19: This table discloses the 706 compounds T19.1.1 to T19.1.706 of the formula

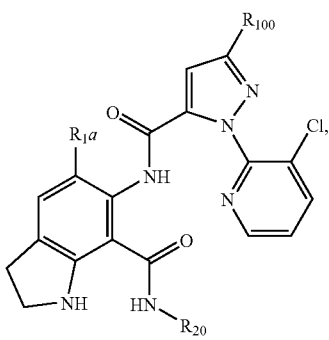
(T19)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 20: This table discloses the 706 compounds T20.1.1 to T20.1.706 of the formula

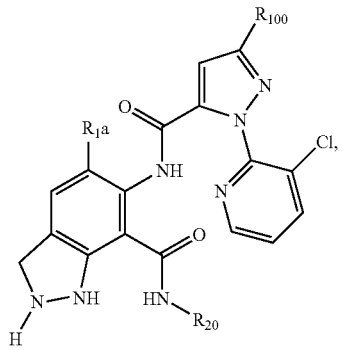
(T20)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 21: This table discloses the 706 compounds T21.1.1 to T21.1.706 of the formula

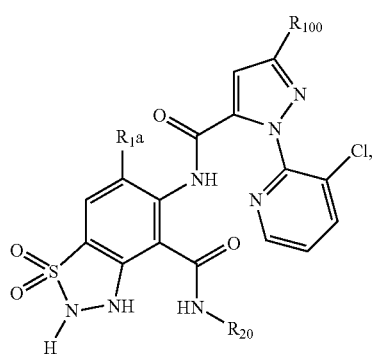
(T21)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 22: This table discloses the 706 compounds T22.1.1 to T22.1.706 of the formula

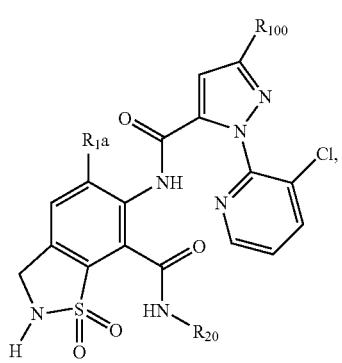
(T22)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 23: This table discloses the 706 compounds T23.1.1 to T23.1.706 of the formula

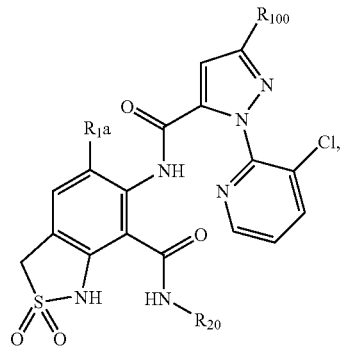

(T23)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 24: This table discloses the 706 compounds T24.1.1 to T24.1.706 of the formula

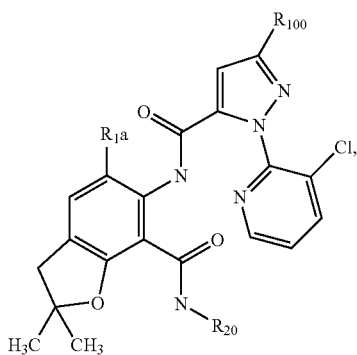

(T24)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 25: This table discloses the 706 compounds T25.1.1 to T25.1.706 of the formula

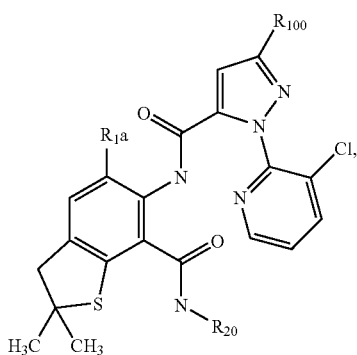

(T25)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 26: This table discloses the 706 compounds T26.1.1 to T26.1.706 of the formula

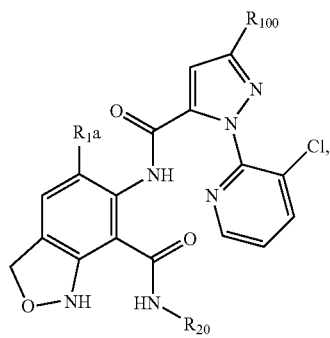

(T26)

in which, for each of these 706 specific compounds, each of the of the variables $R_{1a}$, $R_{20}$ and $R_{100}$ has the specific meaning given in the corresponding line, approximately selected from the 706 lines A.1.1 to A.1.706 of the Table A.

Table 27: This table discloses the 706 compounds T27.1.1 to T27.1.706 of the formula

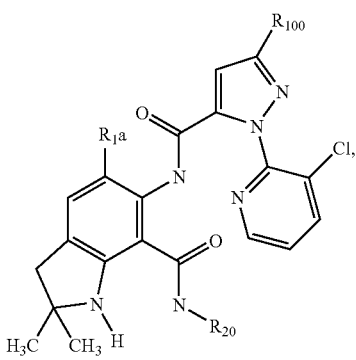

(T27)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 28: This table discloses the 706 compounds T28.1.1 to T28.1.706 of the formula

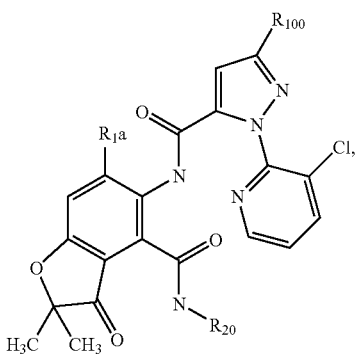

(T28)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 29: This table discloses the 706 compounds T29.1.1 to T29.1.706 of the formula

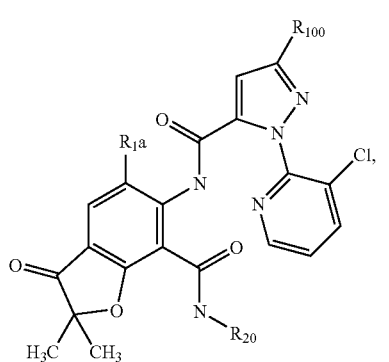

(T29)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 30: This table discloses the 706 compounds T30.1.1 to T30.1.706 of the formula

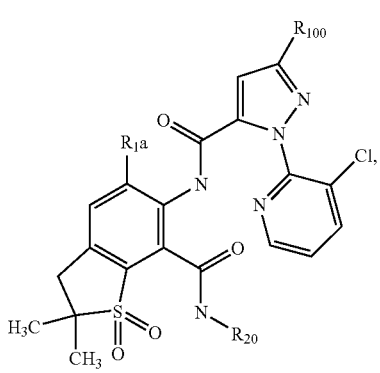

(T30)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 31: This table discloses the 706 compounds T31.1.1 to T31.1.706 of the formula

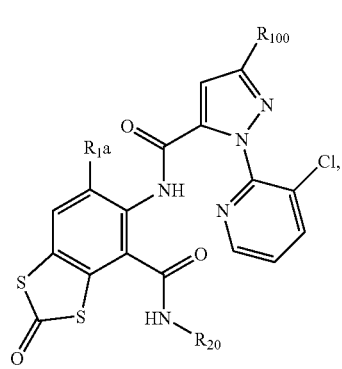

(T31)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 32: This table discloses the 706 compounds T32.1.1 to T32.1.706 of the formula

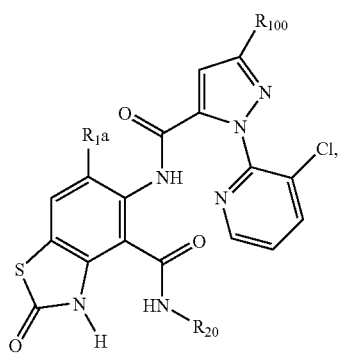

(T32)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 33: This table discloses the 706 compounds T33.1.1 to T33.1.706 of the formula

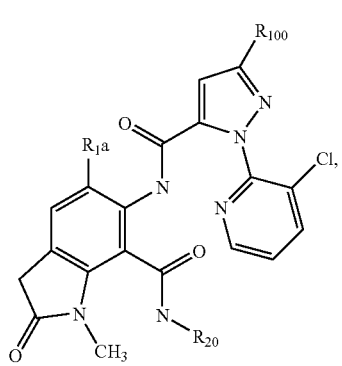

(T33)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 34: This table discloses the 706 compounds T34.1.1 to T34.1.706 of the formula

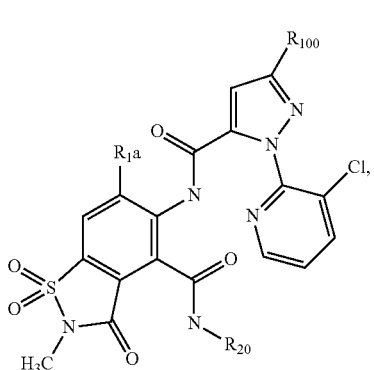

(T34)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 35: This table discloses the 706 compounds T35.1.1 to T35.1.706 of the formula

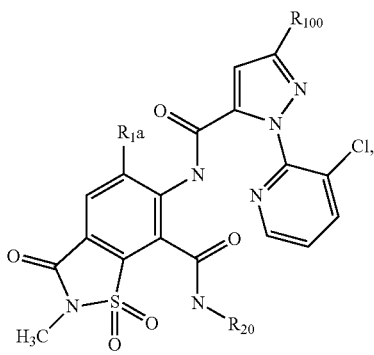
(T35)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 36: This table discloses the 706 compounds T36.1.1 to T36.1.706 of the formula

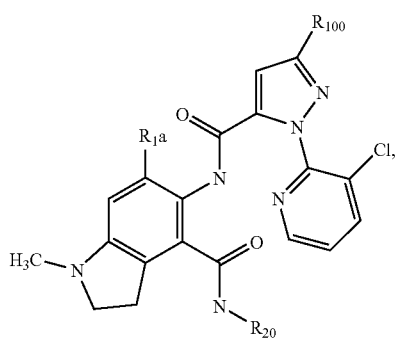
(T36)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 37: This table discloses the 706 compounds T37.1.1 to T37.1.706 of the formula

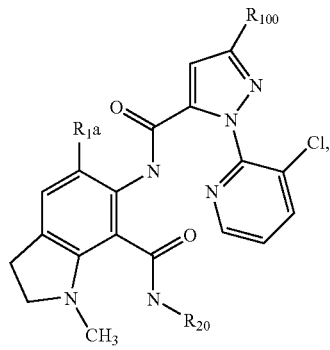
(T37)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 38: This table discloses the 706 compounds T38.1.1 to T38.1.706 of the formula (T38)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 39: This table discloses the 706 compounds T39.1.1 to T39.1.706 of the formula

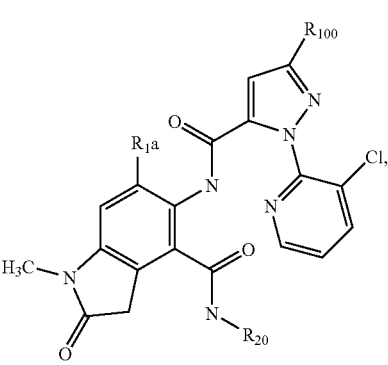
(T39)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 40: This table discloses the 706 compounds T40.1.1 to T40.1.706 of the formula

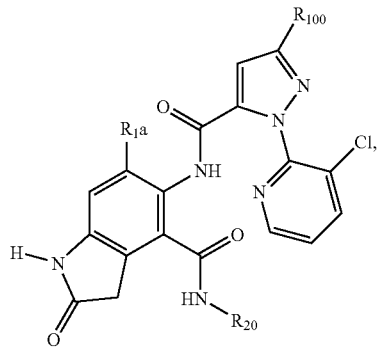

(T40)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 41: This table discloses the 706 compounds T41.1.1 to T41.1.706 of the formula

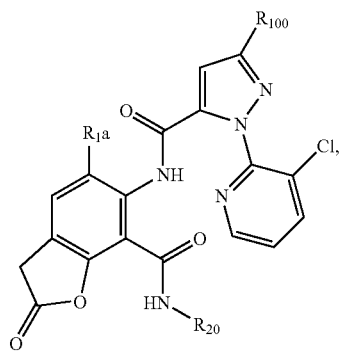

(T41)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 42: This table discloses the 706 compounds T42.1.1 to T42.1.706 of the formula

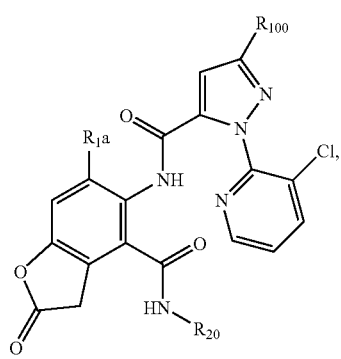

(T42)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 43: This table discloses the 706 compounds T43.1.1 to T43.1.706 of the formula

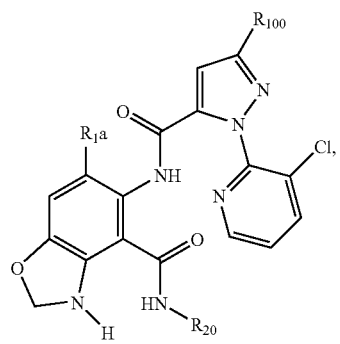

(T43)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 44: This table discloses the 706 compounds T44.1.1 to T44.1.706 of the formula

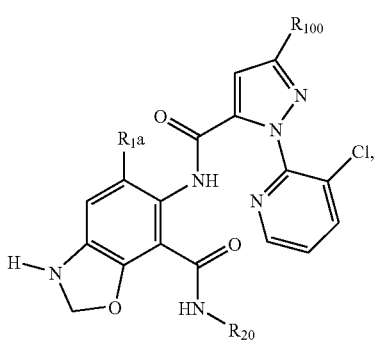

(T44)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 45: This table discloses the 706 compounds T45.1.1 to T45.1.706 of the formula

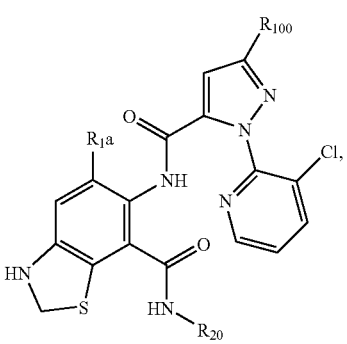

(T45)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 46: This table discloses the 706 compounds T46.1.1 to T46.1.706 of the formula

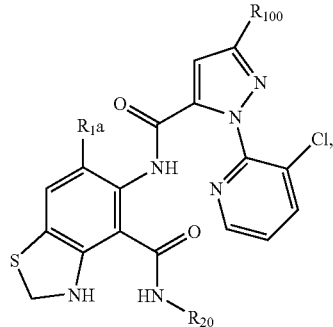

(T46)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 47: This table discloses the 706 compounds T47.1.1 to T47.1.706 of the formula

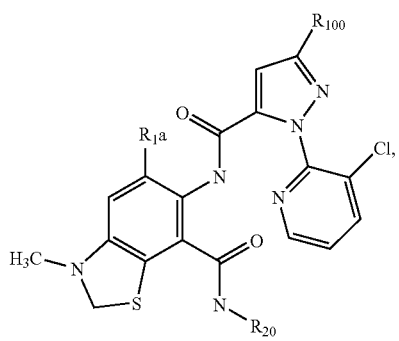

(T47)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 48: This table discloses the 706 compounds T48.1.1 to T48.1.706 of the formula

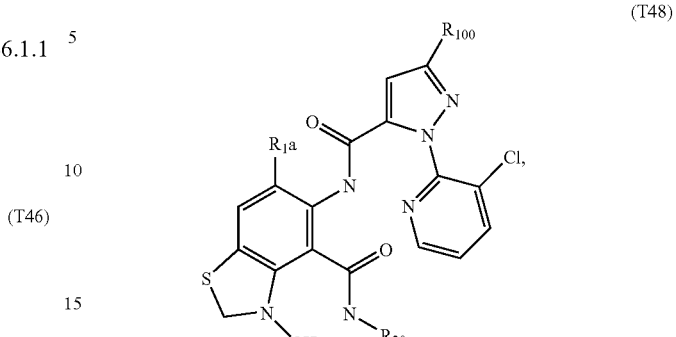

(T48)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 49: This table discloses the 706 compounds T49.1.1 to T49.1.706 of the formula

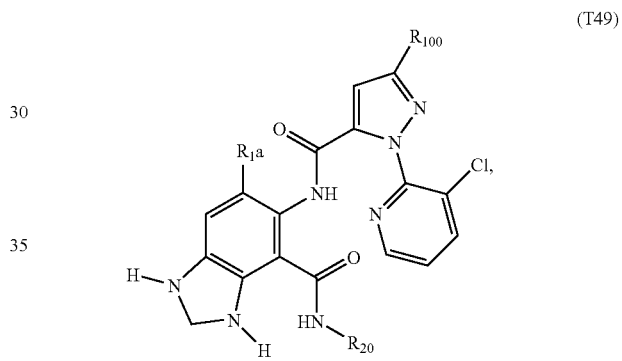

(T49)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 50: This table discloses the 706 compounds T50.1.1 to T50.1.706 of the formula

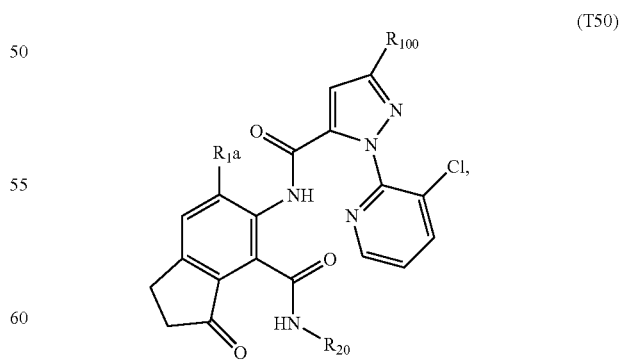

(T50)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 51: This table discloses the 706 compounds T51.1.1 to T51.1.706 of the formula

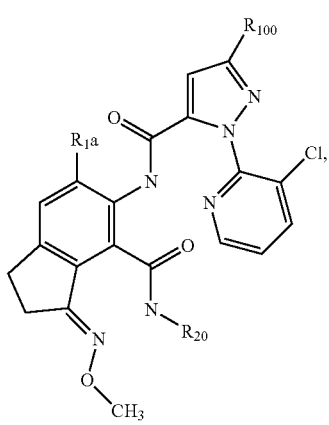

(T51)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 52: This table discloses the 706 compounds T52.1.1 to T52.1.706 of the formula

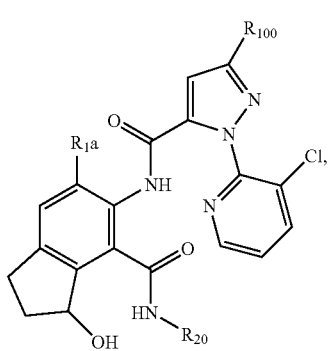

(T52)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 53: This table discloses the 706 compounds T53.1.1 to T53.1.706 of the formula

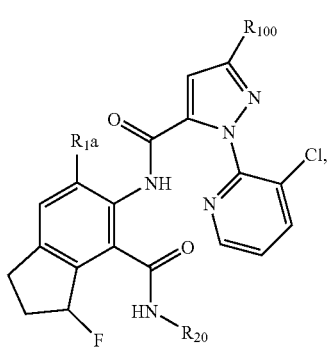

(T53)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 54: This table discloses the 706 compounds T54.1.1 to T54.1.706 of the formula

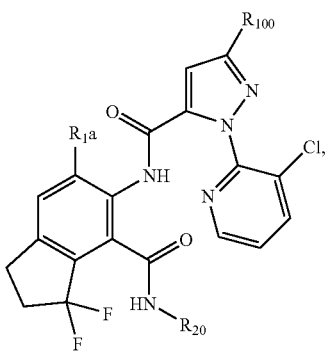

(T54)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 55: This table discloses the 706 compounds T55.1.1 to T55.1.706 of the formula

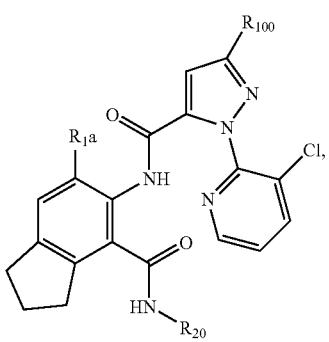

(T55)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 56: This table discloses the 706 compounds T56.1.1 to T56.1.706 of the formula

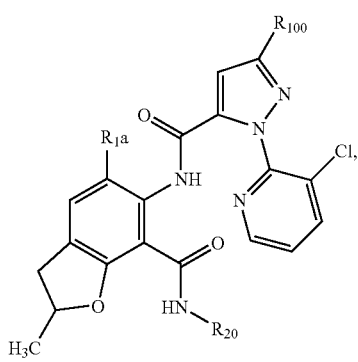

(T56)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

Table 57: This table discloses the 706 compounds T57.1.1 to T57.1.706 of the formula

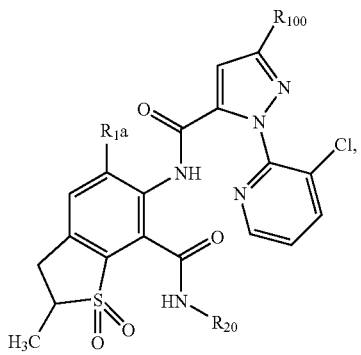
(T57)

in which, for each of these 706 specific compounds, each of the of the variables $R_{1a}$, $R_{20}$ and $R_{100}$ has the specific meaning given in the corresponding line, appropriately selected from the 706 lines A.1.1 to A.1.706 of the Table A.

FORMULATION EXAMPLES

%=Percent by Weight

Example F1

| Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2

| Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3

| Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4

| Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5

| Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6

| Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7

| Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8

| Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the is following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds of formulae T1 to T57 described in tables 1 to 57 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion to (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (626)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfuram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV to (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelen*- sis (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhiodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CON]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinyl-ethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl) aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoatemethyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-ylphosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus

[CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, an insecticide selected from the group consisting of the compound of formula A-1

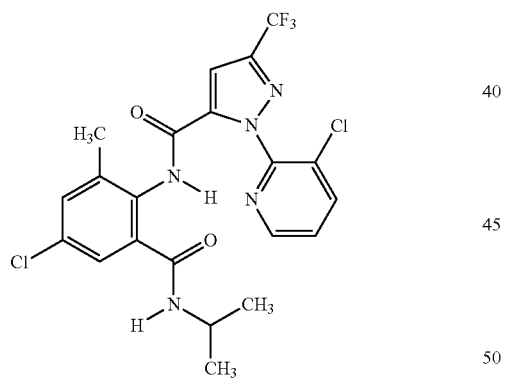

(A-1) + TX, the formula A-2

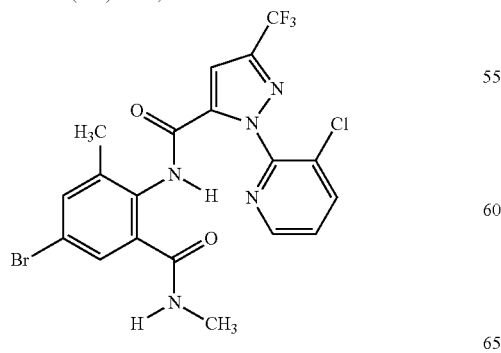

(A-2) + TX, the formula A-3

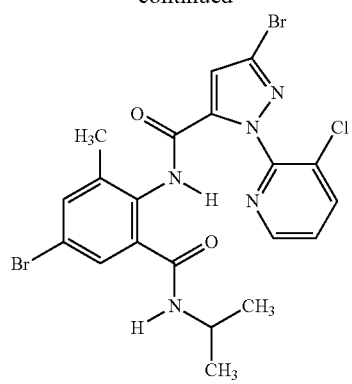

(A-3) + TX, the formula A-4

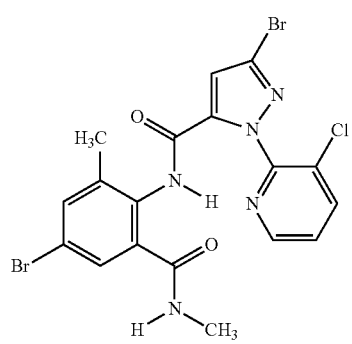

(A-4) + TX, the formula A-5

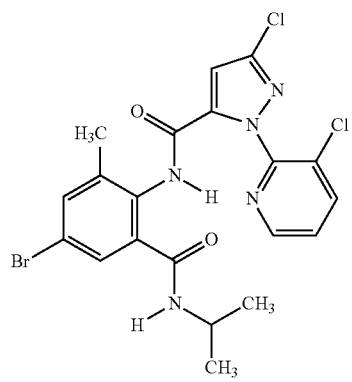

(A-5) + TX, the formula A-6

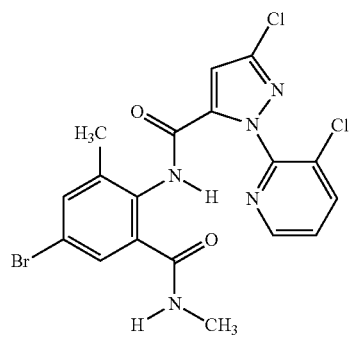

(A-6) + TX, the formula A-7

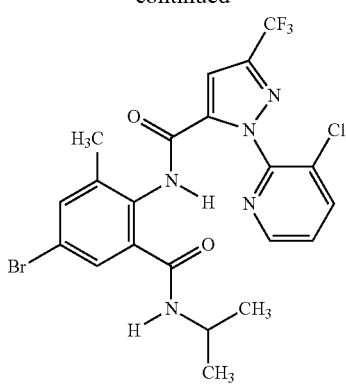
(A-7) + TX, the formula A-8
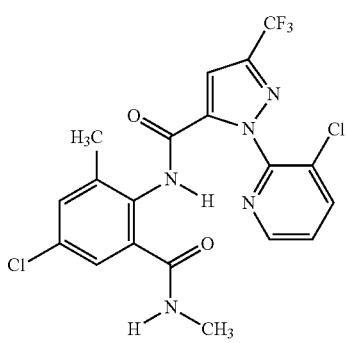
(A-8) + TX, the formula A-9
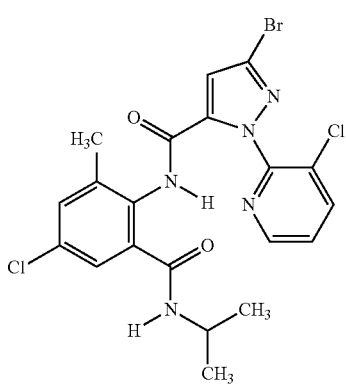
(A-9) + TX, the formula A-10
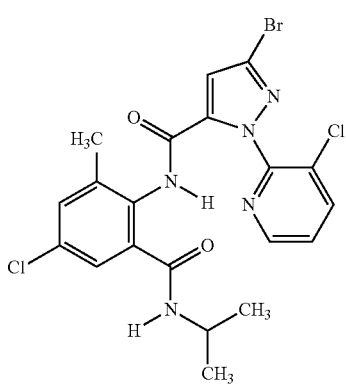
(A-10) + TX, the formula A-11
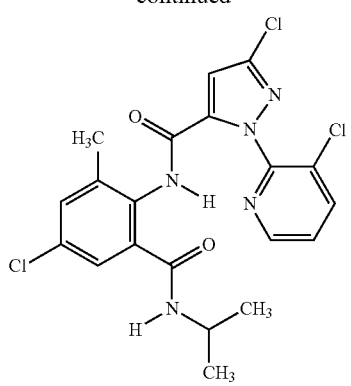
(A-11) + TX, the formula A-12
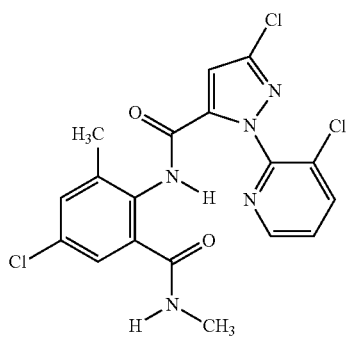
(A-12) + TX, the formula A13
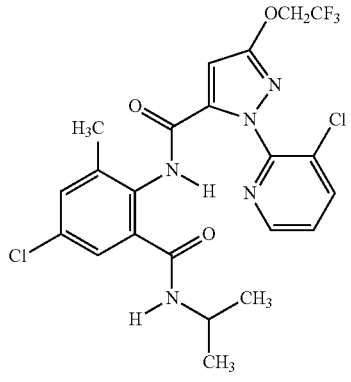
(A-13) + TX, the formula A-14
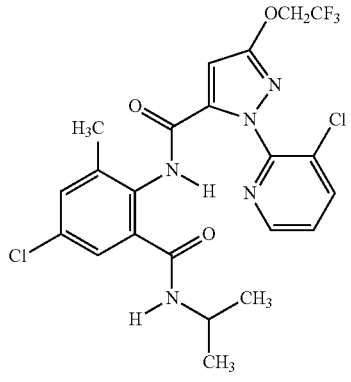
(A-14) + TX, the formula A-15

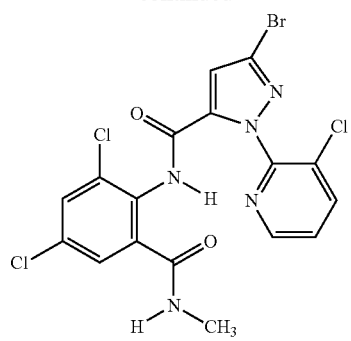
(A-15) + TX, the formula A-16
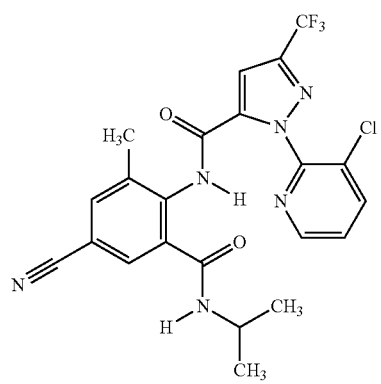
(A-16) + TX, the formula A-17
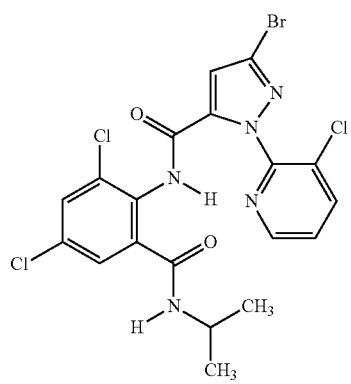
(A-17) + TX, the formula A-18
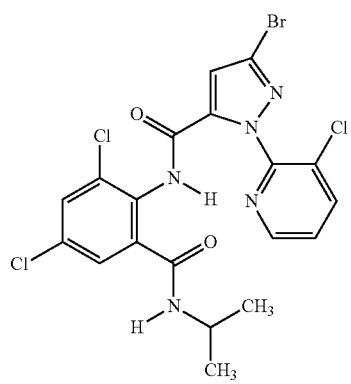
(A-18) + TX, the formula A-19
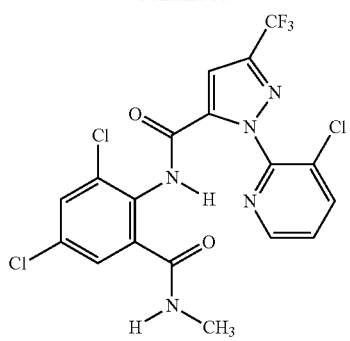
(A-19) + TX, the formula A-20
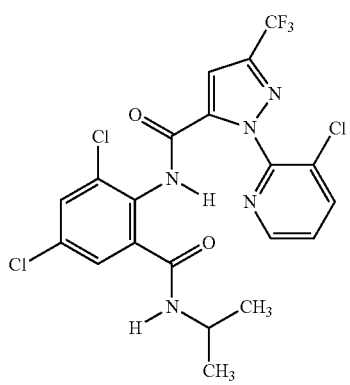
(A-20) + TX, the formula A-21
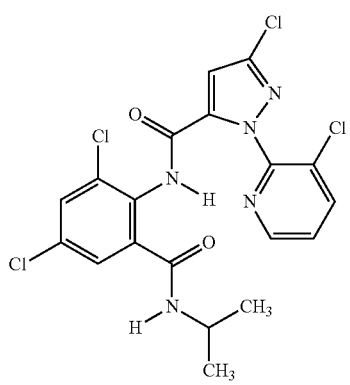
(A-21) + TX, the formula A-22
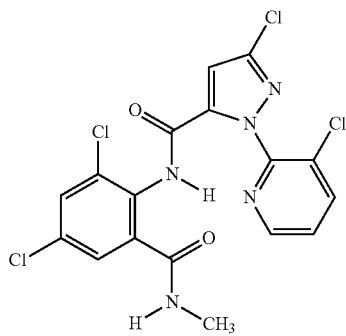
(A-22) + TX, the formula A-23

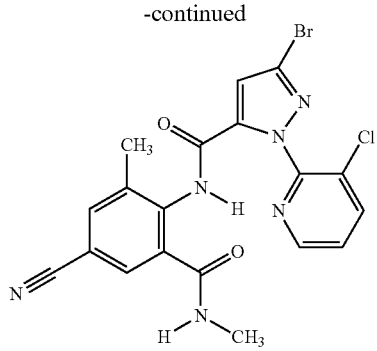

(A-23) + TX, the formula A-24

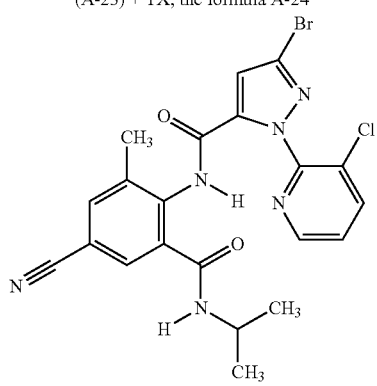

(A-24) + TX, the formula A-25

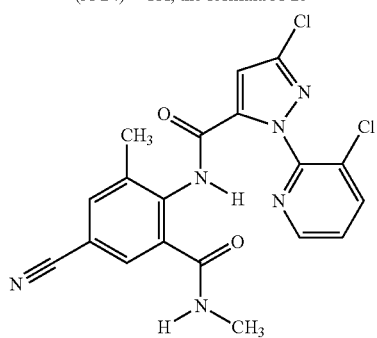

(A-25) + TX, and the formula A-26

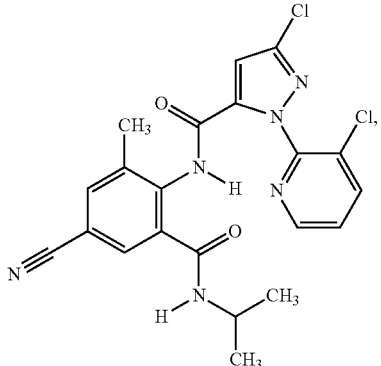

(A-26) + TX and biologically active compounds selected from the group consisting of Azaconazole (60207-31-0]+TX, Bitertanol [70585-36-3]+TX, Bromuconazole [116255-48-2]+TX, Cyproconazole [94361-06-5]+TX, Difenoconazole [119446-68-3]+TX, Diniconazole [83657-24-3]+TX, Epoxiconazole [106325-08-0]+TX, Fenbuconazole [114369-43-6]+TX, Fluquinconazole [136426-54-5]+TX, Flusilazole [85509-19-9]+TX, Flutriafol [76674-21-0]+TX, Hexaconazole [79983-71-4]+TX, Imazalil [35554-44-0]+TX, Imibenconazole [86598-92-7]+TX, Ipconazole [125225-28-7]+TX, Metconazole [125116-23-6]+TX, Myclobutanil [88671-89-0]+TX, Pefurazoate [101903-30-4]+TX, Penconazole [66246-88-6]+TX, Prothioconazole [178928-70-6]+TX, Pyrifenox [88283-41-4]+TX, Prochloraz [67747-09-5]+TX, Propiconazole [60207-90-1]+TX, Simeconazole [149508-90-7]+TX, Tebuconazole [107534-96-3]+TX, Tetraconazole [112281-77-3]+TX, Triadimefon [43121-43-3]+TX, Triadimenol [55219-65-3]+TX, Triflumizole [99387-89-0]+TX, Triticonazole [131983-72-7]+TX, Ancymidol [12771-68-5]+TX, Fenarimol [60168-88-9]+TX, Nuarimol [63284-71-9]+TX, Bupirimate [41483-43-6]+TX, Dimethirimol [5221-53-4]+TX, Ethirimol [23947-60-6]+TX, Dodemorph [1593-77-7]+TX, Fenpropidine [67306-00-7]+TX, Fenpropimorph [67564-91-4]+TX, Spiroxamine [118134-30-8]+TX, Tridemorph [81412-43-3]+TX, Cyprodinil [121552-61-2]+TX, Mepanipyrim [110235-47-7]+TX, Pyrimethanil [53112-28-0]+TX, Fenpiclonil [74738-17-3]+TX, Fludioxonil [131341-86-1]+TX, Benalaxyl [71626-11-4]+TX, Furalaxyl [57646-30-7]+TX, Metalaxyl [57837-19-1]+TX, R-Metalaxyl [70630-17-0]+TX, Ofurace [58810-48-3]+TX, Oxadixyl [77732-09-3]+TX, Benomyl [17804-35-2]+TX, Carbendazim [10605-21-7]+TX, Debacarb [62732-91-6]+TX, Fuberidazole [3878-19-1]+TX, Thiabendazole [148-79-8]+TX, Chlozolinate [84332-86-5]+TX, Dichlozoline [24201-58-9]+TX, Iprodione [36734-19-7]+TX, Myclozoline [54864-61-8]+TX, Procymidone [32809-16-8]+TX, Vinclozoline [50471-44-8]+TX, Boscalid [188425-85-6]+TX, Carboxin [5234-68-4]+TX, Fenfuram [24691-80-3]+TX, Flutolanil [66332-96-5]+TX, Mepronil [55814-41-0]+TX, Oxycarboxin [5259-88-1]+TX, Penthiopyrad [183675-82-3]+TX, Thifluzamide [130000-40-7]+TX, Guazatine [108173-90-6]+TX, Dodine [2439-10-3] [112-65-2] (freie Base)+TX, Iminoctadine [13516-27-3]+TX, Azoxystrobin [131860-33-8]+TX, Dimoxystrobin [149961-52-4]+TX, enestroburin {Proc. BCPC, Int. Congr., Glasgow, 2003, 1, 93}+TX, Fluoxastrobin [361377-29-9]+TX, Kresoxim-methyl [143390-89-0]+TX, Metominostrobin [133408-50-1]+TX, Trifloxystrobin [141517-21-7]+TX, Orysastrobin [248593-16-0]+TX, Picoxystrobin [117428-22-5]+TX, Pyraclostrobin [175013-18-0]+TX, Ferbam [14484-64-1]+TX, Mancozeb [8018-01-7]+TX, Maneb [12427-38-2]+TX, Metiram [9006-42-2]+TX, Propineb [12071-83-9]+TX, Thiram [137-26-8]+TX, Zineb [12122-67-7]+TX, Ziram [137-30-4]+TX, Captafol [2425-06-1]+TX, Captan [133-06-2]+TX, Dichlofluanid [1085-98-9]+TX, Fluoroimide [41205-21-4]+TX, Folpet [133-07-3]+TX, Tolylfluanid [731-27-1]+TX, Bordeaux Mixture [8011-63-0]+TX, Copperhydroxid [20427-59-2]+TX, Copperoxychlorid [1332-40-7]+TX, Coppersulfat [7758-98-7]+TX, Copperoxid [1317-39-1]+TX, Mancopper [53988-93-5]+TX, Oxine-copper [10380-28-6]+TX, Dinocap [131-72-6]+TX, Nitrothal-isopropyl [10552-74-6]+TX, Edifenphos [17109-49-8]+TX, Iprobenphos [26087-47-8]+TX, Isoprothiolane [50512-35-1]+TX, Phosdiphen [36519-00-3]+TX, Pyrazophos [13457-18-6]+TX, Tolclofos-methyl [57018-04-9]+TX, Acibenzolar-S-methyl [135158-54-2]+TX, Anilazine [101-05-3]+TX, Benthiavalicarb [413615-35-7]+TX, Blasticidin-S [2079-00-7]+TX, Chinomethionat [2439-01-2]+TX, Chloroneb [2675-77-6]+TX, Chlorothalonil [1897-45-6]+TX, Cyflufenamid [180409-60-3]+TX, Cymoxanil [57966-95-7]+TX, Dichlone [117-80-6]+TX, Diclocymet [139920-32-4]+TX, Diclomezine [62865-36-5]+TX, Dicloran [99-30-

9]+TX, Diethofencarb [87130-20-9]+TX, Dimethomorph [110488-70-5]+TX, SYP-L190 (Flumorph) [211867-47-9]TX, Dithianon [3347-22-6]+TX, Ethaboxam [162650-77-3]+TX, Etridiazole [2593-15-9]+TX, Famoxadone [131807-57-3]+TX, Fenamidone [161326-34-7]+TX, Fenoxanil [115852-48-7]+TX, Fentin [668-34-8]+TX, Ferimzone [89269-64-7]+TX, Fluazinam [79622-59-6]+TX, Fluopicolide [239110-15-7]+TX, Flusulfamide [106917-52-6]+TX, Fenhexamid [126833-17-8]+TX, Fosetyl-aluminium [39148-24-8]+TX, Hymexazol [10004-44-1]+TX, Iprovalicarb [140923-17-7]+TX, IKF-916 (Cyazofamid) [120116-88-3]+TX, Kasugamycin [6980-18-3]+TX, Methasulfocarb [66952-49-6]+TX, Metrafenone [220899-03-6]+TX, Pencycuron [66063-05-6]+TX, Phthalide [27355-22-2]+TX, Polyoxins [11113-80-7]+TX, Probenazole [27605-76-1]+TX, Propamocarb [25606-41-1]+TX, Proquinazid [189278-12-4]+TX, Pyroquilon [57369-32-1]+TX, Quinoxyfen [124495-18-7]+TX, Quintozene [82-68-8]+TX, Schwefel [7704-34-9]+TX, Tiadinil [223580-51-6]+TX, Triazoxide [72459-58-6]+TX, Tricyclazole [41814-78-2]+TX, Triforine [26644-46-2]+TX, Validamycin [37248-47-8]+TX, Zoxamide (RH7281) [156052-68-5]+TX, Mandipropamid [374726-62-2]+TX, the compound of formula F-1

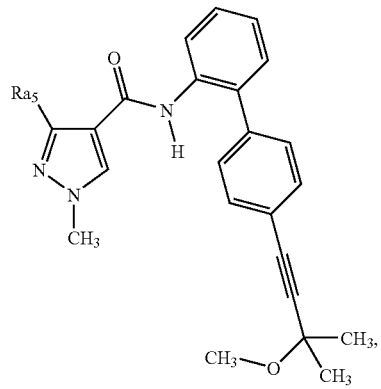

(F-1)

wherein $Ra_5$ is trifluoromethyl or difluoromethyl (WO2004/058723)+TX, the compound of formula F-2

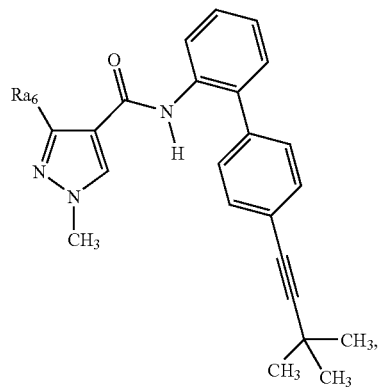

(F-2)

wherein $Ra_6$ is trifluoromethyl or difluoromethyl (WO2004/058723)+TX, the racemic compound of formula F-3 (syn)

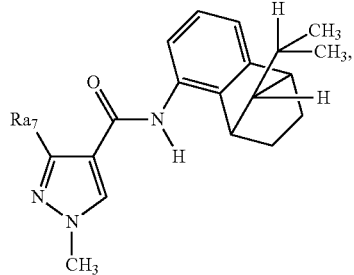

(F-3)

wherein $Ra_7$ is trifluoromethyl or difluoromethyl (WO2004/035589)+TX,
the racemic mixture of formula F-4 (anti)

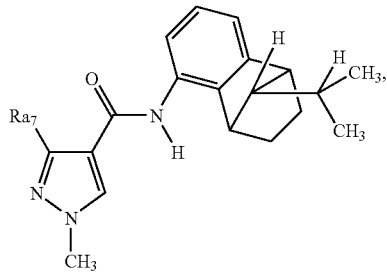

(F-4)

wherein $Ra_7$ is trifluoromethyl or difluoromethyl (WO2004/035589)+TX, the compound of formula F-5

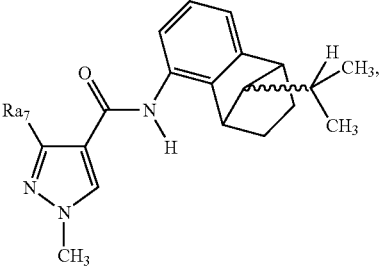

(F-5)

which is an epimeric mixture of racemic compounds of formulae F-3 (syn) and F-4 (anti), wherein the ratio from racemic compounds of formula F-3 (syn) to racemic compounds of formula F-4 (anti) is from 1000:1 to 1:1000 and wherein $Ra_7$ is trifluoromethyl or difluoromethyl (WO2004/035589)+TX, the compound of formula F-6

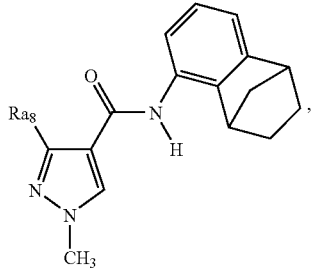

(F-6)

wherein $Ra_8$ is trifluoromethyl or difluoromethyl (WO2004/035589)+TX, the racemic compound of formula F-7 (trans)

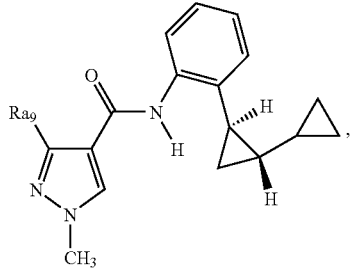

(F-7)

wherein Ra$_9$ is trifluoromethyl or difluoromethyl (WO03/074491)+TX, the racemic compound of formula F-8 (cis)

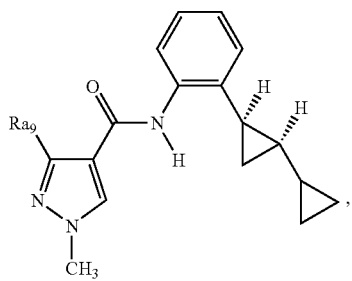

(F-8)

wherein Ra$_9$ is trifluoromethyl or difluoromethyl (WO03/074491)+TX, the compound of formula F-9

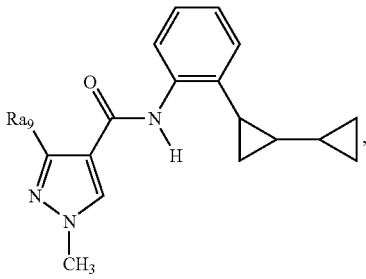

(F-9)

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra$_9$ is trifluoromethyl or difluoromethyl (WO03/074491)+TX, the compound of formula F-10

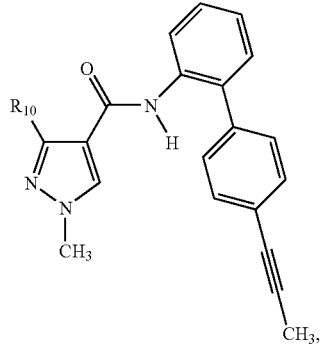

(F-10)

wherein R$_{10}$ is trifluoromethyl or difluoromethyl (WO2004/058723)+TX, the racemic compound of formula F-11 (trans)

(F-11)

wherein R$_{11}$ is trifluoromethyl or difluoromethyl (WO03/074491)+TX, the racemic compound of formula F-12 (cis)

(F-12)

wherein R$_{11}$ is trifluoromethyl or difluoromethyl (WO03/074491)+TX, the compound of formula F-13

(F-13)

which is a racemic mixture of formulae F-11 (trans) and F-12 (cis), and wherein R$_{11}$ is trifluoromethyl or difluoromethyl (WO 03/074491)+TX, the compound of formula F-14

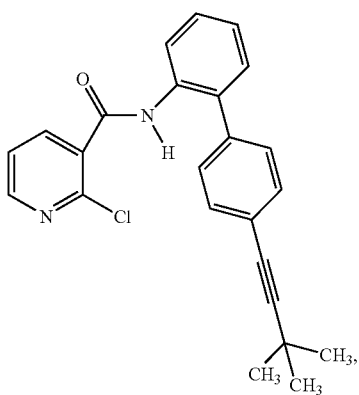

(WO2004/058723)+TX, and the compound of formula F-15

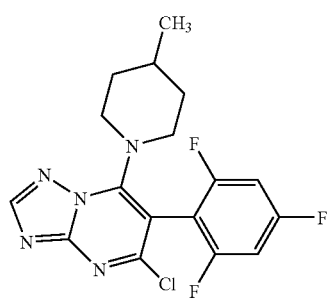

[214706-53-3],
+TX.

The references in brackets behind the active ingredients, e.g. [3878-19-1] refer to the Chemical Abstracts Registry number. The compounds of the formulae A-1 to A-26 are described in WO 03/015518 or in WO 04/067528. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright © 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from tables T1 to T57 with active ingredients described above comprises a compound selected from tables T1 to T57 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T57 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T57 and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

BIOLOGICAL EXAMPLES

%=Percent by Weight, Unless Otherwise Specified

Example B1

Activity Against *Spodoptera littoralis* (Egyptian Cotton Leafworm)

(Larvicide, Feeding/Residual Contact Activity, Preventive)

Cotton leaf discs are placed on agar in a 24-well microtiter plate and sprayed with test solutions. After drying, the leaf discs are infested with 5 $L_1$ larvae. The samples are checked for mortality, repellent effect, feeding behaviour, and growth regulation 3 days after treatment. In this test, compounds listed in Table P above show good activity. In particular compounds P.1, P.2, P.3, P.4, P.5, P.6, P.7, P.8, P.9, P.10, P.11, P.12, P.13, P.14, P.15, P.16, P.17, P.18, P.19, P.20, P.21, P.22, P.23, P.24, P.25, P.26, P.27, P.28, P.29, P.30, P.31, P.32, P.33, P.34, P.35, P.36, P.37, P.38, P.39, P.40, P.41, P.42, P.43, P.44, P.46, P.50, P.51, P.52, P.55, P.56, P.57, P.58, P.59, P.60, P61, P.66, P.67, P.68, P.69, P.70, P.71, P.72, P.73, P.74, P.75, P.76, P.77, P.78, P.83, P.84, P.87 and P.88 show an activity of over 80% at a concentration of 400 ppm.

Example B2

Activity Against *Heliothis virescens* (Tobacco Budworm)

(Ovo-Larvicide, Feeding/Contact Activity, Curative)

Eggs (0-24 h old) are placed in 24-well microtiter plate on artificial diet and treated with test solutions by pipetting. After an incubation period of 4 days, samples are checked for egg mortality, larval mortality, and growth regulation.

In this test, compounds listed in Table P above show good activity. In particular compounds P.1, P.2, P.3, P.4, P.5, P.6, P.7, P.8, P.9, P.10, P.11, P.12, P.13, P.14, P.15, P.16, P.17, P.18, P.19, P.20, P.21, P.22, P.23, P.24, P.25, P.26, P.27, P.28, P.29, P.30, P.31, P.32, P.33, P.34, P.35, P.36, P.37, P.38, P.39, P.40, P.41, P.42, P.43, P.44, P.46, P.49, P.51, P.52, P.54, P.55, P.56, P.57, P.58, P.59, P.60, P61, P.66, P.67, P.68, P.69, P.70, P.71, P.72, P.73, P.74, P.75, P.76, P.77, P.78, P.83, P.84, P.87 and P.88 show an activity of over 80% at a concentration of 400 ppm.

Example B3

*Plutella xylostella* (Diamond Back Moth)

(Larvicide, Feeding/Residual Contact Activity, Preventive)

24-well microtiter plate (MTP) with artificial diet is treated with test solutions by pipetting. After drying, the MTP's are infested with larvae (L2) (10-15 per well). After an incubation period of 5 days, samples are checked for larval mortality, antifeedant and growth regulation.

In this test, compounds listed in Table P above show good activity. In particular compounds P.1, P.2, P.3, P.4, P.5, P.6, P.7, P.8, P.9, P.10, P.11, P.12, P.13, P.14, P.15, P.16, P.17, P.18, P.19, P.20, P.21, P.22, P.23, P.24, P.25, P.26, P.27, P.28, P.29, P.30, P.31, P.32, P.33, P.34, P.35, P.36, P.37, P.38, P.39, P.40, P.41, P.42, P.43, P.44, P.46, P.48, P.49, P.50, P.51, P.52, P.53, P.54, P.55, P.56, P.57, P.58, P.59, P.60, P61, P.66, P.67, P.68, P.69, P.70, P.71, P.72, P.73, P.74, P.75, P.76, P.77, P.78, P.83, P.84, P.87 and P.88 show an activity of over 80% at a concentration of 400 ppm.

Example B4

*Diabrotica balteata* (Corn Root Worm)

(Larvicide, Feeding/Residual Contact Activity, Preventive)

24-well microtiter plate (MTP) with artificial diet is treated with test solutions by pipetting. After drying, the MTP's are infested with larvae (L2) (6-10 per well). After an incubation period of 5 days, samples are checked for larval mortality, antifeedant and growth regulation.

In this test, compounds listed in Table P above show good activity. In particular compounds P.1, P.2, P.3, P.4, P.6, P.8, P.10, P.11, P.13, P.15, P.16, P.17, P.18, P.19, P.20, P.21, P.22, P.23, P.24, P.25, P.26, P.27, P.28, P.29, P.30, P.31, P.32, P.36, P.37, P.38, P.39, P.40, P.41, P.42, P.43, P.44, P.46, P.49, P.54, P.57, P.60, P.67, P.68, P.69, P.70, P.73, P.74, P.75, P.78, P.83 and P.83 show an activity of over 80% at a concentration of 400 ppm.

Example B5

Activity Against *Myzus persicae* (Green Peach Aphid)

(Mixed Population, Feeding/Residual Contact Activity, Preventive)

Sunflower leaf discs are placed on agar in a 24-well microtiter plate and sprayed with test solutions. After drying, the leaf discs are infested with an aphid population of mixed ages. After an incubation period of 6 days, samples are checked for mortality and special effects (e.g. phytotoxicity).

In this test, compounds listed in Table P above show good activity. In particular compounds P.5, P.12, P.14, P.15, P.16, P.18, P.19, P.20, P.21, P.22, P.23, P.24, P.26, P.27, P.30, P.31, P.71, P.83 and P.88 show an activity of over 80% at a concentration of 400 ppm.

Example B6

Activity Against *Myzus persicae* (Green Peach Aphid)

(Mixed Population, Systemic/Feeding Activity, Curative)

Roots of pea seedlings, infested with an aphid population of mixed ages, are placed directly in the test solutions. 6 days after introduction, samples are checked for mortality and special effects on the plant.

In this test, compounds listed in Table P above show good activity. In particular compounds P.14, P.15, P.16, P.18, P.19, P.20, P.22, P.23, P.24, P.26, P.27, P.29, P.30, P.31 P.66, P.74, P.77 and P.76 show an activity of over 80% at a concentration of 400 ppm.

Example B7

Activity Against *Thrips tabaci* (Onion *Thrips*)

(Mixed Population, Feeding/Residual Contact Activity, Preventive)

Sunflower leaf discs are placed on agar in a 24-well microtiter plate and sprayed with test solutions. After drying, the leaf discs are infested with a thrips population of mixed ages. After an incubation period of 6 days, samples are checked for mortality and special effects (e.g. phytotoxicity).

In this test, compounds listed in Table P above show good activity. In particular compounds P.16, P.17, P.20 and P.83 show an activity of over 80% at a concentration of 400 ppm.

Example B8 to B9

Comparison of the Insecticidal Activity of Compounds According to the Invention with the Structurally Most Closely Comparable Compound from the State of the Art (Compound No. T91.3 Described on Page 71 of WO2005/085234)

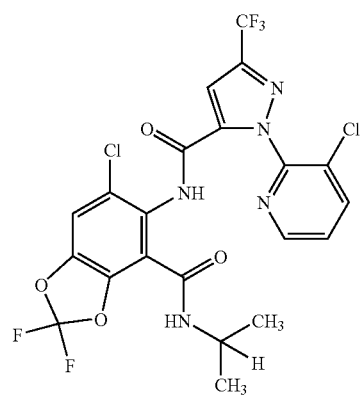 [SMILES: CC(C)NC(=O)c1c(NC(=O)c2cc(C(F)(F)F)nn2-c2ncccc2Cl)c(Cl)cc2c1OC(F)(F)O2]

(Compound No. P.13 according to the invention)

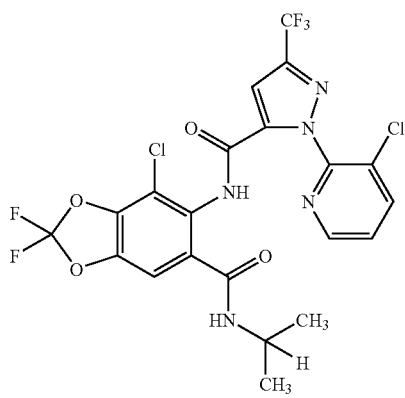 [SMILES: CC(C)NC(=O)c1cc2c(c(Cl)c1NC(=O)c1cc(C(F)(F)F)nn1-c1ncccc1Cl)OC(F)(F)O2]

(Compound No. T91.3 according to state of the art)

Example B8

*Plutella xylostella* (Diamond Back Moth)

(Larvicide, Feeding/Residual Contact Activity, Preventive)

24-well microtiter plate (MTP) with artificial diet is treated with test solutions by pipetting. After drying, the MTP's are infested with larvae (L2) (10-15 per well). After an incubation period of 5 days, samples are checked for larval mortality, antifeedant and growth regulation.

Results are shown in Table B8:

TABLE B8

Activity against *Plutella xylostella* (diamond back moth):

| Compound: | Concentration (ppm) | Death rate (%) after 5 days |
|---|---|---|
| Comp. T91.3 (state of the art) | 200 | 100 |
| Comp. T91.3 (state of the art) | 50 | 80 |
| Comp. T91.3 (state of the art) | 12.5 | 0 |
| Comp. P.13 (invention) | 200 | 100 |
| Comp. P.13 (invention) | 50 | 100 |
| Comp. P.13 (invention) | 12.5 | 100 |

Table B8 shows that compound No. P.13 according to the invention exerts a substantially better insecticidal action on *Plutella xylostella* than the compound from the state of the art. Especially at low application rates (12.5, 3.1 and 0.8 ppm) the compound according to the invention is far superior to the compound of the state of the art. This enhanced effect was not to be expected on the basis of the structural similarity of these compounds.

Example B9

Activity Against *Spodoptera littoralis* (Egyptian Cotton Leafworm)

(Larvicide, Feeding/Residual Contact Activity, Preventive)

Cotton leaf discs are placed on agar in a 24-well microtiter plate and sprayed with test solutions. After drying, the leaf discs are infested with 5 $L_1$ larvae. The samples are checked for mortality, repellent effect, feeding behaviour, and growth regulation 3 days after treatment.

TABLE B9

Activity against *Spodoptera littoralis* (Egyptian cotton leafworm):

| Compound: | Concentration (ppm) | Death rate (%) after 5 days |
|---|---|---|
| Comp. T91.3 (state of the art) | 200 | 100 (growth) |
| Comp. T91.3 (state of the art) | 50 | 0 |
| Comp. T91.3 (state of the art) | 12.5 | 0 |
| Comp. P.13 (invention) | 200 | 100 |
| Comp. P.13 (invention) | 50 | 100 |
| Comp. P.13 (invention) | 12.5 | 100 |

Table B9 shows that compound No. P.13 according to the invention exerts a substantially better insecticidal action on *Spodoptera littoralis* than the compound from the state of the art. Especially at low application rates (12.5, 3.1 and 0.8 ppm) the compound according to the invention is far superior to the compound of the state of the art. This enhanced effect was not to be expected on the basis of the structural similarity of these compounds.

The invention claimed is:
1. A compound of formula I:

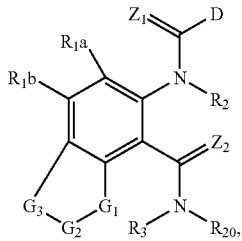

(I)

wherein:
G$_1$, G$_2$, and G$_3$, together with the two carbon atoms to which G$_1$ and G$_3$ are attached, form a non-aromatic 4- or 5-membered ring system; wherein:
G$_1$ is sulfur, SO, SO$_2$, oxygen, a direct bond, NR$_a$ or CR$_{5a}$R$_{5b}$;
G$_2$ is sulfur, SO, SO$_2$, oxygen, a direct bond, NR$_b$ or CR$_{5c}$R$_{5d}$;
G$_3$ is sulfur, SO, SO$_2$, oxygen, a direct bond, NR$_c$ or CR$_{5e}$R$_{5f}$;
with the provisos that
a) not more than 1 of G$_1$, G$_2$ and G$_3$ can be a direct bond,
b) not more than 2 of G$_1$, G$_2$ and G$_3$ can be oxygen, sulfur, SO or SO$_2$ and
c) when 2 of G$_1$, G$_2$ and G$_3$ are each independently oxygen, SO, SO$_2$ or sulfur, the two groups are separated by a carbon atom;
each of R$_{1a}$, R$_{1b}$, R$_{5a}$, R$_{5b}$, R$_{5c}$, R$_{5d}$ R$_{5e}$, and R$_{5f}$, which may be the same or different, independently represents hydrogen, halogen, nitro, cyano, hydroxy, CHO, NH$_2$, C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_4$alkoxy, C$_1$-C$_4$alkoxy-C$_1$-C$_4$alkoxy-C$_1$-C$_4$alkyl, C$_1$-C$_4$haloalkoxy, C$_1$-C$_4$alkylthio, C$_1$-C$_4$haloalkylthio, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_1$-C$_4$alkylsulfonyl-C$_1$-C$_4$alkyl, C$_1$-C$_4$alkylsulfoximino-C$_1$-C$_4$alkyl, C$_1$-C$_4$alkylamino, C$_2$-C$_4$dialkylamino, C$_3$-C$_6$cycloalkylamino, C$_1$-C$_6$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, C$_1$-C$_4$alkoxyimino-C$_1$-C$_4$alkyl, C$_3$-C$_6$-trialkylsilyl, phenyl, benzyl or phenoxy; or phenyl, benzyl or phenoxy mono-, di- or tri-substituted by halogen, cyano, nitro, halogen, C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_4$alkoxy, C$_1$-C$_4$haloalkoxy, C$_1$-C$_4$alkylthio, C$_1$-C$_4$haloalkylthio, C$_1$-C$_4$alkylsulfinyl, C$_1$-C$_4$alkylsulfonyl, C$_1$-C$_4$alkylamino, C$_2$-C$_4$dialkylamino, C$_3$-C$_6$cycloalkylamino, C$_1$-C$_6$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy or C$_3$-C$_6$-trialkylsilyl;
each of R$_a$, R$_b$ and R$_c$, which may be the same or different, independently represents H, OH, C$_1$-C$_6$alkyl, C$_3$-C$_6$cycloalkyl, C$_1$-C$_6$haloalkyl, halogen, cyano, nitro, NH$_2$, NR$_{23}$R$_{24}$ C$_1$-C$_6$alkoxy, C$_1$-C$_6$haloalkoxy, C$_2$-C$_6$alkoxycarbonyl, C$_1$-C$_6$alkylthio, C$_1$-C$_6$haloalkylthio, C$_1$-C$_6$alkylsulfinyl, C$_1$-C$_6$alkylsulfonyl, C$_1$-C$_6$haloalkylsulfinyl, C$_1$-C$_6$haloalkylsulfonyl, C$_2$-C$_6$ alkoxycarbonyl, C$_2$-C$_6$ alkylcarbonyl, C$_2$-C$_6$-trialkylsilyl, benzyl, phenoxy, or a three- to ten-membered, monocyclic or fused bicyclic ring system which may be aromatic, partially saturated or fully saturated, and when said three- to ten-membered, monocyclic or fused bicyclic ring system comprises a six-membered aromatic ring system, the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_2$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, C$_2$-C$_8$ dialkylaminocarbonyl and C$_2$-C$_6$ trialkylsilyl; it being possible for said three- to ten-membered, monocyclic or fused bicyclic ring system to be spiro-bonded to the C$_3$-C$_6$cycloalkyl group;
each of R$_2$, R$_3$, R$_{23}$, R$_{24}$, R$_{25}$ and R$_{29}$, which may be the same or different, independently represents hydrogen, C$_1$-C$_6$alkyl, C$_2$-C$_6$alkenyl, C$_2$-C$_6$alkynyl or C$_3$-C$_8$cycloalkyl; or C$_1$-C$_6$alkyl, C$_2$-C$_6$alkenyl, C$_2$-C$_6$alkynyl or C$_3$-C$_8$cycloalkyl substituted by one or more substituents selected from halogen nitro, cyano, hydroxy, C$_1$-C$_4$alkoxy, C$_1$-C$_4$haloalkoxy, C$_1$-C$_4$alkylthio, C$_1$-C$_4$haloalkylthio, C$_1$-C$_4$alkylsulfinyl, C$_1$-C$_4$alkylsulfonyl, C$_1$-C$_4$alkylamino, C$_2$-C$_4$dialkylamino, C$_3$-C$_6$cycloalkylamino and C$_1$-C$_6$alkyl-C$_3$-C$_6$cycloalkylamino;
or R$_{5a}$ and R$_{5b}$ or R$_{5c}$, and R$_{5d}$ or R$_{5e}$ and R$_{5f}$ can together form =Y, where Y can be O, S or NR$_{21}$;
D is 2-pyridyl, 3-pyridyl or 4-pyridyl; or 2-pyridyl, 3-pyridyl or 4-pyridyl mono-, di- or tri-substituted by C$_1$-C$_6$alkyl, C$_3$-C$_6$cycloalkyl, C$_1$-C$_6$haloalkyl, halogen, cyano, C$_1$-C$_4$alkoxy, C$_1$-C$_4$haloalkoxy, C$_1$-C$_4$alkylthio C$_1$-C$_4$haloalkylthio C$_1$-C$_4$alkylsulfinyl, C$_1$-C$_4$alkylsulfonyl C$_1$-C$_4$haloalkylsulfinyl or C$_1$-C$_4$haloalkylsulfonyl;

or D is a group selected from:

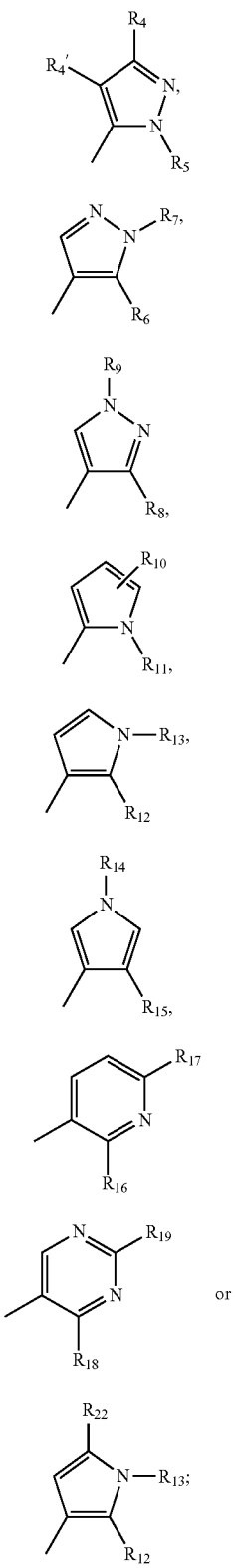

or D is additionally phenyl if $Z_1$ is sulfur;

$R_4$, $R_4'$, $R_{10}$, $R_{17}$, and $R_{19}$, independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_5$, $R_6$, $R_8$, $R_{11}$, $R_{12}$, $R_{15}$, $R_{16}$ and $R_{18}$, independently from each other, are $C_1$-$C_6$alkyl, or $C_1$-$C_6$alkyl mono-, di- or tri-substituted by halogen, cyano, nitro, hydroxy, $C_1$-$C_4$alkoxy, $C_2$-$C_4$alkoxycarbonyl, $C_1$-$C_4$alkylthio $C_1$-$C_4$alkylsulfinyl, $C_1$-$C_4$alkylsulfonyl, $C_1$-$C_4$alkylamino, $C_2$-$C_4$dialkylamino or $C_3$-$C_6$cycloalkylamino; or are each independently phenyl, 2-pyridyl, 3-pyridyl, or 4-pyridyl; or are each independently phenyl, 2-pyridyl, 3-pyridyl or 4-pyridyl mono-, di- or tri-substituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulfinyl, $C_1$-$C_4$alkylsulfonyl, $C_1$-$C_4$haloalkylsulfinyl or $C_1$-$C_4$haloalkylsulfonyl;

$R_7$, $R_9$, $R_{13}$ and $R_{14}$, independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio $C_1$-$C_4$alkylsulfinyl, $C_1$-$C_4$alkylsulfonyl $C_1$-$C_4$alkylsulfoximino, $C_2$-$C_6$ alkoxycarbonyl, $C_2$-$C_6$ alkylcarbonyl, $C_2$-$C_6$-trialkylsilyl, benzyl, phenoxy, or a three- to ten-membered, monocyclic or fused bicyclic ring system which may be aromatic, partially saturated or fully saturated, and when said three- to ten-membered, monocyclic or fused bicyclic ring system comprises a six-membered aromatic ring system, the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino $C_1$-$C_4$alkylamino $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl; it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

or $R_{20}$ is 3-oxetanyl, 3-thietanyl, 1-oxo-3-thietanyl, 1,1-dioxo-3-thietanyl, 1-imino-1-oxo-3-thietanyl, 3-azetdinyl, each optionally substituted with one to five substituents independently selected from $C_1$-$C_4$ alkyl, $C_1$-$C_4$ haloalkyl, halogen, and cyano;

each of $Z_1$ and $Z_2$, which may be the same or different, independently represents oxygen or sulfur;

$R_{21}$ is hydrogen, OH, $C_1$-$C_6$alkyl, $C_3$-$C_6$cycloalkyl, $C_1$-$C_6$haloalkyl, halogen, cyano, nitro, $NH_2$, $NR_{25}R_{29}$, $C_1$-$C_6$alkoxy, $C_1$-$C_6$haloalkoxy, $C_2$-$C_6$alkoxycarbonyl, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$haloalkylsulfinyl, $C_1$-$C_6$haloalkylsulfonyl, $C_2$-$C_6$ alkoxycarbonyl, $C_2$-$C_6$ alkylcarbonyl, $C_2$-$C_6$-trialkylsilyl, benzyl, phenoxy, or a three- to ten-membered, monocyclic or fused bicyclic ring system which may be aromatic, partially saturated or fully saturated, and when said three- to ten-membered, monocyclic or fused bicyclic ring system comprises a six-membered aromatic ring system, the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl; it being possible for said three- to ten-membered, monocyclic or fused bicyclic ring system to be spiro-bonded to the $C_3$-$C_6$cycloalkyl group;

$R_{22}$ is $C_1$-$C_6$alkyl, $C_3$-$C_6$cycloalkyl, $C_1$-$C_6$haloalkyl, halogen, cyano, nitro, $C_1$-$C_6$alkoxy, $C_1$-$C_6$haloalkoxy, $C_2$-$C_6$alkoxycarbonyl, $C_1$-$C_6$alkylthio, $C_1$-$C_6$haloalkylthio, $C_1$-$C_6$alkylsulfinyl, $C_1$-$C_6$alkylsulfonyl, $C_1$-$C_6$haloalkylsulfinyl or $C_1$-$C_6$haloalkylsulfonyl;

and agronomically acceptable salts/isomers/enantiomers/tautomers/N-oxides of said compound.

2. A compound of claim 1, wherein:

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$-trialkylsilyl, benzyl, phenoxy, and a three- to ten-membered, monocyclic or fused bicyclic ring system which may be aromatic, partially saturated or fully saturated, and when said three- to ten-membered, monocyclic or fused bicyclic ring system comprises a six-membered aromatic ring system, the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl; it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl.

3. A compound of claim 1 represented by the formula IA:

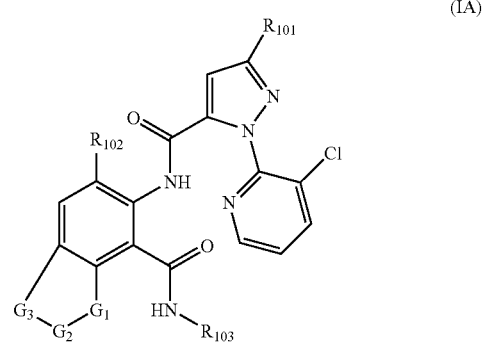

(IA)

wherein:

$R_{101}$ is halogen, $C_1$-$C_4$haloalkyl, $C_1$-$C_4$haloalkoxy or $C_1$-$C_4$alkoxy;

$R_{102}$ is hydrogen, halogen, $C_1$-$C_6$-alkyl, $C_2$-$C_6$-alkynyl or cyano; and $R_{103}$ is hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)(NH)CH_3$, $C(CH_3)_2CH_2S(O)_2CH_3$, $CH_2CN$, $CH(CH_3)CH_2SCH_3$, $CH(CH_3)CH_2S(O)CH_3$, $CH(CH_3)CH_2S(O)_2CH_3$, 3-methyl-thietan-3-yl, 1-oxo-3-methyl-thietan-3-yl or 1,1-dioxo-3-methyl-thietan-3-yl.

4. A pesticidal composition, which comprises at least one compound according to claim 1 or a tautomer thereof, in each case in free form or in agrochemically utilizable salt form.

5. A composition according to claim 4 for controlling insects or representatives of the order Acarina.

6. A method for controlling pests, which comprises applying a composition according to claim 4 to the pests or their environment.

7. A method according to claim 6 for controlling insects or representatives of the order Acarina.

8. A method according to claim 6 for the protection of plant propagation material from the attack by pests, which comprises treating the propagation material or the site, where the propagation material is planted.

9. A compound of claim 1, wherein:

$G_1$ is sulfur, SO, $SO_2$, oxygen, $NR_a$ or $CR_{5a}R_{5b}$;

$G_2$ is $CR_{5c}R_{5d}$; and $G_3$ is sulfur, SO, $SO_2$, oxygen, $NR_c$ or $CR_{5e}R_{5f}$.

10. A compound of claim 9, wherein:

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_6$ alkoxycarbonyl, $C_2$-$C_6$ alkylcarbonyl, $C_2$-$C_6$-trialkylsilyl, benzyl, phenoxy, or a three- to ten-membered, monocyclic or fused bicyclic ring system which may be aromatic, partially saturated or fully saturated, and when said three- to ten-membered, monocyclic or fused bicyclic ring system comprises a six-membered aromatic ring system, the six-membered aromatic ring system contains at least one heteroatom selected from the group consisting of oxygen, nitro and sulfur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl; it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl.

11. A compound of claim 9 represented by the formula IA:

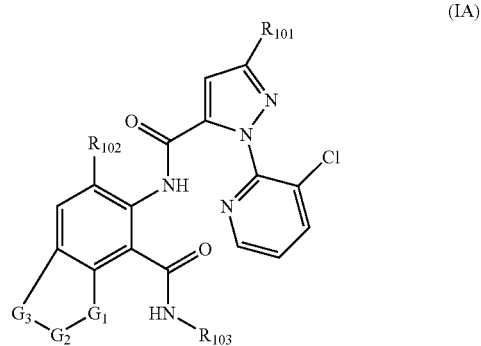

(IA)

wherein:
$R_{101}$ is halogen, $C_1$-$C_4$haloalkyl, $C_1$-$C_4$haloalkoxy or $C_1$-$C_4$alkoxy;
$R_{102}$ is hydrogen, halogen, $C_1$-$C_6$-alkyl, $C_2$-$C_6$-alkynyl or cyano; and
$R_{103}$ is hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)(NH)CH_3$, $C(CH_3)_2CH_2S(O)_2CH_3$, $CH_2CN$, $CH(CH_3)CH_2SCH_3$, $CH(CH_3)CH_2S(O)CH_3$, $CH(CH_3)CH_2S(O)_2CH_3$, 3-methyl-thietan-3-yl, 1-oxo-3-methyl-thietan-3-yl or 1,1-dioxo-3-methyl-thietan-3-yl.

12. A pesticidal composition, which comprises at least one compound according to claim 9 or a tautomer thereof, in each case in free form or in agrochemically utilizable salt form.

13. A composition according to claim 12 for controlling insects or representatives of the order Acarina.

14. A method for controlling pests, which comprises applying a composition according to claim 12 to the pests or their environment.

15. A method according to claim 14 for controlling insects or representatives of the order Acarina.

16. A method according to claim 14 for the protection of plant propagation material from the attack by pests, which comprises treating the propagation material or the site, where the propagation material is planted.

* * * * *